US011136631B2

(12) United States Patent
Wuitschick et al.

(10) Patent No.: US 11,136,631 B2
(45) Date of Patent: Oct. 5, 2021

(54) ASSAY FOR DETECTING HUMAN IMMUNODEFICIENCY VIRUS (HIV)

(71) Applicant: ABBOTT MOLECULAR INC., Des Plaines, IL (US)

(72) Inventors: Jeffrey Wuitschick, Des Plaines, IL (US); Shihai Huang, Des Plaines, IL (US); Tomasz Krupinski, Des Plaines, IL (US); John Karavitis, Des Plaines, IL (US); John Salituro, Des Plaines, IL (US); Anna Sobol, Des Plaines, IL (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 237 days.

(21) Appl. No.: 16/150,001

(22) Filed: Oct. 2, 2018

(65) Prior Publication Data

US 2019/0100812 A1    Apr. 4, 2019

Related U.S. Application Data

(60) Provisional application No. 62/567,655, filed on Oct. 3, 2017.

(51) Int. Cl.
*C12Q 1/68* (2018.01)
*C12Q 1/70* (2006.01)

(52) U.S. Cl.
CPC .......... *C12Q 1/703* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

| 5,270,184 | A | 12/1993 | Walker et al. | |
|---|---|---|---|---|
| 5,455,166 | A | 10/1995 | Walker | |
| 5,677,124 | A | 10/1997 | Dubois et al. | |
| 5,919,625 | A | 7/1999 | Dubois et al. | |
| 5,939,262 | A | 8/1999 | Pasloske et al. | |
| 6,001,558 | A | 12/1999 | Backus et al. | |
| 7,629,153 | B2 * | 12/2009 | Trono ...................... | C12N 7/00 435/91.4 |
| 8,609,340 | B2 * | 12/2013 | Eickhoff ................. | C12Q 1/708 435/6.12 |
| 8,932,817 | B2 * | 1/2015 | Kacian ................... | C12Q 1/6851 435/6.12 |
| 9,388,455 | B2 | 7/2016 | Abravaya et al. | |
| 10,472,668 | B2 * | 11/2019 | Abravaya ............. | C12Q 1/6832 |
| 2014/0087381 | A1 | 3/2014 | Abravaya et al. | |

FOREIGN PATENT DOCUMENTS

WO    WO 2015127201 A1    8/2015

OTHER PUBLICATIONS

Drosten et al. (Clin Chem, 2006, 52:7, 1258-1266) (Year: 2006).*
Abbott RealTime HIV-1 Assay (CE); package insert No. 51-602100/ R5, dated Mar. 2009, 8 pages.
Abbott RealTime HIV-1 Assay (FDA); package insert No. 51-602146/ R2, dated May 2007, 59 pages.
Albert et al., "Rapid development of isolate-specific neutralizing antibodies after primary HIV-1 infection and consequent emergence of virus variants which resist neutralization by autologous sera." AIDS. Feb. 1990; 4(2):107-12.
Bar et al., "Validation of kinetics similarity in qPCR." Nucleic Acids Res. Feb. 2012; 40(4):1395-406.
Barre-Sinoussi et al., "Isolation of a T-lymphotropic retrovirus from a patient at risk for acquired immune deficiency syndrome (AIDS)." Science. May 20, 1983; 220(4599):868-71.
Beckam Coulter Veris HIV-1 Assay (CE); package insert No. B41872 Al, Jul. 2015.
Beckam Coulter Veris HIV-1 Assay, 2016 retrieved [Aug. 16, 2016], <https://www.beckmancoulter.com/wsrportal/wsr/v2/diagnostics/clinical-products/molecular-diagnostics/veris-hiv-1-assay/index.html>.
Campbell-Yesufu & Gandhi, "Update on human immunodeficiency virus (HIV)-2 infection." Clin Infect Dis. Mar. 15, 2011; 52(6):780-7.
Cepheid Gene Xpert HIV-1 Assay (CE); package insert No. 301-3068, Rev. C, Jan. 2015, 26 pages.
Chene et al., "Prognostic importance of initial response in HIV-1 infected patients starting potent antiretroviral therapy: analysis of prospective studies." Lancet. Aug. 30, 2003; 362(9385):679-86.
Clark et al., "High titers of cytopathic virus in plasma of patients with symptomatic primary HIV-1 infection" N Engl J Med. Apr. 4, 1991; 324(14):954-60.
Curran et al., "Epidemiology of HIV infection and AIDS in the United States." Science. Feb. 5, 1988; 239(4840):610-6.
Daar et al., "Transient high levels of viremia in patients with primary human immunodeficiency virus type 1 infection." N Engl J Med. Apr. 4, 1991; 324(14):961-4.
Dewar et al., "Application of branched DNA signal amplification to monitor human immunodeficiency virus type 1 burden in human plasma." J Infect Dis. Nov. 1994; 170(5):1172-9.
Dhanasekaren et al., "Comparison of different standards for real-time PCR-based absolute quantification." J Immunol Methods. Mar. 31, 2010; 354(1-2):34-9.
Egger et al., "Prognosis of HIV-1-infected patients starting highly active antiretroviral therapy: a collaborative analysis of prospective studies." Lancet. Jul. 13, 2002; 360(9327):119-29.
Fibriani et al., "Low cost HIV-1 quantitative RT-PCR assay in resource-limited settings: improvement and implementation." J Virol Methods. Oct. 2012; 185(1):118-23.

(Continued)

*Primary Examiner* — Stephanie K Mummert
(74) *Attorney, Agent, or Firm* — Casimir Jones, S.C.; Melissa Karabinis

(57) ABSTRACT

The disclosure is directed to methods, kits, and compositions for amplifying and detecting a human immunodeficiency virus-1 (HIV-1) in a sample, which comprises a variety of combinations of forward oligonucleotide primers, reverse oligonucleotide primers, and oligonucleotide probes.

11 Claims, 22 Drawing Sheets

Specification includes a Sequence Listing.

(56) References Cited

OTHER PUBLICATIONS

Gallo et al., "Frequent detection and isolation of cytopathic retroviruses (HTLV-III) from patients with AIDS and at risk for AIDS." Science. May 4, 1984; 224(4648):500-3.

Gallo et al., "HIV/HTLV gene nomenclature." Nature. Jun. 9, 1988; 333(6173):504.

Ho et al., "Rapid turnover of plasma virions and CD4 lymphocytes in HIV-1 infection." Nature. Jan. 12, 1995; 373(6510):123-6.

Hologic Aptima HIV-1 Quant Dx Assay (CE); package insert No. AW-11853-001, rev. 001, 2014, 37 pages.

Hologic Aptima HIV-1 Quant Dx Assay (US); package insert No. AW-13242-REG., rev. 002, 2016, 35 pages.

Horsburgh et al., "Duration of Human Immunodeficiency Virus Infection Before Detection of Antibody." Lancet, 334: 637-640 (1989).

Huang et al., "Thermodynamically modulated partially double-stranded linear DNA probe design for homogeneous real-time PCR." Nucleic Acids Research, Aug. 2007, 35(16): e101.

Lu et al., "Structural determinants and mechanism of HIV-1 genome packaging." J Mol Biol. Jul. 22, 2011; 410(4):609-33.

Luft et al., "HIV-1 viral diversity and its implications for viral load testing: review of current platforms." Int J Infect Dis. Oct. 2011; 15(10):e661-70.

Luk et al., "Partially double-stranded linear DNA probes: novel design for sensitive detection of genetically polymorphic targets." J Virol Methods. Sep. 2007; 144(1-2):1-11.

Mellors et al., "Plasma viral load and CD4+ lymphocytes as prognostic markers of HIV-1 infection." Ann Intern Med. Jun. 15, 1997; 126(12):946-54.

Mellors et al., "Prognosis in HIV-1 infection predicted by the quantity of virus in plasma." Science. May 24, 1996; 272(5265):1167-70.

Montagnier, Luc., Human Immunodeficiency Viruses (Retroviridae). Encyclopedia of Virology (2nd Ed.), pp. 763-774 (1999).

Muesing et al., "Nucleic acid structure and expression of the human AIDS/lymphadenopathy retrovirus." Nature. Feb. 7-13, 1985; 313(6002):450-8.

Mulder et al., "Rapid and simple PCR assay for quantitation of human immunodeficiency virus type 1 RNA in plasma: application to acute retroviral infection." J Clin Microbiol. Feb. 1994; 32(2):292-300.

Nyamweya et al., "Comparing HIV-1 and HIV-2 infection: Lessons for viral immunopathogenesis." Rev. Med. Virol., Rev Med Virol. Jul. 2013; 23(4):221-40.

Pantleo et al., "The immunopathogenesis of human immunodeficiency virus infection." N Engl J Med. Feb. 4, 1993; 328(5):327-35.

Pasloske et al., "Armored RNA technology for production of ribonuclease-resistant viral RNA controls and standards." J Clin Microbiol. Dec. 1998; 36(12):3590-4.

Perelson et al., "Decay characteristics of HIV-1-infected compartments during combination therapy." Nature. May 8, 1997; 387(6629):188-91.

Popovic et al., "Detection, isolation, and continuous production of cytopathic retroviruses (HTLV-III) from patients with AIDS and pre-AIDS." Science. May 4, 1984; 224(4648):497-500.

Roche cobas HIV-1 4800 Assay (CE); package insert No. 07529708001-02EN, rev. 1.0, Aug. 2015, 31 pages.

Roche cobas HIV-1 6800/8800 Assay (CE); package insert No. EN07175426001-03EN, rev. 1.0.

U.S. Department of Health and Human Services, Guidelines for the Use of Antiretroviral Agents in HIV-1 Infected Adults and Adolescents (Jul. 2016).

Van Gemen et al., "Quantification of HIV-1 RNA in plasma using NASBA during HIV-1 primary infection." J Virol Methods. Jul. 1993; 43(2):177-87.

Wang et al., "Advances in developing HIV-1 viral load assays for resource-limited settings." Biotechnol Adv. Nov.-Dec. 2010; 28(6):770-81.

Wei et al., "Viral dynamics in human immunodeficiency virus type 1 infection." Nature. Jan. 12, 1995; 373(6510):117-22.

Wood et al., "Higher baseline levels of plasma human immunodeficiency virus type 1 RNA are associated with increased mortality after initiation of triple-drug antiretroviral therapy." J Infect Dis. Nov. 15, 2003; 188(10):1421-5.

Yeni et al., "Treatment for adult HIV infection: 2004 recommendations of the International AIDS Society-USA Panel." JAMA, 292: 251-265 (2004).

\* cited by examiner

SEQUENCE LISTING

```
<160> NUMBER OF SEQ ID NOS: 54

<210> SEQ ID NO 1
<211> LENGTH: 29
<212> TYPE: DNA
<213> ORGANISM: Artificial Sequence
<220> FEATURE:
<223> OTHER INFORMATION: Synthetic

<400> SEQUENCE: 1
attccctaca atccccaaag tcaaggagt                                      29

<210> SEQ ID NO 2
<211> LENGTH: 26
<212> TYPE: DNA
<213> ORGANISM: Artificial Sequence
<220> FEATURE:
<223> OTHER INFORMATION: Synthetic

<400> SEQUENCE: 2
ctttcccctg cactgtaccc cccaat                                         26

<210> SEQ ID NO 3
<211> LENGTH: 43
<212> TYPE: DNA
<213> ORGANISM: Artificial Sequence
<220> FEATURE:
<223> OTHER INFORMATION: Synthetic

<400> SEQUENCE: 3
acagcagtac agatggcagt attcattcac aattttaaaa gaa                      43

<210> SEQ ID NO 4
<211> LENGTH: 16
<212> TYPE: DNA
<213> ORGANISM: Artificial Sequence
<220> FEATURE:
<223> OTHER INFORMATION: Synthetic
```

```
<400> SEQUENCE: 4
cggatttgta ctgctg                                              16

<210> SEQ ID NO 5
<211> LENGTH: 27
<212> TYPE: DNA
<213> ORGANISM: Artificial Sequence
<220> FEATURE:
<223> OTHER INFORMATION: Synthetic

<400> SEQUENCE: 5
aagcctcaat aaagcttgcc ttgagtg                                  27

<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
gtccctgttc gggcgccact gctag                                    25

<210> SEQ ID NO 7
<211> LENGTH: 47
<212> TYPE: DNA
<213> ORGANISM: Artificial Sequence
<220> FEATURE:
<223> OTHER INFORMATION: Synthetic

<400> SEQUENCE: 7
tgtgtgcccg tctgttgtgc gactctggta tctagagatc cctcaga           47

<210> SEQ ID NO 8
<211> LENGTH: 11
<212> TYPE: DNA
<213> ORGANISM: Artificial Sequence
<220> FEATURE:
<223> OTHER INFORMATION: Synthetic

<400> SEQUENCE: 8
acgggcacac a                                                   11

<210> SEQ ID NO 9
<211> LENGTH: 43
<212> TYPE: DNA
<213> ORGANISM: Artificial Sequence
<220> FEATURE:
<223> OTHER INFORMATION: Synthetic

<400> SEQUENCE: 9
agtgtgtgct catctgttca accctggtat ctagagatcc ctc                43

<210> SEQ ID NO 10
<211> LENGTH: 14
<212> TYPE: DNA
<213> ORGANISM: Artificial Sequence
<220> FEATURE:
<223> OTHER INFORMATION: Synthetic

<400> SEQUENCE: 10
gatgagcaca cact                                                14

<210> SEQ ID NO 11
```

```
<211> LENGTH: 27
<212> TYPE: DNA
<213> ORGANISM: Artificial Sequence
<220> FEATURE:
<223> OTHER INFORMATION: Synthetic

<400> SEQUENCE: 11
cagagttggc agcttcactt tctcttg                                         27

<210> SEQ ID NO 12
<211> LENGTH: 22
<212> TYPE: DNA
<213> ORGANISM: Artificial Sequence
<220> FEATURE:
<223> OTHER INFORMATION: Synthetic

<400> SEQUENCE: 12
gtctggcctt tcagcaagtt tc                                              22

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
acgagttcat gagggcaggc cgct                                            24

<210> SEQ ID NO 14
<211> LENGTH: 29
<212> TYPE: DNA
<213> ORGANISM: Artificial Sequence
<220> FEATURE:
<223> OTHER INFORMATION: Synthetic

<400> SEQUENCE: 14
attccctaca atccccaaag tcaaggagt                                       29

<210> SEQ ID NO 15
<211> LENGTH: 29
<212> TYPE: DNA
<213> ORGANISM: Artificial Sequence
<220> FEATURE:
<223> OTHER INFORMATION: Synthetic

<400> SEQUENCE: 15
attccctaca atccccaaag tcaaggagt                                       29

<210> SEQ ID NO 16
<211> LENGTH: 29
<212> TYPE: DNA
<213> ORGANISM: Artificial Sequence
<220> FEATURE:
<223> OTHER INFORMATION: Synthetic

<400> SEQUENCE: 16
attccctaca atccccaaag tcaaggagt                                       29

<210> SEQ ID NO 17
<211> LENGTH: 29
<212> TYPE: DNA
<213> ORGANISM: Artificial Sequence
<220> FEATURE:
<223> OTHER INFORMATION: Synthetic

<400> SEQUENCE: 17
```

```
attccctaca atccccaaag tcaaggagt                                              29

<210> SEQ ID NO 18
<211> LENGTH: 29
<212> TYPE: DNA
<213> ORGANISM: Artificial Sequence
<220> FEATURE:
<223> OTHER INFORMATION: Synthetic

<400> SEQUENCE: 18
attcccuaca atccccaaag tcaaggagt                                              29

<210> SEQ ID NO 19
<211> LENGTH: 29
<212> TYPE: DNA
<213> ORGANISM: Artificial Sequence
<220> FEATURE:
<223> OTHER INFORMATION: Synthetic

<400> SEQUENCE: 19
attcccuaca atccccaaag tcaaggagt                                              29

<210> SEQ ID NO 20
<211> LENGTH: 29
<212> TYPE: DNA
<213> ORGANISM: Artificial Sequence
<220> FEATURE:
<223> OTHER INFORMATION: Synthetic

<400> SEQUENCE: 20
attccctaca atccccaaag tcaaggagt                                              29

<210> SEQ ID NO 21
<211> LENGTH: 29
<212> TYPE: DNA
<213> ORGANISM: Artificial Sequence
<220> FEATURE:
<223> OTHER INFORMATION: Synthetic

<400> SEQUENCE: 21
attccctaca atccccaaag tcaaggagt                                              29

<210> SEQ ID NO 22
<211> LENGTH: 29
<212> TYPE: DNA
<213> ORGANISM: Artificial Sequence
<220> FEATURE:
<223> OTHER INFORMATION: Synthetic

<400> SEQUENCE: 22
attcccuaca atccccaaag tcaaggagt                                              29

<210> SEQ ID NO 23
<211> LENGTH: 28
<212> TYPE: DNA
<213> ORGANISM: Artificial Sequence
<220> FEATURE:
<223> OTHER INFORMATION: Synthetic

<400> SEQUENCE: 23
attccctaca atccccaaag tcaaggag                                               28

<210> SEQ ID NO 24
<211> LENGTH: 29
<212> TYPE: DNA
```

```
<213> ORGANISM: Artificial Sequence
<220> FEATURE:
<223> OTHER INFORMATION: Synthetic

<400> SEQUENCE: 24 atacccctaca atcctcaaag tcagggagc                                    29

<210> SEQ ID NO 25
<211> LENGTH: 27
<212> TYPE: DNA
<213> ORGANISM: Artificial Sequence
<220> FEATURE:
<223> OTHER INFORMATION: Synthetic

<400> SEQUENCE: 25
accctacaat cctcaaagtc agggagc                                       27

<210> SEQ ID NO 26
<211> LENGTH: 27
<212> TYPE: DNA
<213> ORGANISM: Artificial Sequence
<220> FEATURE:
<223> OTHER INFORMATION: Synthetic

<400> SEQUENCE: 26 gggatacccct acaatcctca aagtcag                                      27

<210> SEQ ID NO 27
<211> LENGTH: 27
<212> TYPE: DNA
<213> ORGANISM: Artificial Sequence
<220> FEATURE:
<223> OTHER INFORMATION: Synthetic

<400> SEQUENCE: 27
cgggataccc tacaatcctc aaagtca                                       27

<210> SEQ ID NO 28
<211> LENGTH: 28
<212> TYPE: DNA
<213> ORGANISM: Artificial Sequence
<220> FEATURE:
<223> OTHER INFORMATION: Synthetic

<400> SEQUENCE: 28
cgggataccc tacaatcctc aaagtcag                                      28

<210> SEQ ID NO 29
<211> LENGTH: 27
<212> TYPE: DNA
<213> ORGANISM: Artificial Sequence
<220> FEATURE:
<223> OTHER INFORMATION: Synthetic

<400> SEQUENCE: 29
cctacaatcc tcaaagtcag ggagcag                                       27

<210> SEQ ID NO 30
<211> LENGTH: 29
<212> TYPE: DNA
<213> ORGANISM: Artificial Sequence
<220> FEATURE:
<223> OTHER INFORMATION: Synthetic

<400> SEQUENCE: 30 gatacccctac aatcctcaaa gtcagggag                                    29
```

<210> SEQ ID NO 31
<211> LENGTH: 29
<212> TYPE: DNA
<213> ORGANISM: Artificial Sequence
<220> FEATURE:
<223> OTHER INFORMATION: Synthetic

<400> SEQUENCE: 31
ataccatata atccacaaag tcaaggagt                                29

<210> SEQ ID NO 32
<211> LENGTH: 29
<212> TYPE: DNA
<213> ORGANISM: Artificial Sequence
<220> FEATURE:
<223> OTHER INFORMATION: Synthetic

<400> SEQUENCE: 32
ataccatata acccacaaag tcaaggagt                                29

<210> SEQ ID NO 33
<211> LENGTH: 31
<212> TYPE: DNA
<213> ORGANISM: Artificial Sequence
<220> FEATURE:
<223> OTHER INFORMATION: Synthetic

<400> SEQUENCE: 33
gaataccata taatccacaa agtcaaggag t                             31

<210> SEQ ID NO 34
<211> LENGTH: 31
<212> TYPE: DNA
<213> ORGANISM: Artificial Sequence
<220> FEATURE:
<223> OTHER INFORMATION: Synthetic

<400> SEQUENCE: 34
gaataccata taacccacaa agtcaaggag t                             31

<210> SEQ ID NO 35
<211> LENGTH: 32
<212> TYPE: DNA
<213> ORGANISM: Artificial Sequence
<220> FEATURE:
<223> OTHER INFORMATION: Synthetic

<400> SEQUENCE: 35
ggaataccat ataatccaca aagtcaagga gt                            32

<210> SEQ ID NO 36
<211> LENGTH: 32
<212> TYPE: DNA
<213> ORGANISM: Artificial Sequence
<220> FEATURE:
<223> OTHER INFORMATION: Synthetic

<400> SEQUENCE: 36
ggaataccat ataacccaca aagtcaagga gt                            32

<210> SEQ ID NO 37
<211> LENGTH: 24
<212> TYPE: DNA
<213> ORGANISM: Artificial Sequence
<220> FEATURE:

<223> OTHER INFORMATION: Synthetic

<400> SEQUENCE: 37
ttcccctgca ctgtaccccc caat                                                24

<210> SEQ ID NO 38
<211> LENGTH: 24
<212> TYPE: DNA
<213> ORGANISM: Artificial Sequence
<220> FEATURE:
<223> OTHER INFORMATION: Synthetic

<400> SEQUENCE: 38
tcccctgcac tgtaccccccc aatc                                               24

<210> SEQ ID NO 39
<211> LENGTH: 30
<212> TYPE: DNA
<213> ORGANISM: Artificial Sequence
<220> FEATURE:
<223> OTHER INFORMATION: Synthetic

<400> SEQUENCE: 39
gtctactatt ctttcccctg cactgtaccc                                          30

<210> SEQ ID NO 40
<211> LENGTH: 31
<212> TYPE: DNA
<213> ORGANISM: Artificial Sequence
<220> FEATURE:
<223> OTHER INFORMATION: Synthetic

<400> SEQUENCE: 40
attatgtcta ctattctttc ccctgcactg t                                        31

<210> SEQ ID NO 41
<211> LENGTH: 32
<212> TYPE: DNA
<213> ORGANISM: Artificial Sequence
<220> FEATURE:
<223> OTHER INFORMATION: Synthetic

<400> SEQUENCE: 41
gtctgttgct attatgtcta ctattctttc cc                                       32

<210> SEQ ID NO 42
<211> LENGTH: 29
<212> TYPE: DNA
<213> ORGANISM: Artificial Sequence
<220> FEATURE:
<223> OTHER INFORMATION: Synthetic

<400> SEQUENCE: 42
atttctgctg tccctgtaat aaacccgaa                                           29

<210> SEQ ID NO 43
<211> LENGTH: 45
<212> TYPE: DNA
<213> ORGANISM: Artificial Sequence
<220> FEATURE:
<223> OTHER INFORMATION: Synthetic

<400> SEQUENCE: 43
gtgtgtgccc gtctgttgtg tgactctggt aactagagat ccctc                         45

```
<210> SEQ ID NO 44
<211> LENGTH: 23
<212> TYPE: DNA
<213> ORGANISM: Artificial Sequence
<220> FEATURE:
<223> OTHER INFORMATION: Synthetic

<400> SEQUENCE: 44
cugguaacta gagaucccuc aga                                              23

<210> SEQ ID NO 45
<211> LENGTH: 26
<212> TYPE: DNA
<213> ORGANISM: Artificial Sequence
<220> FEATURE:
<223> OTHER INFORMATION: Synthetic

<400> SEQUENCE: 45
actctggtaa ctagagatcc ctcaga                                           26

<210> SEQ ID NO 46
<211> LENGTH: 27
<212> TYPE: DNA
<213> ORGANISM: Artificial Sequence
<220> FEATURE:
<223> OTHER INFORMATION: Synthetic

<400> SEQUENCE: 46
tcagcaagcc gagtcctgcg tcgagag                                          27

<210> SEQ ID NO 47
<211> LENGTH: 25
<212> TYPE: DNA
<213> ORGANISM: Artificial Sequence
<220> FEATURE:
<223> OTHER INFORMATION: Synthetic

<400> SEQUENCE: 47
cccgttgcgt cggaggtttt cttcc                                            25

<210> SEQ ID NO 48
<211> LENGTH: 28
<212> TYPE: DNA
<213> ORGANISM: Artificial Sequence
<220> FEATURE:
<223> OTHER INFORMATION: Synthetic

<400> SEQUENCE: 48
aatctctagc agtggcgccc gaacaggg                                         28

<210> SEQ ID NO 49
<211> LENGTH: 27
<212> TYPE: DNA
<213> ORGANISM: Artificial Sequence
<220> FEATURE:
<223> OTHER INFORMATION: Synthetic

<400> SEQUENCE: 49
aatctctagc agtggcgccc gaacagg                                          27

<210> SEQ ID NO 50
<211> LENGTH: 27
<212> TYPE: DNA
<213> ORGANISM: Artificial Sequence
<220> FEATURE:
<223> OTHER INFORMATION: Synthetic
```

```
<400> SEQUENCE: 50
tgacgctctc gcacccatct ctctcct                                             27

<210> SEQ ID NO 51
<211> LENGTH: 28
<212> TYPE: DNA
<213> ORGANISM: Artificial Sequence
<220> FEATURE:
<223> OTHER INFORMATION: Synthetic

<400> SEQUENCE: 51
tctctcgacg caggactcgg cttgctga                                            28

<210> SEQ ID NO 52
<211> LENGTH: 28
<212> TYPE: DNA
<213> ORGANISM: Artificial Sequence
<220> FEATURE:
<223> OTHER INFORMATION: Synthetic

<400> SEQUENCE: 52
aagaaaacct ccgacgcaac gggctcgg                                            28

<210> SEQ ID NO 53
<211> LENGTH: 25
<212> TYPE: DNA
<213> ORGANISM: Artificial Sequence
<220> FEATURE:
<223> OTHER INFORMATION: Synthetic

<400> SEQUENCE: 53
ttggcagctt cactttctct tgcag                                               25

<210> SEQ ID NO 54
<211> LENGTH: 26
<212> TYPE: DNA
<213> ORGANISM: Artificial Sequence
<220> FEATURE:
<223> OTHER INFORMATION: Synthetic

<400> SEQUENCE: 54
agttggcagc ttcactttct cttgca                                              26
```

ASSAY FOR DETECTING HUMAN IMMUNODEFICIENCY VIRUS (HIV)

CROSS-REFERENCE TO RELATED APPLICATIONS

This application claims the benefit of U.S. Provisional Patent Application No. 62/567,655, filed Oct. 3, 2017, which is incorporated by reference herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 10,075 Byte ASCII (Text) file named "36072US2ORD_ST25.txt," created on Oct. 2, 2018.

BACKGROUND OF THE INVENTION

Human Immunodeficiency Virus (HIV) is the etiologic agent of Acquired Immunodeficiency Syndrome (AIDS) (Barre-Sinoussi et al., *Science*, 220: 868-871 (1983); Popovic et al., *Science*, 224: 497-500 (1984); and Gallo et al., *Science*, 224: 500-503 (1984)). HIV can be transmitted through sexual contact, exposure to infected blood or blood products, or from an infected mother to the fetus (Curran et al., *Science*, 239: 610-616 (1988)). There are two main types of HIV: HIV-1 and HIV-2. Worldwide, HIV-1 is the predominant type of HIV, accounting for about 95% of all infections worldwide. The relatively uncommon HIV-2 virus is concentrated in West Africa, but has been seen in other countries. HIV-2 is less infectious and progresses more slowly than HIV-1, resulting in fewer deaths. HIV-2 is estimated to be more than 55% genetically distinct from HIV-1 (see, e.g., Campbell-Yesufu, O. T., and R. T. Ghandi, *Clin. Infect. Dis.*, 52(6): 780-7 (2011); and Nyamweya et al., *Rev. Med. Virol.*, 23(4): 221-40 (2013)).

Acute HIV syndrome, characterized by flu-like symptoms, develops three to five weeks after initial infection and is associated with high levels of viremia (Daar et al., *New Engl. J. Med.*, 324: 961-964 (1991); and Clark et al., *New Engl. J. Med.*, 324: 954-960 (1991)). Within four to six weeks of the onset of symptoms, HIV specific immune response is detectable (Albert et al., *AIDS*, 4:107-112 (1990); and Horsburgh et al., *Lancet*, 334: 637-640 (1989)). After seroconversion, viral load in peripheral blood declines and most patients enter an asymptomatic phase that can last for years (Pantaleo et al., *New Engl. J Med.*, 328: 327-335 (1993)). Quantitative measurement of HIV levels in peripheral blood has greatly contributed to the understanding of the pathogenesis of HIV infection (Hoe et al., *Nature*, 373: 123-126 (1995); and Wei et al., *Nature*, 373: 117-122 (1995)) and has been shown to be an essential parameter in prognosis and management of HIV infected individuals (Mellors et al., *Science*, 272: 1167-1170 (1996); Mellors et al., *Ann. Intern. Med.*, 126(12): 946-54 (1997); Chene et al., *Lancet*, 362: 679-86 (2003); Egger et al., *Lancet*, 360: 119-29 (2002); Wood et al., *J. Infect. Dis.*, 188: 1421-1425 (2003); and U.S. Department of Health and Human Services, Guidelines for the Use of Antiretroviral Agents in HIV-1 Infected Adults and Adolescents (July 2016)). Decisions regarding initiation or changes in antiretroviral therapy are guided by monitoring plasma HIV RNA levels (viral load), CD4+ T cell count, and the patient's clinical condition (U.S. Department of Health and Human Services, Guidelines for the Use of Antiretroviral Agents in HIV-1 Infected Adults and Adolescents (July 2016); and Yeni et al., *JAMA*, 292: 251-265 (2004)). The goal of antiretroviral therapy is to reduce the HIV virus in plasma to below detectable levels of available viral load tests (U.S. Department of Health and Human Services, Guidelines for the Use of Antiretroviral Agents in HIV-1 Infected Adults and Adolescents (July 2016; Perelson et al., *Nature*, 387(6629): 188-191 (1997)). HIV RNA levels in plasma can be quantitated by nucleic acid amplification or signal amplification technologies (Mulder et al., *Clin. Microbiol.*, 32: 292-300 (1994); Dewar et al., *J Inf. Diseases*, 170: 1172-9 (1994); and Van Gemen et al., *J. Virol. Methods*, 43: 177-87 (1993)).

Many existing nucleic acid tests (NATs) for HIV utilize a single probe to detect and quantify HIV RNA. Due to the high rate of mutation of HIV, however, such single-probe detection methods can result in underquantification or lack of detection of some rare HIV variants due to accumulated mutations within the target region. Nucleic acid tests also are typically performed using PCR reagents provided in liquid format that require frozen storage and batch testing, and turn around-time for sample preparation and real-time PCR can exceed several hours for some tests.

Thus, there remains a need for more reliable HIV detection methods and systems that are provided in a format that eliminates or reduces storage requirements and PCR reagent waste and are performed quickly. The present disclosure provides such methods and systems.

BRIEF SUMMARY OF THE INVENTION

The present disclosure provides a set of oligonucleotide sequences for amplifying and detecting one or more human immunodeficiency virus-1 (HIV-1) nucleic acid sequences in a sample, which comprises: (a) a primer and probe set that amplifies and detects at least a portion of the HIV-1 integrase (INT) gene comprising a forward primer oligonucleotide sequence comprising SEQ ID NO: 1, a reverse primer oligonucleotide sequence comprising SEQ ID NO: 2, and a probe oligonucleotide sequence, and (b) a primer and probe set that amplifies and detects at least a portion of the HIV-1 long terminal repeat (LTR) region, which comprises a forward primer oligonucleotide sequence comprising SEQ ID NO: 5, a reverse primer oligonucleotide sequence comprising SEQ ID NO: 6, a first probe oligonucleotide sequence, and a second probe oligonucleotide sequence, wherein each of the probe oligonucleotide sequences comprises a detectable label and/or a quencher moiety. Also provided is a method for detecting HIV-1 in a sample using the aforementioned set of oligonucleotides.

The disclosure also provides a kit for detecting human immunodeficiency virus-1 (HIV-1) in a sample comprising: (a) a primer and probe set that amplifies and detects at least a portion of the HIV-1 integrase (INT) gene comprising a forward primer oligonucleotide sequence comprising SEQ ID NO: 1, a reverse primer oligonucleotide sequence comprising SEQ ID NO: 2, and a probe oligonucleotide sequence, and (b) a primer and probe set that amplifies and detects at least a portion of the HIV-1 long terminal repeat (LTR) region, which comprises a forward primer oligonucleotide sequence comprising SEQ ID NO: 5, a reverse primer oligonucleotide sequence comprising SEQ ID NO: 6, a first probe oligonucleotide sequence, and a second probe oligonucleotide sequence, (c) reagents for amplifying and detecting nucleic acid sequences; and (d) instructions for use, wherein each of the probe oligonucleotide sequences comprises a detectable label and/or a quencher moiety.

The disclosure provides a composition for detecting a human immunodeficiency virus-1 (HIV-1) in a sample comprising: (a) a primer and probe set that amplifies and detects at least a portion of the HIV-1 integrase (INT) gene comprising a forward primer oligonucleotide sequence comprising SEQ ID NO: 1, a reverse primer oligonucleotide sequence comprising SEQ ID NO: 2, and a probe oligonucleotide sequence, and (b) a primer and probe set that amplifies and detects at least a portion of the HIV-1 long terminal repeat (LTR) region, which comprises a forward primer oligonucleotide sequence comprising SEQ ID NO: 5, a reverse primer oligonucleotide sequence comprising SEQ ID NO: 6, a first probe oligonucleotide sequence, and a second probe oligonucleotide sequence.

DETAILED DESCRIPTION OF THE INVENTION

Figure 1:
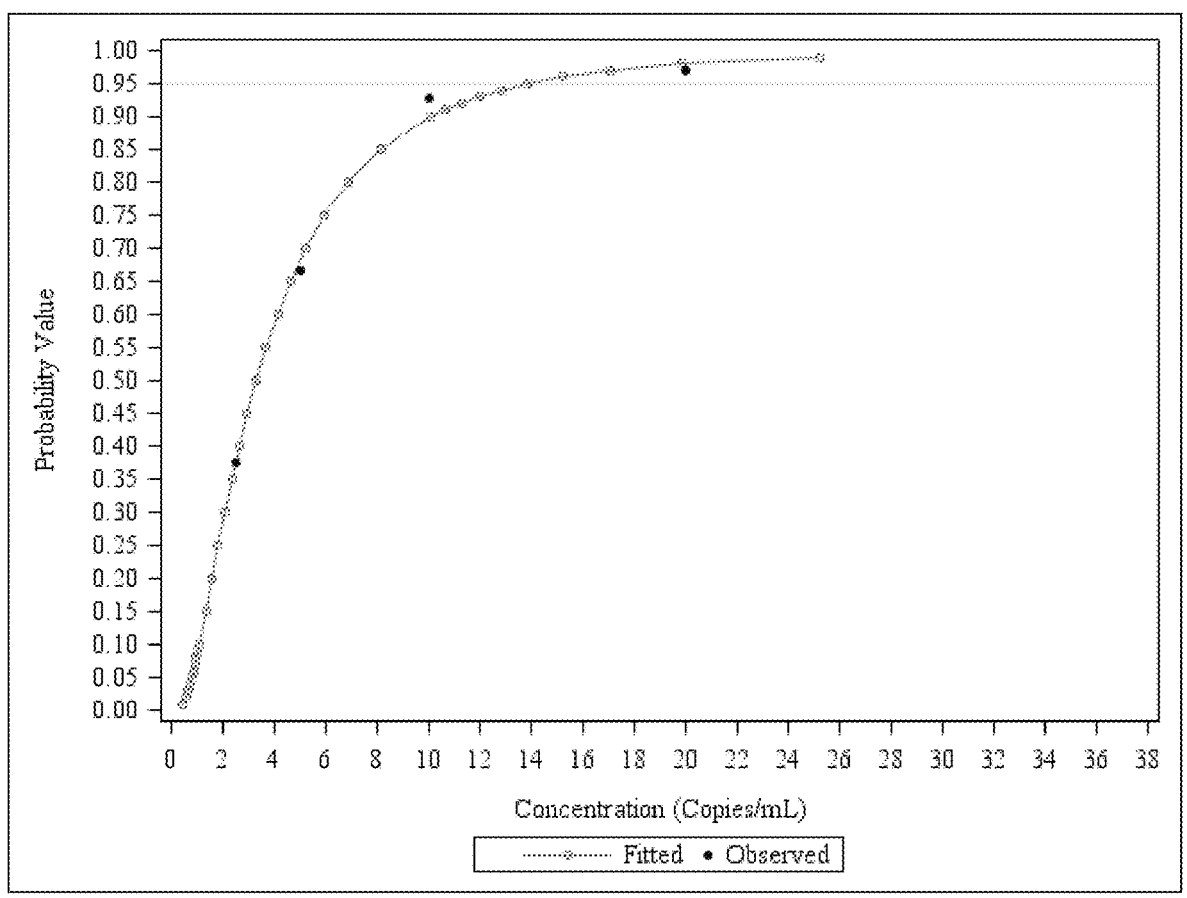
FIG. 1 is a graph illustrating ALINITY m™ HIV-1 limit of detection (LOD), plotting observed and fitted probabilities versus concentration for all lots combined.

The present disclosure provides a set of oligonucleotides for amplifying and detecting human immunodeficiency virus-1 (HIV-1) in a sample. The term "oligonucleotide," as used herein, refers to a short nucleic acid sequence comprising from about 2 to about 100 nucleotides (e.g., about 5, 10, 15, 20, 25, 30, 35, 40, 45, 50, 55, 60, 65, 70, 75, 80, 85, 90, 95, 99, or 100 nucleotides, or a range defined by any of the foregoing values). The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, for example, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

Oligonucleotides can be single-stranded or double-stranded, or can contain portions of both double-stranded and single-stranded sequences. The oligonucleotide can be DNA, both genomic and complimentary DNA (cDNA), RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Oligonucleotides can be obtained by chemical synthesis methods or by recombinant methods. A particular oligonucleotide sequence can encompass conservatively modified variants thereof (e.g., codon substitutions), alleles, orthologs, single nucleotide polymorphisms (SNPs), and complementary sequences as well as the sequence explicitly indicated.

Primer and Probe Oligonucleotides

Oligonucleotides are used in a variety of applications in biotechnology, such as, for example, artificial gene synthesis, as polymerase chain reaction (PCR) primers, in DNA sequencing, and as molecular probes. In one embodiment, the oligonucleotides described herein may be used as primers for nucleic acid amplification or as probes for nucleic acid hybridization and detection. The terms "primer," "primer sequence," and "primer oligonucleotide," as used herein, refer to an oligonucleotide which is capable of acting as a point of initiation of synthesis of a primer extension product that is a complementary strand of nucleic acid (all types of DNA or RNA), when placed under suitable amplification conditions (e.g., buffer, salt, temperature and pH) in the presence of nucleotides and an agent for nucleic acid polymerization (e.g., a DNA-dependent or RNA-dependent polymerase). A primer can be single-stranded or double-stranded. If double-stranded, the primer may first be treated (e.g., denatured) to allow separation of its strands before being used to prepare extension products. Such a denaturation step is typically performed using heat, but may alternatively be carried out using alkali, followed by neutralization. The primers of the present disclosure can be of any suitable size, and desirably comprise, consist essentially of, or consist of about 15 to 50 nucleotides, about 20 to 40 nucleotides, or about 22 to 30 nucleotides. The primers of the present disclosure can contain additional nucleotides in addition to those described herein. For example, depending on the type of amplification process employed, primers can include, for example, a restriction endonuclease recognition site 5' to the target binding sequence (see, e.g., U.S. Pat. Nos. 5,270,184 and 5,455,166), or an RNA polymerase promoter linked to the target binding sequence of the primer. A "forward primer" is a primer that hybridizes (or anneals) to a target nucleic acid sequence (e.g., template strand) for amplification. A "reverse primer" is a primer that hybridizes (or anneals) to the complementary strand of the target sequence during amplification. A forward primer hybridizes with a target sequence 5' with respect to a reverse primer.

The terms "probe," "probe sequence," and "probe oligonucleotide," refer to an oligonucleotide that can selectively hybridize to at least a portion of a target sequence under appropriate amplification conditions (e.g., a portion of a target sequence that has been amplified). In general, a probe sequence is identified as being either "complementary" (i.e., complementary to the coding or sense strand (+)), or "reverse complementary" (i.e., complementary to the antisense strand (−)). A probe can be single-stranded or double-stranded. If double-stranded, a probe oligonucleotide sequence comprises a first nucleic acid sequence comprising a detectable label and a second nucleic acid sequence comprising a quencher moiety, as described in U.S. Pat. No. 9,388,455. The probes of the present disclosure can be of any suitable size, and desirably comprise, consist essentially of, or consist of about 10-50 nucleotides, about 12-35 nucleotides, or about 14-25 nucleotides.

As used herein, the terms "set," "primer set," "probe set," and "primer and probe set," refer to two or more oligonucleotide primers which together are capable of priming the amplification of a target sequence or target nucleic acid of interest (e.g., a target sequence within HIV-1) and/or at least one probe which can detect the target sequence or target nucleic acid. In certain embodiments, the term "primer set" refers to a pair of primers including a forward primer (or 5' (upstream) primer) that hybridizes with the 5'-end of the target sequence or target nucleic acid to be amplified and a reverse primer (or 3' (downstream) primer) that hybridizes with the complement of the target sequence or target nucleic acid to be amplified. Such primer sets or primer pairs are particularly useful in PCR amplification reactions.

The set of oligonucleotides described herein may be used to amplify and one or more target HIV-1 nucleic acid sequences in a sample. The terms "target sequence" and "target nucleic acid" are used interchangeably herein and refer to a specific nucleic acid sequence, the presence or absence of which is to be detected by the disclosed method.

In the context of the present disclosure, a target sequence preferably includes a nucleic acid sequence to which one or more primers will hybridize and from which amplification will initiate. The target sequence can also include a probe-hybridizing region with which a probe may form a stable hybrid under appropriate amplification conditions. A target sequence may be single-stranded or double-stranded, and more than one target sequence may be amplified and detected. The primer and probe sequences described herein can target any suitable nucleic acid sequence, or combination of sequences, present in the HIV-1 genome.

HIV-1 is composed of two copies of noncovalently linked, unspliced, positive-sense single-stranded RNA enclosed by a conical capsid composed of the viral protein p24, typical of lentiviruses (Montagnier, Luc., Human Immunodeficiency Viruses (Retroviridae). *Encyclopedia of Virology* (2nd Ed.), pp. 763-774 (1999); and Lu et al., *J. Mol. Biol.,* 410(4): 609-633 (2011)). The integrated form of HIV-1, also known as the provirus, is approximately 9.8 kilobases in length (Muesing et al., *Nature,* 313(6002): 450-458 (1985)). Both ends of the provirus are flanked by a repeated sequence known as the long terminal repeat (LTR). The HIV-1 genes are located in the central region of the proviral DNA and encode at least nine proteins (Gallo et al., *Nature,* 333 (6173): 504 (1988)), which are divided into three different classes: structural proteins, regulatory proteins, and accessory proteins. The major structural proteins include Gag, Pol, and Env, with the Gag and Pol proteins initially translated as a Gag-Pol polyprotein. Gag is a polyprotein which encodes components of the viral capsid. The Pol polyprotein encodes reverse transcriptase (RT), integrase (INT), and protease (PR), which reverse transcribes the viral RNA into double stranded DNA, integrates the viral genome into the chromosome of a host cell, and cleaves the Gag-Pol-derived proteins into functional polypeptides, respectively. Env proteins are envelope proteins involved in viral attachment and fusion to target cells. The HIV-1 regulatory proteins include Tat and Rev, and the HIV-1 accessory proteins include Vpu, Vpr, Vif, and Nef.

The set of oligonucleotides described herein may comprise, consist essentially of, or consist of any number of primer and probe oligonucleotides so as to amplify and detect any suitable number of HIV nucleic acid sequences. In one embodiment, the set of oligonucleotides described herein comprises, consists essentially of, or consists of a primer and probe set that amplifies and detects at least a portion of the HIV-1 integrase (INT) gene and a primer and probe set that amplifies and detects at least a portion of an HIV-1 long terminal repeat (LTR) region, to produce two HIV-1 amplicons. A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides. As used herein, the term "amplicon" refers to a product of a natural or artificial amplification reaction.

In one embodiment, the set of oligonucleotides described herein comprises, consists essentially of, or consists of (a) a primer and probe set that amplifies and detects at least a portion of the HIV-1 integrase (INT) gene comprising a forward primer oligonucleotide sequence comprising SEQ ID NO: 1, a reverse primer oligonucleotide sequence comprising SEQ ID NO: 2, and a probe oligonucleotide sequence, and (b) a primer and probe set that amplifies and detects at least a portion of an HIV-1 long terminal repeat (LTR) region, which comprises a forward primer oligonucleotide sequence comprising SEQ ID NO: 5, a reverse primer oligonucleotide sequence comprising SEQ ID NO: 6, a first probe oligonucleotide sequence, and a second probe oligonucleotide sequence. In one embodiment, the probe oligonucleotide of the primer and probe set that amplifies and detects a portion of the HIV-1 INT gene is double-stranded and comprises a first nucleic acid sequence comprising a detectable label and a second nucleic acid sequence comprising a quencher moiety (as described in U.S. Pat. No. 9,388,455). For example, the first nucleic acid sequence comprising a detectable label may comprise SEQ ID NO: 3, while the second nucleic acid sequence comprising a quencher moiety may comprise SEQ ID NO: 4. In another embodiment, the first and second probe oligonucleotide sequences of the primer and probe set that amplifies and detects a portion of the HIV-1 LTR region also are double-stranded and each comprises a first nucleic acid sequence comprising a detectable label and a second nucleic acid sequence comprising a quencher moiety. For example, the first probe oligonucleotide sequence may comprise the nucleic acid sequences of SEQ ID NO: 7 and SEQ ID NO: 8, and the second probe oligonucleotide sequence may comprise the nucleic acids sequences of SEQ ID NO: 9 and SEQ ID NO: 10. The foregoing set of oligonucleotides is also referred to as ALINITY m™ HIV-1.

The set of oligonucleotides described herein comprise a "dual-target" design, in contrast to other commercially available HIV-1 nucleic acid tests which detect and quantify a single HIV-1 target sequence (e.g. the Abbott REALTIME HIV-1 assay (Abbott Molecular, Inc., Des Plaines, Ill.; and the XPERT® HIV-1 Viral Load Assay (Cepheid, Sunnyvale, Calif.)). The turnaround time for sample preparation and real-time PCR for such "single-target" detection systems can exceed six hours in some instances. In contrast, the set of oligonucleotides described herein allows for sample-to-result analysis in approximately two hours. In addition, as discussed above, the set of oligonucleotides described herein enhances reliability of HIV-1 detection, as the set amplifies and detects two separate regions of the HIV-1 genome instead of a single region.

Alternatively or additionally, the primer and probe set that amplifies and detects a portion of the HIV-1 INT gene may comprise a forward primer oligonucleotide sequence comprising, consisting essentially of, or consisting of any one of the following sequences: SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, or SEQ ID NO: 36. Likewise, the primer and probe set that amplifies and detects a portion of the HIV-1 INT gene may alternatively or additionally comprise a reverse primer oligonucleotide sequence comprising, consisting essentially of, or consisting of any one of the following sequences: SEQ ID NO: 37, SEQ ID NO: 38, SEQ ID NO: 39, SEQ ID NO:40, SEQ ID NO:41, or SEQ ID NO: 42.

Alternatively or additionally, the first or second probe oligonucleotide of the primer and probe set that amplifies and detects a portion of the HIV-1 LTR may comprise SEQ ID NO: 43 and/or SEQ ID NO: 44. In another embodiment, the primer and probe set that amplifies and detects a portion of the HIV-1 LTR region may comprise, consist essentially of, or consist of a forward primer oligonucleotide sequence comprising SEQ ID NO: 45, a first reverse primer oligonucleotide sequence comprising SEQ ID NO: 46, a second reverse primer oligonucleotide sequence comprising SEQ ID NO: 47, and a probe oligonucleotide sequence comprising SEQ ID NO: 48. In yet another alternative, the primer and probe set that amplifies and detects a portion of the HIV-1 LTR region comprises, consists essentially of, or consists of a forward primer oligonucleotide sequence comprising SEQ ID NO: 49, a reverse primer oligonucleotide sequence comprising SEQ ID NO: 50, a first probe oligonucleotide sequence comprising SEQ ID NO: 51, and a second probe oligonucleotide sequence comprising SEQ ID NO: 52.

Any one or combination of the oligonucleotides described herein may be modified in any suitable manner so as to stabilize or enhance the binding affinity (also referred to as "melting temperature" or "$T_m$") of a primer or probe oligonucleotide for its target. In this respect, an oligonucleotide sequence as described herein may comprise one or more modified oligonucleotide bases. For example, the oligonucleotide sequence may comprise one or more propyne-modified bases, wherein the oligonucleotide comprises an alkyne with the chemical formula $CH_3C\equiv CH$. The one or more propyne-modified bases may include, for example, 5-(1-propynyl)-2'-deoxy-Uridine (pdU) and/or 5-(1-propynyl)-2'-deoxyCytidine (pdC).

Any one of the oligonucleotide sequences described herein may comprise, consist essentially of, or consist of a complement of any of the sequences disclosed herein. The terms "complement" or "complementary sequence," as used herein, refer to a nucleic acid sequence that forms a stable duplex with an oligonucleotide described herein via Watson-Crick base pairing rules, and typically shares about 80%, about 81%, about 82%, about 83%, about 84%, about 85%, about 86%, about 87%, about 88%, about 89%, about 90%, about 91%, about 92%, about 93%, about 94% about 95%, about 96%, about 97%, about 98% or about 99% greater identity with the disclosed oligonucleotide. Nucleic acid sequence identity can be determined using any suitable mathematical algorithm or computer software known in the art, such as, for example, CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.*, 215(3): 403-410 (1990); Beigert et al., *Proc. Natl. Acad. Sci. USA*, 106(10): 3770-3775 (2009), Durbin et al., eds., *Biological Sequence Analysis: Probabilstic Models of Proteins and Nucleic Acids*, Cambridge University Press, Cambridge, UK (2009); Soding, *Bioinformatics*, 21(7): 951-960 (2005); Altschul et al., *Nucleic Acids Res.*, 25(17): 3389-3402 (1997); and Gusfield, *Algorithms on Strings, Trees and Sequences*, Cambridge University Press, Cambridge UK (1997)).

The oligonucleotides described herein may be prepared using any suitable method, a variety of which are known in the art (see, for example, Sambrook et al., *Molecular Cloning. A Laboratory Manual*, 1989, 2. Supp. Ed., Cold Spring Harbour Laboratory Press: New York, N.Y.; M. A. Innis (Ed.), *PCR Protocols. A Guide to Methods and Applications*, Academic Press: New York, N.Y. (1990); P. Tijssen, *Hybridization with Nucleic Acid Probes—Laboratory Techniques in Biochemistry and Molecular Biology (Parts I and II)*, Elsevier Science (1993); M. A. Innis (Ed.), *PCR Strategies*, Academic Press: New York, N.Y. (1995); F. M. Ausubel (Ed.), *Short Protocols in Molecular Biology*, John Wiley & Sons: Secaucus, N.J. (2002); Narang et al., *Meth. Enzymol.*, 68: 90-98 (1979); Brown et al., *Meth. Enzymol.*, 68: 109-151 (1979); and Belousov et al., *Nucleic Acids Res.*, 25: 3440-3444 (1997)). Primer pairs also can be designed using a variety of tools, such as the Primer-BLAST tool provided by the National Center of Biotechnology Information (NCBI). Oligonucleotide synthesis may be performed on oligo synthesizers such as those commercially available from Perkin Elmer/Applied Biosystems, Inc. (Foster City, Calif.), DuPont (Wilmington, Del.), or Milligen (Bedford, Mass.). Alternatively, oligonucleotides can be custom made and obtained from a variety of commercial sources well-known in the art, including, for example, the Midland Certified Reagent Company (Midland, Tex.), Eurofins Scientific (Louisville, Ky.), BioSearch Technologies, Inc. (Novato, Calif.), and the like. Oligonucleotides may be purified using any suitable method known in the art, such as, for example, native acrylamide gel electrophoresis, anion-exchange HPLC (see, e.g., Pearson et al., *J. Chrom.*, 255: 137-149 (1983)), and reverse phase HPLC (see, e.g., McFarland et al., *Nucleic Acids Res.*, 7: 1067-1080 (1979)).

The sequence of the primers and probes can be verified using any suitable sequencing method known in the art, including, but not limited to, chemical degradation (see, e.g., Maxam et al., *Methods of Enzymology*, 65: 499-560 (1980)), matrix-assisted laser desorption ionization time-of-flight (MALDI-TOF) mass spectrometry (see, e.g., Pieles et al., Nucleic Acids Res., 21: 3191-3196 (1993)), mass spectrometry following a combination of alkaline phosphatase and exonuclease digestions (Wu et al. Anal. Biochem., 290: 347-352 (2001)), and the like.

The primer and probe oligonucleotides described herein desirably comprise a melting temperature ($T_M$) in the range 45° C. to 80° C. In accordance with the present disclosure, the oligonucleotides specifically hybridize to a target HIV-1 nucleic acid sequence without exhibiting significant hybridization to non-HIV-1 nucleic acids. In addition, the oligonucleotides are selected such that they hybridize to conserved regions in the HIV-1 genome, thus minimizing mismatches with the target sequence. This selection ensures that the oligonucleotides are capable of hybridizing to HIV-1 nucleic acids from all groups and subtypes. Furthermore, the oligonucleotides are selected such that they show the least likelihood of dimer formation and contain minimal sequence repeats. Such properties can be determined by methods known in the art, for example, using the computer modelling program OLIGO® Primer Analysis Software (distributed by National Biosciences, Inc., Plymouth, Minn.).

Detectable Label

Any one or more of the primer and probe oligonucleotide sequences described herein may comprise a detectable label, such that the primer and/or probe can be visualized, following binding to another entity (e.g., an amplification product or amplicon). The term "detectable label," as used herein, refers to a moiety or compound that generates a signal which can be measured and whose intensity is related to (e.g., proportional to) the amount of entity bound thereto. Any suitable detectable label that can be conjugated or linked to an oligonucleotide in order to detect binding of the oligonucleotide to a target sequence can be used, many of which are known in the art. In one embodiment, the detectable label may be detected indirectly. Indirectly detectable labels are typically specific binding members used in conjunction with a "conjugate" that is attached or coupled to a directly detectable label. Coupling chemistries for synthesizing such conjugates are well-known in the art and are designed such that the specific binding property of the specific binding member and the detectable property of the label remain intact. As used herein, "specific binding member" and "conjugate" refer to the two members of a binding pair, i.e. two different molecules, where the specific binding member binds specifically to the polynucleotide of the present disclosure, and the "conjugate" specifically binds to the specific binding member. Binding between the two members of the pair is typically chemical or physical in nature. Examples of such binding pairs include, but are not limited to, antigens and antibodies, avidin/streptavidin and biotin, haptens and antibodies specific for haptens, complementary nucleotide sequences, enzyme cofactors/substrates and enzymes, and the like.

In another embodiment, the detectable label may be directly detected. Such directly detectable labels include, for example, radioisotopes, fluorophores, chemiluminophores, enzymes, colloidal particles, fluorescent microparticles, intercalating dyes (e.g., SYBR Green or ethidium bromide), and the like. In one embodiment, the detectable label may be a fluorophore, such as a fluorescein-family dye, polyhalofluorescein-family dye, hexachlorofluorescein-family dye, coumarin-family dye, rhodamine-family dye, cyanine-family dye, oxazine-family dye, thiazin-family dye, squaraine-family dye, chelated lanthanide-family dye, azo-family dye, triphenylmethane-family dye, or a BODIPY®-family dye. Examples of fluorophores include, but are not limited to, FAM™, HEX™, JOE™, NED™, PET®, ROX™, TAMRA™, TET™, TEXAS RED®, and VIC®. One skilled in the art will appreciate that directly detectable labels may require additional components, such as substrates, triggering reagents, light, and the like, to enable detection of the label. Methods for labeling oligonucleotides, such as probes, are well-known in the art and described in, e.g., L. J. Kricka, *Ann. Clin. Biochem.*, 39: 114-129 (2002); van Gijlswijk et al., *Expert Rev. Mol. Diagn.*, 1: 81-91 (2001); Joos et al., *J. Biotechnol.*, 35: 135-153 (1994); Smith et al., *Nucl. Acids Res.*, 13: 2399-2412 (1985); Connoly et al., *Nucl. Acids. Res.*, 13: 4485-4502 (1985); Broker et al., *Nucl. Acids Res.*, 5: 363-384 (1978); Bayer et al., *Methods of Biochem. Analysis*, 26: 1-45 (1980); Langer et al., *Proc. Natl. Acad. Sci. USA*, 78: 6633-6637 (1981); Richardson et al., *Nucl. Acids Res.*, 11: 6167-6184 (1983); Brigati et al., *Virol.*, 126: 32-50 (1983); Tchen et al., *Proc. Natl. Acad. Sci. USA*, 81: 3466-3470 (1984); Landegent et al., *Exp. Cell Res.*, 15: 61-72 (1984); A. H. Hopman et al., *Exp. Cell Res.*, 169: 357-368 (1987); and Temsamani et al., *Mol. Biotechnol.*, 5: 223-232 (1996).

In another embodiment, any one or more of the primer and probe oligonucleotide sequences described herein may also comprise a quencher moiety. When a detectable label (e.g., a fluorophore) and quencher moiety are held in close proximity, such as at the ends of a probe, the quencher moiety prevents detection of a signal (e.g., fluorescence) from the detectable label. When the two moieties are physically separated, such as after cleavage by a DNA polymerase, the signal becomes detectable. The quencher may be selected from any suitable quencher known in the art, such as, for example, BLACK HOLE QUENCHER® 1 (BHQ-1®), BLACK HOLE QUENCHER® 2 (BHQ-2®), BLACK HOLE QUENCHER®-1-dT (BHQ-1dT®), BLACK HOLE QUENCHER®-2-dT (BHQ-2dT®), IOWA BLACK® FQ, and IOWA BLACK® RQ. For example, an oligonucleotide probe may comprise a FAM fluorophore and a BHQ-1dT® quencher or a BHQ-2dT® quencher.

Each of the probe oligonucleotide sequences in the set of oligonucleotide sequences for amplifying and detecting an HIV-1 nucleic acid sequence described herein desirably comprises a detectable label. Each of the probes may be labeled with the same detectable label or different detectable labels. When the probes comprise the same detectable label (e.g., FAM), amplification of the portion of the HIV INT gene and the LTR region are detected as a single signal during real-time PCR. When each probe comprises a different detectable label, amplification of the HIV INT gene and the LTR region are detected as two separate signals.

The selection of a particular labeling technique will depend on several factors, such as the ease and cost of the labeling method, spectral spacing between different detectable labels used, the quality of sample labeling desired, the effects of the detectable moiety on the hybridization reaction (e.g., on the rate and/or efficiency of the hybridization process), the nature of the amplification method used, the nature of the detection system, the nature and intensity of the signal generated by the detectable label, and the like.

Internal Control

The set of oligonucleotides for detecting HIV-1 described herein may further comprise primer and probe oligonucleotide sequences for amplifying and detecting an internal control (IC) sequence. In one embodiment, the internal control sequences are added to each sample preparation reaction. The internal control is then processed through the entire sample preparation and amplification procedure along with the test samples and calibrators (if present), to demonstrate proper sample processing and assay validity. The internal control may be any suitable non-HIV nucleic acid sequence, including, for example, a nucleic acid sequence encoding GAPDH, beta2-microglobulin, beta-actin, R18, or 16S RNA. In some embodiments, the internal control desirably comprises, consists essentially of, or consists of an armored RNA target sequence. The term "armored RNA," as used herein, refers to RNase-resistant RNA that is a complex of MS2 bacteriophage coat protein and RNA produced in *Escherichia coli* by the induction of an expression plasmid that encodes the coat protein and an RNA standard sequence (see, e.g., Pasloske et al., *J. Clin. Microbiol.*, 36(12): 3590-359 (1998); and U.S. Pat. Nos. 5,677,124, 5,919,625, and 5,939,262). In one embodiment, for example, the internal control may comprise an RNA sequence derived or obtained from the hydroxypyruvate reductase gene of the pumpkin plant, *Curcurbita pepo*. In this regard, the set of oligonucleotides described herein may further comprise an internal control forward primer oligonucleotide sequence comprising SEQ ID NO: 11, SEQ ID NO: 53, or SEQ ID NO: 54, an internal control reverse primer oligonucleotide sequence comprising SEQ ID NO: 12, and an internal control probe oligonucleotide sequence comprising SEQ ID NO: 13. The internal control probe desirably comprises a detectable label, such as any of those described herein. In one embodiment, the internal control probe may comprise a different label than the probes used to detect HIV-1, which allows for simultaneous detection and differentiation of internal control and HIV-amplified products within the same reaction. The internal control probe may also comprise a quencher moiety, such as any of those described herein.

Method for Amplifying and Detecting HIV-1

The present disclosure provides a method for detecting a human immunodeficiency virus-1 (HIV-1) in a sample suspected of containing HIV-1. The method comprises: (a) contacting a sample obtained from a human with the set of oligonucleotide sequences described herein and reagents for amplification and detection of nucleic acid sequences, (b) amplifying a portion of the HIV-1 INT gene and a portion of the HIV-1 LTR present in the sample, hybridizing the probe oligonucleotide that detects a portion of the HIV-1 INT gene to the amplified portion of the HIV-1 INT gene, and/or hybridizing the first and second probe oligonucleotide sequences that detect a portion of the HIV-1 LTR region to the amplified portion of the HIV-1 LTR region, (d) detecting hybridization of the probe oligonucleotide sequences to the portions of the HIV-1 INT gene and/or LTR region by assessing a signal from each of the detectable labels, whereby (i) the presence of the signal from the detectable label on the probe oligonucleotide sequence that detects at least a portion of the HIV-1 INT gene indicates hybridization of the probe oligonucleotide sequence to the portion of the HIV-1 INT gene and the presence of HIV-1 in the sample; and/or (ii) the presence of a signal from the first probe oligonucleotide sequence and/or the second probe oligonucleotide sequence indicates hybridization of the first probe oligonucleotide sequence and/or second probe oligonucleotide sequence to the portion of the LTR region and the presence of HIV-1 in the sample, and (iii) the absence of the signals indicates the absence of HIV-1 in the sample. Descriptions of the primer and probe oligonucleotides set forth herein with respect to the aforementioned set of oligonucleotides also are applicable to those same aspects of the disclosed method.

A sample, as defined herein, is "suspected" of containing HIV-1 if the sample is obtained from a subject, preferably a human, suspected of being infected with HIV-1. A subject is suspected of being infected with HIV-1 if the subject has an increased risk for HIV-1. Risk factors for HIV-1 infection include, for example, having unprotected sex, infection with another sexually transmitted disease (STD), intravenous drug use, being an uncircumcised male, being a gay or bisexual male, and receiving blood transfusions (see, e.g., Global Fact Sheet: HIV/AIDS I. HIV/AIDS Basics, 20th International AIDS Conference (2014)).

The sample can be any suitable sample obtained from any suitable subject, typically a mammal, such as a human. The sample may be obtained from any biological source, such as, a cervical, vaginal, or anal swab or brush, or a physiological fluid including, but not limited to, whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and the like. The sample can be obtained from the subject using routine techniques known to those skilled in the art, and the sample may be used directly as obtained from the biological source or following a pretreatment to modify the character of the sample. Such pretreatment may include, for example, preparing plasma from blood, diluting viscous fluids, filtration, precipitation, dilution, distillation, mixing, concentration, inactivation of interfering components, the addition of reagents, lysing, etc. After the sample is obtained from a subject, the sample may be contacted with the set of oligonucleotides as described herein to form a reaction mixture. The reaction mixture is then placed under amplification conditions. The primers hybridize to a target nucleic acid sequence within the HIV-1 INT gene and/or HIV-1 LTR region if present in the sample, and the portion of the HIV-1 INT gene and/or the HIV-1 LTR region present in the sample are amplified.

Amplifying an HIV-1 nucleic acid sequence in the sample can be performed using any suitable nucleic acid sequence amplification method known in the art, including but not limited to, polymerase chain reaction (PCR), reverse-transcriptase PCR (RT-PCR), real-time PCR, transcription-mediated amplification (TMA), rolling circle amplification, nucleic acid sequence based amplification (NASBA), strand displacement amplification (SDA), and ligase chain reaction (LCR).

Because HIV-1 comprises an RNA genome, amplification of HIV-1 nucleic acid sequences desirably is performed using RT-PCR, such as, for example, real-time RT-PCR. "RT-PCR," as used herein, refers to the enzymatic reaction in which complementary DNA (cDNA) fragments are synthesized from a substrate RNA template. The reaction typically involves the use of a synthetic oligonucleotide primer, which is complementary to nucleotide sequences in the substrate RNA, and the use of a reverse transcriptase enzyme. The reaction consists of one cycle, in which the oligonucleotide primers, which are present in vast excess, hybridize to the substrate RNA to form double-stranded structures along complementary nucleotide sequences. The primer-substrate DNA:RNA complexes will then serve as initiation sites for a cDNA synthesis reaction catalyzed by reverse transcriptase, resulting in the synthesis of a cDNA strand complementary to the RNA strand. The RNA may be a messenger RNA (mRNA), transfer RNA (tRNA), genomic RNA (gRNA), ribosomal RNA (rRNA), or a small nuclear RNA (snRNA). Methods and reagents for RT-PCR well known in the art and commercially available from a variety of sources (see, e.g., Freeman et al., *Biotechniques*, 26(1): 112-122, 142-125 (1999); Joyce, C., *Methods Mol. Biol.*, 193: 83-92 (2002); and O'Connell, J. (ed.), *RT-PCR Protocols*, 1st Ed., Springer-Verlag, New York, N.Y. (2010)). Reverse transcription can be performed using one-step or two-step techniques known in the art, such as, for example, by using reverse transcription kits available from Thermo Fisher Scientific (Waltham, Mass.) Qiagen (Hilden, Germany), and Promega Corp. (Madison, Wis.).

"Real-time PCR," as used herein, refers to a PCR method in which the accumulation of amplification product is measured as the reaction progresses, in real time, with product quantification after each cycle, in contrast to conventional PCR in which the amplified DNA product is detected in an end-point analysis. Real-time PCR also is known in the art at "quantitative PCR (qPCR)." Real-time detection of PCR products typically involves the use of non-specific fluorescent dyes that intercalate with any double-stranded DNA and sequence-specific fluorescently-labeled DNA probes. Real-time PCR techniques and systems are known in the art (see, e.g., Dorak, M. Tevfik, ed. *Real-time PCR*. Taylor & Francis (2007); and Fraga et al., "Real-time PCR," Current protocols essential laboratory techniques: 10-3 (2008)) and are commercially available from a variety of sources (e.g., m2000rt REALTIME™ PCR system (Abbott Molecular, Inc., Des Plaines, Ill.); CFX Real-Time PCR Detection Systems (Bio-Rad Laboratories, Inc., Hercules, Calif.); and TAQMAN™ Real-Time PCR System (ThermoFisher Scientific, Waltham, Mass.)), any of which can be employed in the methods described herein.

Following amplification of a portion of the HIV-1 INT gene and/or a portion of the HIV-1 LTR region, if present in the sample, the method described herein further comprises hybridizing the probe oligonucleotide that detects a portion of the HIV-1 INT gene to the amplified portion of the HIV-1 INT gene and hybridizing the first and/or second probe oligonucleotide sequences that detect a portion of the HIV-1 LTR region to the amplified portion of the HIV-1 LTR region. In one embodiment, a reaction mixture comprising an HIV INT amplicon and an HIV-1 LTR amplicon may be contacted with oligonucleotide probes, as described herein, that preferentially hybridize to a target nucleic acid sequence of the amplicon, or the complement thereof, under stringent hybridization and wash conditions, thereby forming a hybrid duplex that is stable for detection. "Hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. The stringency of hybridization conditions are sequence-dependent and are different under different environmental parameters. Thus, hybridization conditions resulting in particular degrees of stringency will vary depending upon the nature of the hybridization method of choice and the composition and length of the hybridizing nucleic acid sequences. For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast nucleic acids that hybridize under "low stringency" conditions include those with much less sequence identity, or with sequence identity over only short subsequences of the nucleic acid. Stringent conditions can be selected to be lower than the thermal melting point ($T_m$) for the specific sequence at a defined ionic strength pH. The $T_m$ can be the temperature (under defined ionic strength, pH, and nucleic concentration) at which 50% of an oligonucleotide complementary to a target hybridize to the target sequence at equilibrium (as the target sequences are present in excess, at $T_m$, 50% of the probes are occupied at equilibrium). Any suitable method and conditions for hybridizing oligonucleotide probes to a target HIV nucleic acid sequence known in the art can be used in the disclosed method. Conditions for nucleic acid hybridization and calculation of stringencies can be found, for example, in Sambrook et al., Molecular Cloning: A Laboratory Manual, 4$^{th}$ Ed., Cold Spring Harbor Laboratory Press, Cold Spring Harbor, N.Y. (2012); Tijssen, Hybridization With Nucleic Acid Probes, Part I: Theory and Nucleic Acid Preparation, Laboratory Techniques in Biochemistry and Molecular Biology, Elsevier Science Ltd., NY, NY, 1993 and Ausubel et al. Short Protocols in Molecular Biology, 5th ed., John Wiley & Sons, Inc. (2002).

Following hybridization of the probe oligonucleotide that detects a portion of the HIV-1 INT gene to the amplified portion of the HIV-1 INT gene and/or hybridization of the first and second probe oligonucleotide sequences that detect a portion of the HIV-1 LTR region to the amplified portion of the HIV-1 LTR region, the method comprises detecting hybridization of the probe oligonucleotide sequences to the portions of the HIV-1 INT gene and/or LTR region by assessing a signal from each of the detectable labels, whereby (i) the presence of the signals indicates hybridization of the probe oligonucleotide sequences to the HIV-1 INT gene and/or LTR region and the presence of HIV-1 in the sample, and (ii) the absence of the signals indicates the absence of HIV-1 in the sample. Detection of signals from the probe oligonucleotide sequences may be performed using a variety of well-known methodologies, including, for example homogeneous or heterogeneous techniques.

Homogeneous detection methods involve detecting products of the amplification reaction as they are formed, namely, in a real time manner. As a result, amplification product/probe hybrids are formed and detected while the reaction mixture is under amplification conditions. Homogeneous detection methods include, but are not limited to, the use of FRET labels that are attached to the probes and that emit a signal in the presence of the target sequence, Molecular Beacons (See, Tyagi et al., *Nature Biotechnol.*, 14: 303-308 (1996); Tyagi et al., *Nature Biotechnol.*, 16: 49-53 (1998); Kostrikis et al., *Science*, 279: 1228-1229 (1998); Sokol et al., *Proc. Natl. Acad. Sci. USA*, 95: 11538-11543 (1998); Marras et al., *Genet. Anal.*, 14: 151-156 (1999); and U.S. Pat. Nos. 5,846,726, 5,925,517, 6,277,581 and 6,235,504), TAQMAN® assays (see, e.g., U.S. Pat. Nos. 5,210,015; 5,804,375; 5,487,792 and 6,214,979 and International Patent Application Publication WO 01/86001), and hybridization protection assays (HPA) which utilize probes labeled with acridinium ester (AE) (see, e.g., Weeks et al., *Clin. Chem.*, 29: 1474-1479 (1983); Berry et al., *Clin. Chem.*, 34: 2087-2090 (1988)).

Heterogeneous detection systems generally employ a capture agent to separate amplified sequences from other materials in the reaction mixture. Capture agents typically comprise a solid support material (e.g., microtiter wells, beads, chips, and the like) coated with one or more specific binding sequences. A binding sequence may be complementary to a tail sequence added to oligonucleotide probes of the disclosure. Alternatively, a binding sequence may be complementary to a sequence of a capture oligonucleotide, itself comprising a sequence complementary to a tail sequence of a probe. After separation of the amplification product/probe hybrids bound to the capture agents from the remaining reaction mixture, the amplification product/probe hybrids can be detected using any suitable detection method known in the art or described herein.

The method disclosed herein also comprises quantification of the portion of the HIV-1 INT gene and/or the portion of the HIV-1 LTR region detected as described above. In this respect, quantification of real-time PCR products can be achieved using relative quantification methods or absolute quantification methods (see, e.g., Dhanasekaran et al., *Immunol. Methods*, 354 (1-2): 34-39 (2010)). Absolute quantification provides the exact number of target DNA molecules by comparison with DNA standards using a calibration curve, and requires that the PCR of the sample and the standard have the same amplification efficiency (see, e.g., Bar et al., *Nucleic Acids Research*, 40: gkr778 (2011)). Relative quantification is based on internal reference genes to determine fold-differences in expression of a target gene. Relative quantification is expressed as the change in expression levels of the target sequence and does not require a calibration curve, as the amount of the target sequence is compared to the amount of a control reference sequence.

Kits and Compositions for Amplifying and Detecting an HIV-1 Nucleic Acid Sequence The disclosure also provides a kit for amplifying and detecting HIV-1 in a sample. The kit comprises primer and probe sets that amplify and detect a portion of the HIV-1 INT gene and/or a portion of the HIV-1 LTR region, and reagents and instructions for amplifying and detecting HIV-1. Descriptions of the primer oligonucleotides and probe oligonucleotides set forth herein with respect to the aforementioned methods also are applicable to those same aspects of the kits described herein. Examples of suitable reagents for inclusion in the kit (in addition to the oligonucleotide primers and probes described herein) include conventional reagents employed in nucleic acid amplification reactions, such as, for example, one or more enzymes having polymerase activity (e.g., reverse transcriptase), enzyme cofactors (such as magnesium or nicotinamide adenine dinucleotide (NAD)), salts, buffers, deoxyribonucleotide, or ribonucleotide triphosphates (dNTPs/rNTPs; for example, deoxyadenosine triphosphate, deoxyguanosine triphosphate, deoxycytidine triphosphate, and deoxythymidine triphosphate) blocking agents, labeling agents, a passive reference dye, preservatives (e.g., PROCLIN™), and the like. Many such reagents are described herein or otherwise known in the art and commercially available.

In one embodiment, the kit may comprise, consist essentially of, or consist of (a) a primer and probe set that amplifies and detects a portion of the HIV-1 integrase (INT) gene comprising a forward primer oligonucleotide sequence comprising SEQ ID NO: 1, a reverse primer oligonucleotide sequence comprising SEQ ID NO: 2, and a probe oligonucleotide sequence, and (b) a primer and probe set that amplifies and detects a portion of the HIV-1 long terminal repeat (LTR) region, which comprises a forward primer oligonucleotide sequence comprising SEQ ID NO: 5, a reverse primer oligonucleotide sequence comprising SEQ ID NO: 6, a first probe oligonucleotide sequence, and a second probe oligonucleotide sequence, (c) reagents for amplifying and detecting nucleic acid sequences; and (d) instructions for use, wherein each of the probe oligonucleotide sequences comprises a detectable label and/or a quencher moiety.

The kit may comprise instructions for using the amplification reagents and primer and probe oligonucleotides described herein, e.g., for processing the test sample, extracting nucleic acid molecules, and/or performing the test; and for interpreting the results obtained, as well as a notice in the form prescribed by a governmental agency. Such instructions optionally can be in printed form, provided on-line, on CD, DVD, or other format of recorded media.

The present disclosure also provides a composition for amplifying and detecting HIV-1 in a sample. The composition comprises, consists essentially of, or consists of (a) a primer and probe set that amplifies and detects a portion of the HIV-1 integrase (INT) gene comprising a forward primer oligonucleotide sequence comprising SEQ ID NO: 1, a reverse primer oligonucleotide sequence comprising SEQ ID NO: 2, and a probe oligonucleotide sequence, and (b) a primer and probe set that amplifies and detects a portion of the HIV-1 long terminal repeat (LTR) region, which comprises a forward primer oligonucleotide sequence comprising SEQ ID NO: 5, a reverse primer oligonucleotide sequence comprising SEQ ID NO: 6, a first probe oligonucleotide sequence, and a second probe oligonucleotide sequence, wherein each of the probe oligonucleotide sequences comprises a detectable label and/or a quencher moiety. Descriptions of the primer oligonucleotides and probe oligonucleotides set forth herein with respect to the aforementioned methods and kit also are applicable to those same aspects of the composition described herein. In some embodiments, the composition comprises a carrier, preferably a pharmaceutically (e.g., physiologically acceptable) carrier. Any suitable carrier can be used within the context of the disclosure, and such carriers are well known in the art. The composition can optionally be sterile or sterile with the exception of the oligonucleotides described herein.

The aforementioned kit and composition may further comprise primer and probe oligonucleotides that amplify and detect an internal control nucleic acid sequence, as described herein. In this regard, the kit and/or composition may comprise an internal control forward primer oligonucleotide sequence comprising SEQ ID NO: 11, SEQ ID NO: 53, or SEQ ID NO: 54, an internal control reverse primer oligonucleotide sequence comprising SEQ ID NO: 12, and an internal control probe oligonucleotide sequence comprising SEQ ID NO: 13 and a detectable label.

The kit and/or composition may be supplied in a solid (e.g., lyophilized) or liquid form. In one embodiment, the primer oligonucleotides, probe oligonucleotides, and other reagents are lyophilized (i.e., freeze dried). As discussed above, many single-target HIV detection systems known in the art provide PCR reagents in liquid format that requires frozen storage and batch testing. Lyophilization of the various components of the kit and composition described herein, however, eliminates the need for frozen storage and allows the assay components to be delivered in unit-dose format such that users may run the exact number of assays required, thereby minimizing reagent waste. The various components of the kits and composition of the present disclosure may optionally be contained within different containers (e.g., vial, ampoule, test tube, flask, or bottle) for each individual component (e.g., primer oligonucleotides, probe oligonucleotides, or buffer). Each component will generally be suitable as aliquoted in its respective container or provided in a concentrated form. Other containers suitable for conducting certain steps of the amplification/detection assay may also be provided. The individual containers are preferably maintained in close confinement for commercial sale.

The following examples further illustrate the invention but, of course, should not be construed as in any way limiting its scope.

Example 1

This example demonstrates a method for amplifying and detecting HIV-1 in a sample in accordance with the present disclosure.

An HIV-1 detection assay that utilizes real-time RT-PCR to amplify and detect HIV RNA genomic sequences extracted from human plasma or serum specimens has been developed by Abbott Molecular, Inc. (Des Plaines, Ill.) under the brand name ALINITY m™ HIV. The assay is intended to be used: 1) to assess disease prognosis by measuring the baseline HIV-1 level and to assess viral response to antiretroviral treatment by measuring changes in plasma HIV-1 RNA levels; and 2) as a diagnostic test to aid in the diagnosis of HIV-1 infection and to confirm HIV-1 infection in plasma or serum from individuals that have repeat reactive results with HIV immunoassays.

The ALINITY m™ HIV-1 assay consists of sample preparation, RT-PCR assembly, amplification/detection, and result calculation and reporting. All stages of the ALINITY m™ HIV-1 assay procedure are executed automatically by the ALINITY m™ instrument. HIV-1 RNA from human plasma or serum is extracted automatically on-board the Abbott ALINITY m™ instrument using the ALINITY m™ RNA Sample Prep Kit, ALINITY m™ Lysis Solution, and ALINITY m™ Diluent Solution, which employ magnetic microparticle technology to facilitate nucleic acid capture, wash, and elution.

At the beginning of the ALINITY m™ HIV-1 sample preparation process, a lyophilized unit-dose of internal control (containing an armored RNA sequence) is automatically rehydrated by the ALINITY m™ system and delivered into each sample preparation reaction. The internal control is then processed through the entire sample preparation and RT-PCR procedure along with the specimens, calibrators, and controls to demonstrate proper sample processing and assay validity.

25 μL of the purified RNA sample is then combined with 5 μL of liquid activator, which is then used to rehydrate lyophilized unit dose ALINITY m™ HIV-1 RT-PCR master mix reagent. The activator solution is prepared by mixing molecular biology grade water, magnesium chloride, tetramethyl ammonium chloride (TMAC), potassium chloride, and ProClin 950. The activator solution is supplied in liquid format in sealed and pouched multi-well plates, and provides the RT-PCR reaction with the necessary salts to activate RT-PCR enzymes and establish an optimal ionic strength environment. The formulation of the activator solution is shown in Table 1.

TABLE 1

Activator Reagent Formulation

| Component | Component Concentration (in 30 μL PCR) |
|---|---|
| Magnesium Chloride (MgCl2) | 3.5 mM |
| Tetramethyl Ammonium Chloride (TMAC) | 84 mM |
| Potassium Chloride (KCl) | 20 mM |
| ProClin 950 | 0.025% |
| Molecular Biology Grade Water | N/A |

The resulting material is then transferred to a reaction vessel, covered with 15 μL of ALINITY m™ Vapor Barrier Solution (mineral oil), and transferred to an amplification/detection module for reverse transcription, PCR amplification, and real-time fluorescence detection of HIV-1.

The RT-PCR master mix reagent formulation is compatible with lyophilization and enables completion of RT-PCR cycling in less than one hour. The master mix reagent is prepared by combining KAPA 2G DNA Polymerase, SuperScript III Reverse Transcriptase, Uracil-DNA Glycosylase (UDG), excipient (Ficoll 400, Ficoll 70, trehalose, melezitose and Molecular Biology Grade Water), PCR buffer components (Tris-HCl, Tween 20, and gelatin), dNTPs, oligonucleotide primers (as described herein), oligonucleotide probes and quenchers (as described herein), Cal610 passive reference dye, and ProClin 950.

SuperScript III Reverse Transcriptase is an engineered version of Moloney Murine Leukemia Virus (M-MLV) reverse transcriptase with reduced RNase H activity and increased thermal stability, and it can be used to synthesize first-strand cDNA at temperatures up to 55° C., providing increased specificity. KAPA2G Polymerase is an engineered enzyme for higher processivity and speed through directed evolution, which offers significantly faster extension rates than wild-type TAQ® DNA polymerase. KAPA2G has a highly processive 5'-3' DNA polymerase but lacks 3'-5' exonuclease activity. Uracil-DNA Glycosylase (UDG) catalyzes the release of free uracil from uracil-containing DNA and provides a means of contamination control for external amplicons containing uracil.

The master mix reagent is filled in unit-dose format into multi-well plates and lyophilized. The lyophilized plates are then sealed and pouched. The master mix formulation is set forth in Table 2.

TABLE 2

Master Mix Formulation

| Master Mix Component | Component Concentration (in 30 μL PCR) |
|---|---|
| HIV INT Forward Primer | 0.1125 μM |
| HIV INT Reverse Primer | 1.125 μM |
| HIV INT Probe | 0.225 μM |
| HIV Quencher Oligo | 0.9 μM |
| HIV LTR Forward Primer | 0.1 μM |
| HIV LTR Reverse Primer | 0.4 μM |
| HIV LTR1 Probe | 0.2 μM |
| HIV LTR1 Quencher Oligo | 0.5 μM |
| HIV LTR2 Probe | 0.2 μM |
| HIV LTR2 Quencher Oligo | 0.5 μM |
| IC Forward Primer | 0.15 μM |
| IC Reverse Primer | 0.24 μM |
| IC Probe | 0.6 μM |
| Cal610 Passive Reference Dye | 0.051 mM |
| dNTPs | 0.5 mM |
| ProClin 950 | 0.0069% |
| Tris-HCl | 55 mM |
| Tween 20 | 0.011% |
| Gelatin | 0.011% |
| Ficoll 400 | 1.81% |
| Ficoll 70 | 1.81% |
| Trehalose | 0.60% |
| Melezitose | 1.81% |
| KAPA 2G Polymerase | 2.6 units/reaction |
| SuperScript III Reverse Transcriptase | 6 units/reaction |
| Uracil-DNA Glycosylase | 0.2 U/rxn |
| Molecular Biology Grade Water | N/A |

The RT-PCR cycling conditions used by the ALINITY m™ HIV-1 assay are set forth in Table 3.

TABLE 3

RT-PCR Cycling Conditions

| Step | Description | Cycles | Temp. (C. °) | Dwell (sec.) |
|---|---|---|---|---|
| 1 | Reverse Transcription | 1 | 52 | 300 |
| 2 | Hot Start | 1 | 95 | 181.2 |
| 3 | Low Stringency Amplification (no read) | 2 | 95 50 | 2.4 14 |
| 4 | High Stringency Amplification (no read) | 8 | 95 60 | 2.4 14 |
| 5 | Amplification (no read) | 3 | 95 55 | 2.4 14 |
| 6 | Amplification/ Read | 31 | 95 55 35 (read) | 6 24.5 12.3 |

The internal control target is prepared by mixing excipient (trehalose and Molecular Biology Grade Water) and internal control bulk (consisting of internal control armored RNA diluted in filtered, defibrinated human plasma (Basematrix, SeraCare Life Science, Inc., Milford, Mass.). The formulation of the internal control is set forth in Table 4 below. The internal control armored RNA target sequence is derived from the hydroxypyruvate reductase gene of the pumpkin plant, *Cucurbita pepo*, which is unrelated to HIV-1. The internal control is filled in unit-dose format into multi-well plates and lyophilized. The lyophilized plates are then sealed and pouched.

TABLE 4

Internal Control Formulation

| Component | Component Concentration (pre-lyophilization) |
|---|---|
| Internal Control Armored RNA | Ct Target = 16.3 |
| Base Matrix | 50% |
| Trehalose | 0.94% |
| Molecular Biology Grade Water | 49.06% |

The PCR formulation and cycling conditions described above may be further modified to optimize the assay.

Example 2

This example describes experiments to establish the limit of detection (LOD) of the ALINITY m™ HIV assay.

The LOD for the ALINITY m™ HIV-1 assay was determined by analysis of a dilution series of the World Health Organization (WHO) $3^{rd}$ International Standard for HIV-1 RNA (10/152), prepared in HIV-1 negative human plasma.

The dilution panel of the HIV-1 WHO standard consisted of six panel members targeted to bracket the assay's intended Limit of Detection (LOD) and the expected Lower Limit of Quantitation (LLOQ) of 20 copies/mL. The concentration of the LOD panel members used in this study were 40, 30, 20, 10, 5 and 2.5 copies/mL, resulting in three panel members targeted to detection rates between 10% and 90% and one or more panel members targeted to detection rates exceeding 95%. Panel member concentrations were calculated based on the assigned concentration of the WHO HIV-1 standard (see Table 5).

TABLE 5

HIV-1 Panel Members

| | Target HIV-1 RNA Concentration | |
|---|---|---|
| Panel Member | log copies/mL | copies/mL |
| 1 | 1.60 | 40.00 |
| 2 | 1.48 | 30.00 |
| 3 | 1.30 | 20.00 |
| 4 | 1.00 | 10.00 |
| 5 | 0.70 | 5.00 |
| 6 | 0.40 | 2.50 |

A total of 96 replicates for each panel member were tested across four ALINITY m™ HIV-1 amplification reagent lots and two ALINITY m™ systems. For each panel member, 3 testing runs with each of the four ALINITY m™ HIV-1 amplification reagent lots were performed across three days including eight replicates per day (e.g. four amplification reagent lots×eight replicates/day×three days=96 total replicates tested) (see Table 6).

TABLE 6

Study Sampling

| Panel Member | Number Amplification Reagent Lots | Replicates per Day per Reagent Lot | Number of Days | Total Replicates Tested |
|---|---|---|---|---|
| 1 | 4 | 8 | 3 | 96 |
| 2 | 4 | 8 | 3 | 96 |
| 3 | 4 | 8 | 3 | 96 |
| 4 | 4 | 8 | 3 | 96 |

TABLE 6-continued

Study Sampling

| Panel Member | Number Amplification Reagent Lots | Replicates per Day per Reagent Lot | Number of Days | Total Replicates Tested |
|---|---|---|---|---|
| 5 | 4 | 8 | 3 | 96 |
| 6 | 4 | 8 | 3 | 96 |

The sample size per the recommendation in Clinical and Laboratory Standards Institute (CLSI) EP17-A2 Guideline for Evaluation of Detection Capability for Clinical Laboratory Measurement Procedures is a minimum of five panel members and a minimum of 60 replicates per panel member. The sample size chosen for the study for statistical analysis was a minimum of five panel members and a minimum of 80 valid replicates per panel member. Therefore, the sample size used in this study exceeded the minimum sample size recommended in the CLSI EP17-A2 Guideline.

The study was conducted using four lots of ALINITY m™ HIV-1 Amplification Kit, one lot of ALINITY m™ HIV-1 Calibrator Kit, Control Kit, and Sample Prep RNA Kit reagents and one lot of ALINITY m™ Lysis Solution, Diluent Solution, and Vapor Barrier Solution on two ALINITY m™ Systems.

Explanation of the Sample Identification Convention

Within the line listing, each line identifies the sample identification (SID) assigned to the tested sample. Calibrators and Controls were named as required by ALINITY m™ instrument software.

The SID was: LODyyzz
Key: LOD=study (Limit of Detection)
  yy=panel number (01 to XX)
  zz=run number (01 to XX)

Example sample IDs used in this study are listed in Table 7 below:

TABLE 7

| Sample ID* | Sample Description |
|---|---|
| LOD0102I06 | LOD, panel 1, run 2 |

*The ALINITY m instrument software requires unique SIDs in sequential order to process samples. Additional identifiers were added by the operator to create a unique SID for each sample.

Calibration and Assay Control Validity Criteria

A calibration was established for each combination of ALINITY m HIV-1 Amplification Kit lot, Sample Preparation Kit lot, and ALINITY m Lysis Solution on each instrument prior to running the samples. Each calibrator was tested in replicates of three along with 1 replicate of Negative Control, Low Positive Control, and High Positive Control for each reagent lot/instrument used in the study. Calibration curve parameters and each individual control value were evaluated against the validity criteria in the assay-application specification file and passed.

The study was performed over three days and the ALINITY m HIV-1 assay controls were tested each day on each instrument to verify the validity of the assay. Each individual control value was evaluated against the assay-specific validity criteria and passed.

Sample Validity Criteria

If a sample was invalid, the result was excluded from analysis and retested if necessary to achieve the minimum sample size.

If a "no test" occurred (due to technical or instrument errors), the result was excluded from the analysis and repeated if necessary to ensure that the minimum sample size was achieved.

Statistical Analysis

The analysis variable for the statistical analysis was the ALINITY m HIV-1 sample's result interpretation. If the sample's result/interpretation was "Not Detected," then the sample was considered not detected; otherwise the sample was considered "Detected."

The LOD was defined as the concentration corresponding to the 95% probability of detection. The detection rate, from across all reagent lots and instruments, was estimated for each panel member as described in the following equation:

$$\text{Detection Rate} = \frac{\text{Number of Replicates Detected}}{\text{Total Number of Replicates Tested}} \times 100$$

where the Total Number of Replicates Tested was the sum of the "Detected" and "Not Detected" replicates. A "Replicate" was defined as an individual PCR reaction, only valid replicates were included in the analysis.

For all reagent lots and instruments combined, the limit of detection was estimated from a probit analysis. A probit regression model was fitted using PROC PROBIT in SAS, with $\log_{10}$ of the target concentration ($\log_{10}(X)$, using $\log_{10}$ option) as the independent variable and the detection rate $P(Y=1)$ as the response variable:

$$P(Y=1) = C + (1-C)\Phi[(\beta 1)(\log_{10}(X))]$$

where $\beta 0$, $\beta 1$ denote the parameter estimates; X denotes the target concentration (copies/mL), P denotes the probability of detection, C denotes the natural (detection rate), $\Phi[z]$ denotes the normal cumulative distribution function. The model was fitted with the $\log_{10}$ option and without the OPTC option since it was assumed that the natural detection rate was zero. Since the model with the $\log_{10}$ transformation of target concentrations was used, the estimates and confidence intervals were obtained by taking the antilog transformation.

Acceptance Criteria

The acceptance criteria for this study was the HIV-1 concentration corresponding to the 95% detection rate (LOD) determined in the analysis shall be less than or equal to 20 copies/mL. LOD is defined as the concentration corresponding to the 95% probability for detection.

PR 2:
The assay shall detect less than or equal to 20 copies/mL with 95% probability, processing 1 mL or less of sample.

PR 21:
The assay shall detect HIV-1 Group M subtypes A, B, BF, C, D, CRF01-AE, F, CRF02-AG, G, H, Group O, and Group N.

This study established the LOD for the ALINITY m HIV-1 assay using the WHO 3rd International Standard for HIV-1 RNA (10/152), which is comprised of HIV-1 Group M, subtype B. Therefore, PR2 and the Group M, subtype B portion of PR21 were verified per this protocol. LOD performance of the additional HIV-1 Group/Subtypes listed in PR21 will be verified as part of a separate study.

For the LOD study using HIV-1 Group M, subtype B, panel members 1 through 4 were included in the probit regression model based upon the percent detection. The probit analysis demonstrated that the assay is capable of detecting the presence of 13.88 copies/mL (95% Confidence Interval of 11.16 to 18.98 copies/mL) of HIV-1 RNA in plasma samples with 95% probability for Group M, subtype B. Panel members 4, 5 and 6 each exhibited detection rates above 95%. Therefore, panel members 5 and 6 were excluded from the probit analysis to ensure that the regression model utilized only one panel member (panel member 4) with detection rates at, or above, 95%. The limit of detection (LOD) of the ALINITY m HIV-1 assay is shown in FIG. 1. The results supporting FIG. 1 are shown in Tables 8, 9 and 10.

TABLE 8

ALINITY m ™ HIV-1 Limit of Detection (LOD) for All Lots Combined

| Panel Member | HIV-1 RNA Concentration (copies/mL) | Number of Replicates Tested | Number of Replicates Detected | Detection Rate (%) |
|---|---|---|---|---|
| 06 | 40.00 | 95 | 95 | 100.0 |
| 05 | 30.00 | 96 | 96 | 100.0 |
| 04 | 20.00 | 96 | 93 | 96.9 |
| 03 | 10.00 | 96 | 89 | 92.7 |
| 02 | 5.00 | 96 | 64 | 66.7 |
| 01 | 2.50 | 96 | 36 | 37.5 |

TABLE 9

ALINITY m ™ HIV-1 Limit of Detection (LOD) for All Lots Combined

| | Concentration | | | | | |
|---|---|---|---|---|---|---|
| | | 95% Fiducial Limits | | | 95% Fiducial Limits | |
| Probability | log copies/mL | Lower | Upper | copies/mL | Lower | Upper |
| 0.01 | −0.36465 | −0.65253 | −0.17376 | 0.43187 | 0.22257 | 0.67026 |
| 0.02 | −0.26119 | −0.52249 | −0.08740 | 0.54804 | 0.30027 | 0.81770 |
| 0.03 | −0.19555 | −0.44007 | −0.03252 | 0.63745 | 0.36302 | 0.92785 |
| 0.04 | −0.14617 | −0.37813 | 0.00882 | 0.71421 | 0.41867 | 1.02051 |
| 0.05 | −0.10601 | −0.32779 | 0.04249 | 0.78342 | 0.47012 | 1.10278 |
| 0.06 | −0.07182 | −0.28497 | 0.07118 | 0.84758 | 0.51883 | 1.17810 |
| 0.07 | −0.04184 | −0.24746 | 0.09637 | 0.90815 | 0.56563 | 1.24845 |
| 0.08 | −0.01500 | −0.21391 | 0.11895 | 0.96604 | 0.61107 | 1.31508 |
| 0.09 | 0.00941 | −0.18341 | 0.13951 | 1.02189 | 0.65553 | 1.37883 |
| 0.10 | 0.03187 | −0.15536 | 0.15846 | 1.07615 | 0.69927 | 1.44031 |
| 0.15 | 0.12490 | −0.03948 | 0.23716 | 1.33322 | 0.91309 | 1.72649 |
| 0.20 | 0.19884 | 0.05221 | 0.30012 | 1.58066 | 1.12773 | 1.99581 |
| 0.25 | 0.26227 | 0.13047 | 0.35452 | 1.82923 | 1.35044 | 2.26216 |
| 0.30 | 0.31923 | 0.20034 | 0.40380 | 2.08560 | 1.58613 | 2.53399 |
| 0.35 | 0.37201 | 0.26460 | 0.44995 | 2.35513 | 1.83907 | 2.81806 |
| 0.40 | 0.42210 | 0.32501 | 0.49430 | 2.64302 | 2.11354 | 3.12105 |
| 0.45 | 0.47056 | 0.38277 | 0.53790 | 2.95502 | 2.41420 | 3.45063 |
| 0.50 | 0.51825 | 0.43876 | 0.58166 | 3.29801 | 2.74640 | 3.81646 |
| 0.55 | 0.56594 | 0.49367 | 0.62651 | 3.68081 | 3.11649 | 4.23166 |
| 0.65 | 0.66449 | 0.60256 | 0.72374 | 4.61838 | 4.00465 | 5.29342 |
| 0.70 | 0.71727 | 0.65789 | 0.77882 | 5.21523 | 4.54868 | 6.00925 |
| 0.75 | 0.77424 | 0.71515 | 0.84070 | 5.94614 | 5.18982 | 6.92944 |
| 0.80 | 0.83767 | 0.77627 | 0.91225 | 6.88122 | 5.97407 | 8.17057 |
| 0.85 | 0.91160 | 0.84474 | 0.99843 | 8.15833 | 6.99427 | 9.96385 |
| 0.90 | 1.00463 | 0.92798 | 1.10977 | 10.10715 | 8.47186 | 12.87571 |
| 0.91 | 1.02710 | 0.94774 | 1.13701 | 10.64383 | 8.86622 | 13.70910 |
| 0.92 | 1.05151 | 0.96909 | 1.16672 | 11.25920 | 9.31295 | 14.67967 |
| 0.93 | 1.07835 | 0.99244 | 1.19950 | 11.97697 | 9.82737 | 15.83086 |
| 0.94 | 1.10832 | 1.01838 | 1.23626 | 12.83284 | 10.43238 | 17.22888 |
| 0.95 | 1.14251 | 1.04783 | 1.27832 | 13.88385 | 11.16420 | 18.98106 |
| 0.96 | 1.18268 | 1.08225 | 1.32791 | 15.22915 | 12.08516 | 21.27688 |
| 0.97 | 1.23205 | 1.12437 | 1.38907 | 17.06296 | 13.31581 | 24.49486 |
| 0.98 | 1.29769 | 1.18007 | 1.47066 | 19.84700 | 15.13821 | 29.55727 |
| 0.99 | 1.40115 | 1.26740 | 1.59974 | 25.18559 | 18.50964 | 39.78654 |

TABLE 10

| LOD Summary Table for All Lots Combined | |
|---|---|
| LOD (copies/mL) | Acceptance Criteria |
| 13.88 | Met |

Assay controls tested on one run were invalid due to an invalid Negative Control (error code 9209) and were excluded. No samples were associated with this Control set. When an assay control was invalid, the ALINITY m system software invalidated all control levels tested in that control set. Therefore, the associate High Positive Control and Low Positive Control from this control event were also invalidated. Assay controls were successfully retested prior to testing samples. One sample displayed a "Diluted" Flag and was excluded as incorrectly classified. The technician incorrectly ordered this replicate to be tested as a diluted sample (i.e., diluted in ALINITY m™ Specimen Diluent per the assay's optional Specimen Dilution Procedure) when the sample was not diluted (i.e. tested neat). This sample was excluded from the analysis and was not retested as the minimum sample size was achieved. The minimum number of replicates for the panel member was met according to the protocol. All test results were reviewed. Certain observations may have been excluded from the analysis in accordance with the protocol exclusion criteria (i.e., control or validity criteria failure, instrument errors or problems, acknowledged technologist error, inclusion criteria not met, and/or protocol not followed). All results that were not excluded were eligible for analysis.

An explanation of excluded observations is summarized in Table 11. An overall line-listing summary of the total number of included results, excluded results, instrument failure events, and run failure events for validity QC is provided in Table 12.

TABLE 11

| ALINITY m ™ HIV-1 Limit of Detection Study - Overall Line Listing Summary | | | | |
|---|---|---|---|---|
| Total Number | Number of Control Results | | Number of Sample Results | |
| of Results | Valid | Invalid | Included | Excluded |
| 615 | 36 | 3 | 575 | 1 |

TABLE 12

| ALINITY m ™ HIV-1 Limit of Detection Study - Excluded Data Summary | | | | |
|---|---|---|---|---|
| Exclusion Code | N | OBS Number(s) | Reason for Exclusion | Impact to Study Conclusion |
| 2 - Classified incorrectly | 1 | 4 | Sample was tested incorrectly and was excluded from the analysis. | There is no impact to the study conclusion. The samples were retested correctly and the minimum number of replicates for each specimen type was met per the protocol. |
| 27 - Invalid run | 3 | 1, 2, 3 | Assay Controls were invalid and were excluded from the analysis. | There is no impact to the study conclusion. No samples were tested as part of the run. Assay Controls were successfully retested prior to testing samples. |

A total of 615 results were generated in the study; a total of 575 results were included in the analysis; a total of 1 result was excluded from the analysis; 36 valid control results and 3 invalid control results. The results of this example demonstrate that the HIV-1 concentration corresponding to the 95% detection rate (LOD) was 13.88 copies/mL, and the LOD claim for the ALINITY m HIV-1 assay was 20 copies/mL.

Example 3

This example describes experiments which establish the linear range of the ALINITY m™ HIV-1 assay by testing a panel prepared using HIV-1 viral stock representing Group M, subtype B.

Linearity was evaluated by testing 11 panel members. Eight members spanned the intended dynamic range of the assay (20 to 10,000,000 copies/mL), including a member targeting the expected Lower Limit of Quantification (LLOQ) at 20 copies/mL. One member exceeding the expected Upper Limit of Quantification (ULOQ) at 10,000,000 copies/mL, and two additional panel members outside this range were also included in the testing.

Panel members consisted of an HIV-1 viral stock representing Group M, subtype B, diluted in negative plasma. Panel quantitation values were established using internal reference standards that are traceable to a viral standard from the Virology Quality Assurance (VQA) Laboratory of the AIDS Clinical Trial Group and are set forth in Table 13.

TABLE 13

HIV-1 Panel Members

| Panel Member | Target HIV-1 RNA Concentration | |
| --- | --- | --- |
| | log copies/mL | copies/mL |
| 1 | 7.30 | 20,000,000 |
| 2 | 6.00 | 1,000,000 |
| 3 | 5.00 | 100,000 |
| 4 | 4.00 | 10,000 |
| 5 | 3.00 | 1,000 |
| 6 | 2.00 | 100 |
| 7 | 1.60 | 40 |
| 8 | 1.50 | 30 |
| 9 | 1.30 | 20 |
| 10 | 1.18 | 15 |
| 11 | 1.00 | 10 |

A total of 24 replicates for each panel member were tested using one lot of ALINITY m™ HIV-1 Amplification reagents and 1 ALINITY m™ System.

The study design was based on the recommendations in Clinical and Laboratory Standards Institute (CLSI) titled "EP06-A, Evaluation of the Linearity of Quantitative Measurement Procedures: A Statistical Approach."

The sample size per the recommendation in CLSI EP06-A Guideline is a minimum of seven panel members for developers and a minimum of two replicates per panel member. The sample size chosen for the study was 11 panel members and 24 replicates per panel. Therefore, the sample size used in this study met or exceeded the minimum sample size recommended in CLSI EP06-A Guideline.

The study was conducted using one lot of ALINITY m™ HIV-1 Amp Kit IUO reagents, one lot of ALINITY m™ HIV-1 CTRL Kit IUO reagents, one lot of ALINITY m™ HIV-1 CAL Kit IUO reagents, one lot of Sample Prep RNA Kit IUO reagents, one lot of ALINITY m™ Lysis Solution IUO, one lot of ALINITY m™ Vapor Barrier Solution IUO, one lot of ALINITY m™ Diluent Solution IUO, and one ALINITY m™ System.

Explanation of the Sample Identification Convention

Within the line listing, each line identifies the sample identification (ID) assigned to the tested sample. Calibrators and Controls were named as required by ALINITY m™ instrument software.

The SID was: DLyyzz
Key: DL=study (Linearity)
    yy=panel number (01 to XX)
    zz=replicate (01 to 24)

Example sample IDs used in this study are listed below in Table 14.

TABLE 14

| Sample ID* | Sample Description |
| --- | --- |
| DL01I22 | Panel Member 1 (7.30 log copies/mL) |
| DL04I07 | Panel Member 4 (4.00 log copies/mL) |

*The ALINITY m ™ instrument software requires unique SIDs in sequential order to process samples. Additional identifiers were added by the operator to create a unique SID for each sample.

Calibration and Assay Control Validity Criteria

A calibration was established for the ALINITY m™ HIV-1 Amplification Kit lot, Sample Prep Kit lot and ALINITY m™ Lysis Solution lot on the instrument, prior to running the samples. Each calibrator was tested in replicates of 3 along with 1 replicate of Negative Control, Low Positive Control, and High Positive Control for each reagent lot/instrument used in the study. Calibration curve parameters and each individual control value were evaluated against the validity criteria in the assay-application specification file and passed.

ALINITY m™ HIV-1 assay controls were tested on the testing day to verify assay validity. Each individual control value was evaluated against the assay-specific validity criteria or equivalent and passed.

Sample Validity Evaluation

If a sample was invalid, the result was excluded from analysis and retested if necessary to achieve the minimum sample size. If all the retest replicates were valid, the retest results were included in the analysis along with any valid results from the original testing. To identify retest of invalid samples, an 'R' was added to the end of sample ID.

If a "no test" occurred (due to technical or instrument errors), the result was excluded from the analysis and repeated if necessary to ensure that the minimum sample size is achieved. To identify retest of 'no test' samples, an 'A' was added to the end of sample ID.

Statistical Analysis

The analysis variable for the statistical analysis is the ALINITY m™ HIV-1 concentration log copies/mL. The following analytical steps were performed:
  a) For each panel level, the standard deviation (SD) of ALINITY m™ HIV-1 results were calculated and the SD confirmed not to be greater than the following requirements for assay precision:
    0.25 log copies/mL from 100 copies/mL to 20,000,000 copies/mL assay.
    0.46 log copies/mL at less than or equal to 3 times the LLOQ.
  Since the SD met the above criteria then the analyses continue to step b) through g).

b) Outlier Identification:
Outliers were detected and excluded by checking if any ALINITY m™ HIV-1 result was outside the mean±4×SD range for any panel. The following analyses (step c-step g) were performed with and without outlier.
c) Performed the first, second, and third order polynomial least-square regression and tested if the nonlinear coefficients were significant at significance level 0.05.
d) If there was no significant nonlinear coefficient, then the assay was defined as linear within the range encompassed by the panel members. Continue to step f).
e) If there was a significant nonlinear coefficient, then the nonlinear regression model with the lowest Mean Square Error (MSE) as the fitted nonlinear model was chosen and the difference in the predicted concentration (Y) between the fitted nonlinear model and the linear model for each panel member was calculated.
If the difference in the predicted concentration (Y) between the fitted nonlinear model and the linear model for the panel member with the lowest and/or highest target concentration was greater than 0.5 log copies/mL, then the panel member with the greater difference was removed. Continue to step c).
If the difference in the predicted concentration (Y) between the fitted nonlinear model and the linear model for each panel member was less than or equal to 0.5 log copies/mL, then:
The lower limit of the linear range was defined as the target concentration of the panel member with the lowest target concentration,
The upper limit of the linear range was defined as the target concentration of the panel member with the highest target concentration, and
The assay was defined as linear within the lower limit of the linear range and the upper limit of the linear range.
Note that the maximum allowable difference between polynomial and linear models (0.5 log copies/mL) was taken from The Panel on Antiretroviral Guidelines for Adults and Adolescents. Guidelines for the use of antiretroviral agents in HIV-1-infected adults and adolescents. Department of Health and Human Services (2014), which states that the minimal change in viral load considered to be statistically significant (2 standard deviations) is a threefold, or a 0.5 log copies/mL change.
f) Performed a least-square linear regression and generate a regression plot including the panel members that were within the linear range determined from step d) or step e).
g) If there was significant nonlinear coefficient from the regression analysis with all panel members, a plot for all panel members using the individual ALINITY m™ HIV-1 results as the Y-axis and the target concentration as the X-axis was generated. Two different symbols representing the results within and out of the linear range are presented on the plot. Two lines representing the predicted mean concentrations from the fitted non-linear model and the linear model are also presented on the plot. The panel member(s) that are outside of the linear range are highlighted on the plot.

Acceptance Criteria

The acceptance criteria for this study is the lower limit of the linear range shall be less than or equal to 20 copies/mL and the upper limit of the linear range shall be greater than or equal to 10,000,000 copies/mL for HIV-1 Group M, Subtype B.

Figure 2:
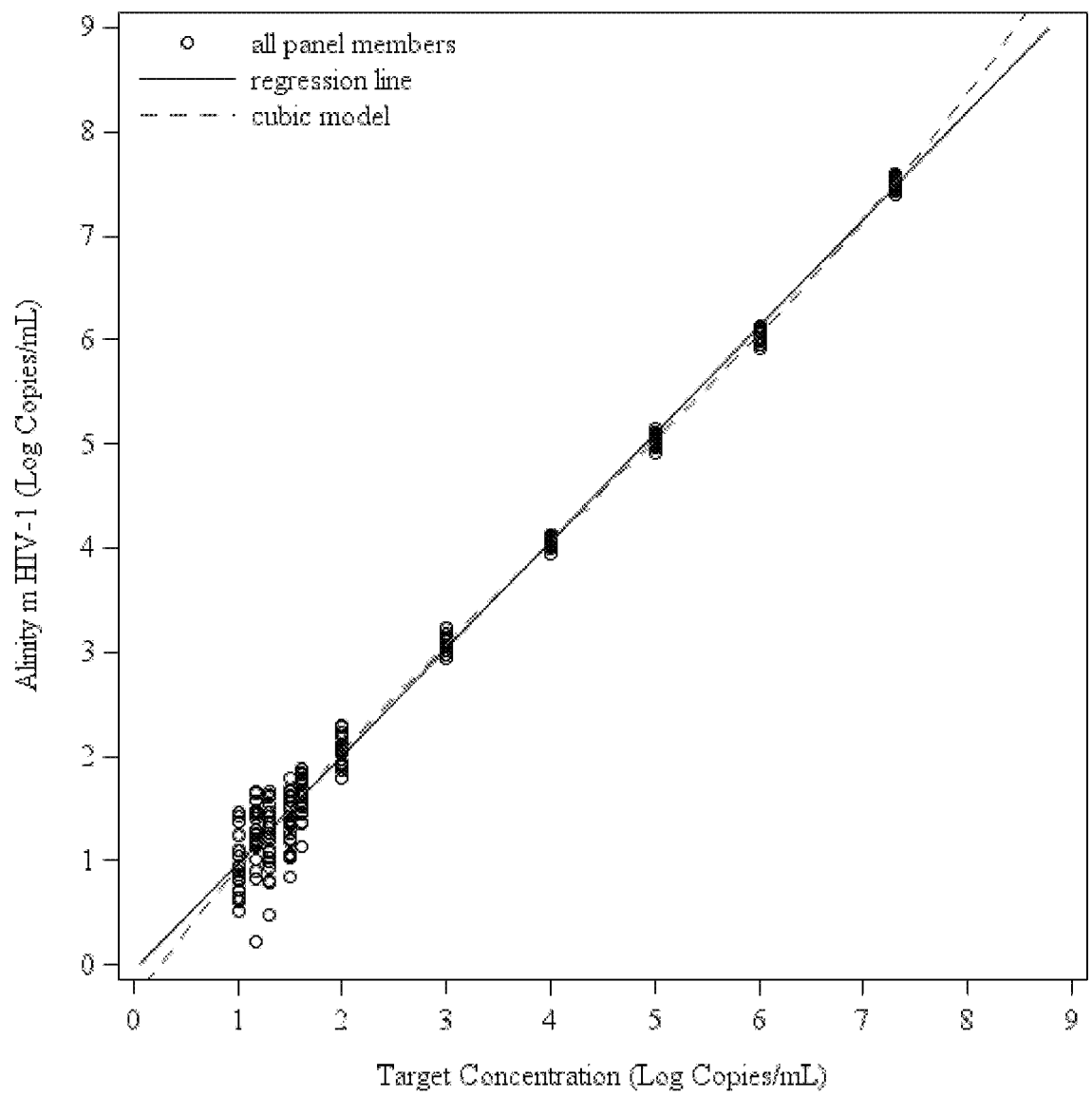
FIG. 2 is a graph illustrating ALINITY m™ HIV-1 linearity, plotting linear and nonlinear regression with all panel members.
Figure 3:
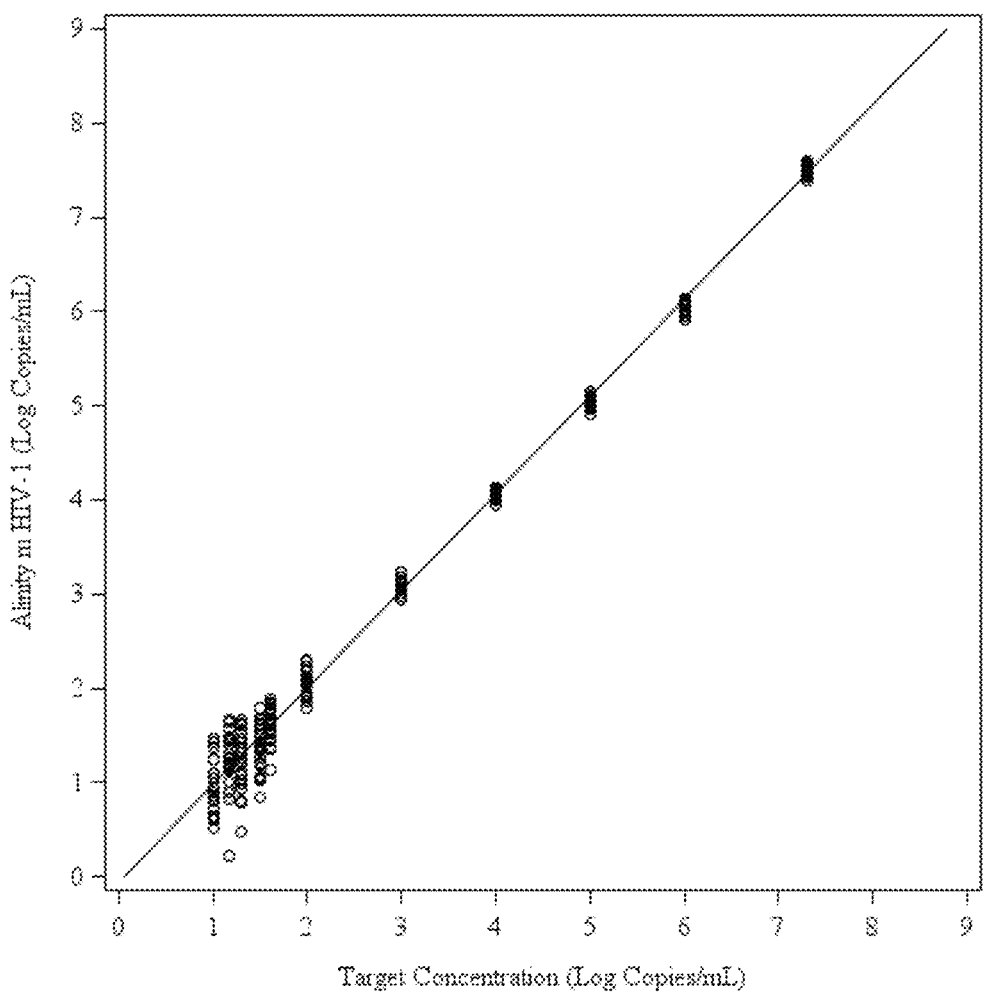
FIG. 3 is a least-squares regression plot for ALINITY m™ HIV-1 panel members within the linear range.
Figure 4:
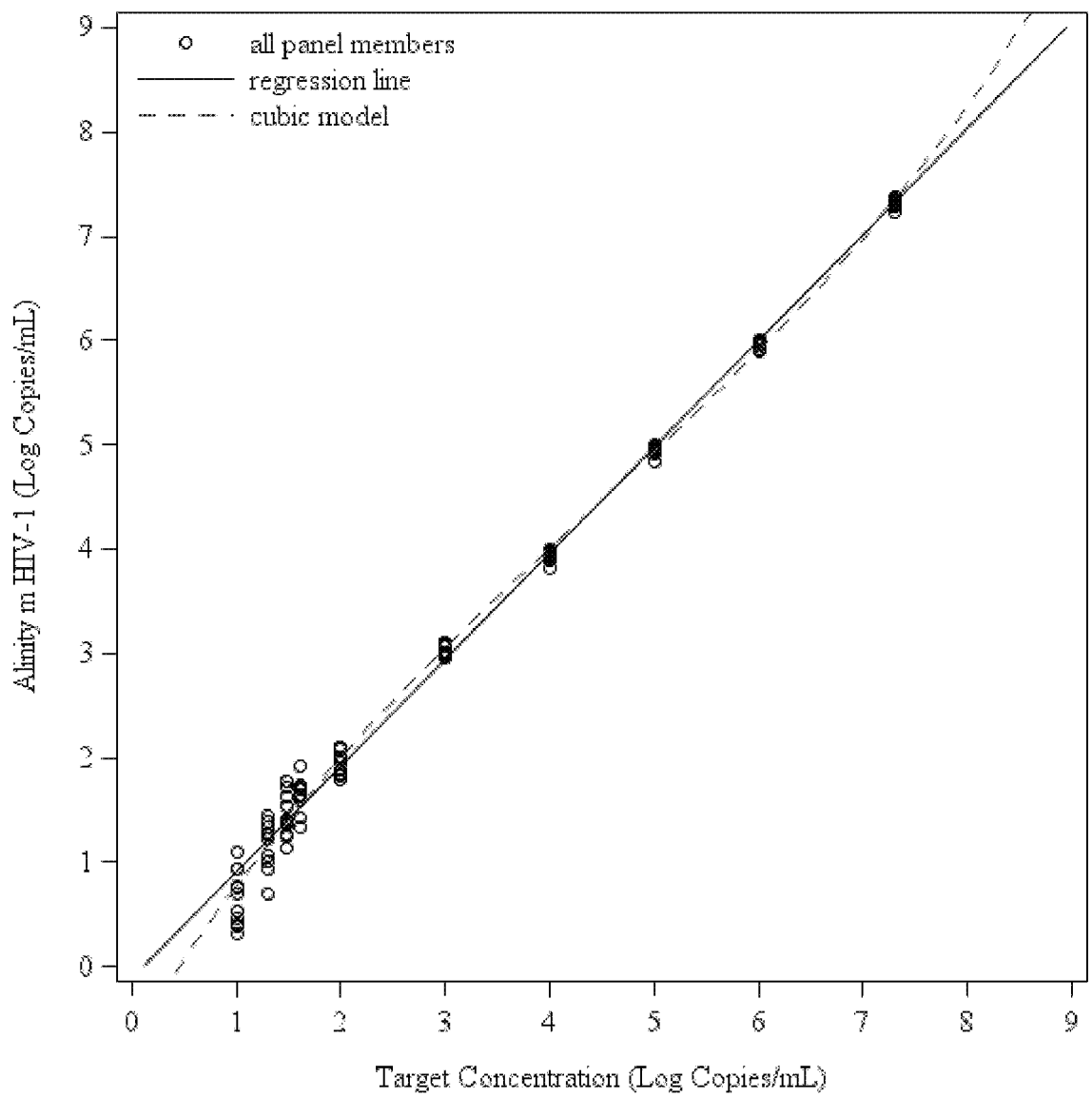
FIG. 4 is a graph of ALINITY m™ HIV-1 Group M, subtype A linear and nonlinear regression plots with all panel members.
Figure 5:
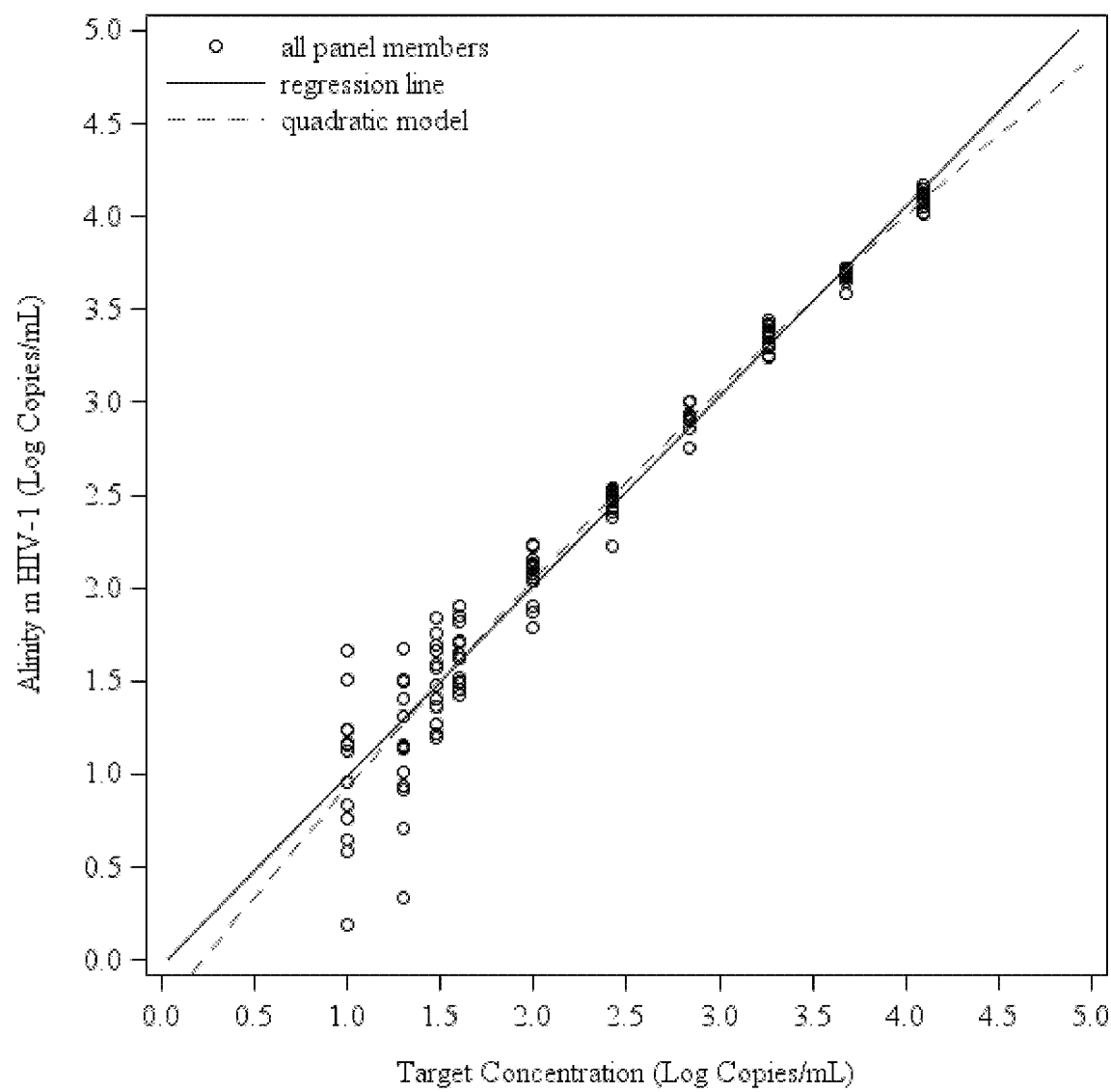
FIG. 5 is a graph of ALINITY m™ HIV-1 Group M, subtype BF linear and nonlinear regression plots with all panel members.
Figure 6:
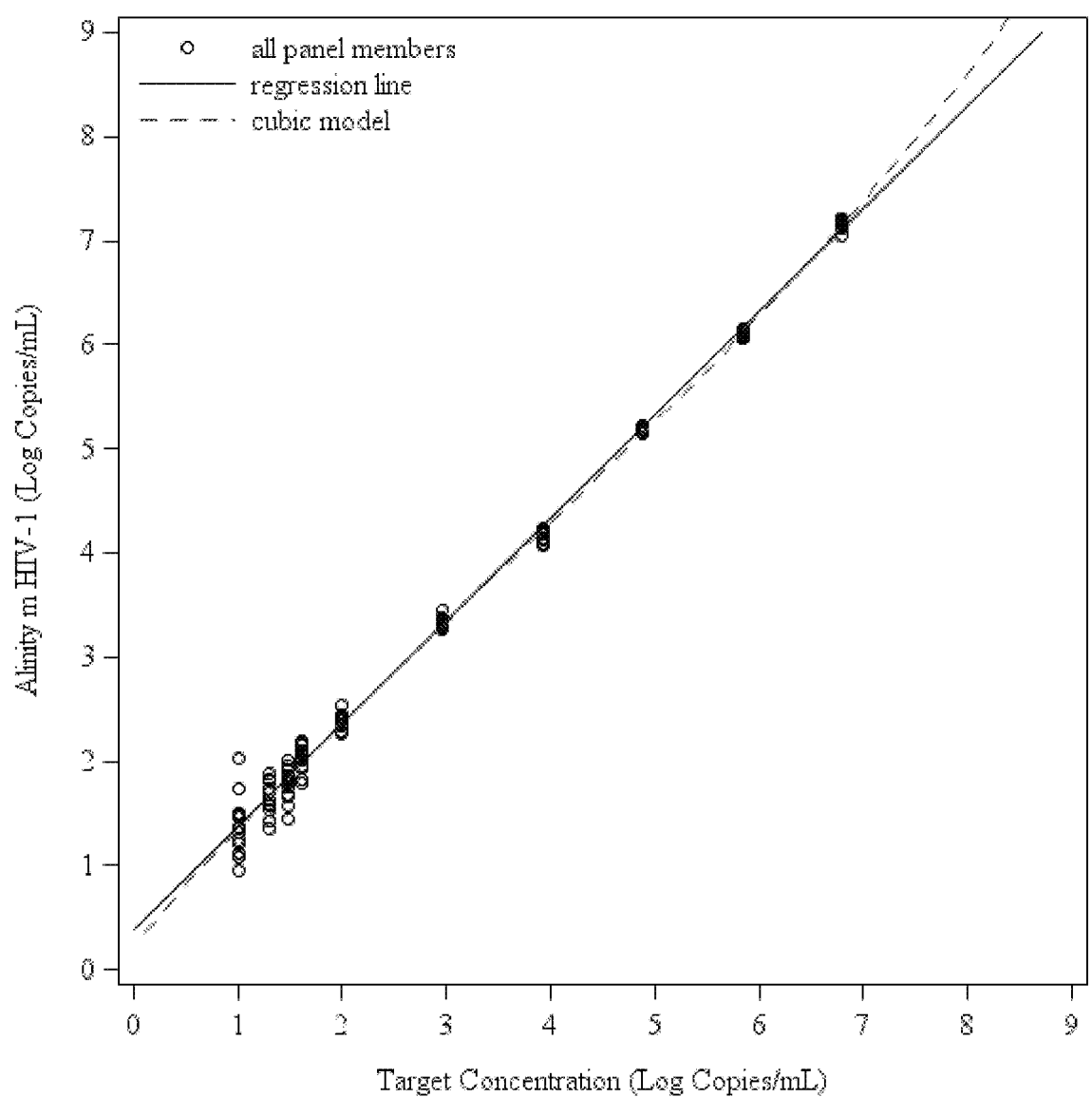
FIG. 6 is a graph of ALINITY m™ HIV-1 Group M, Subtype C linear and nonlinear regression plots with all panel members.
Figure 7:
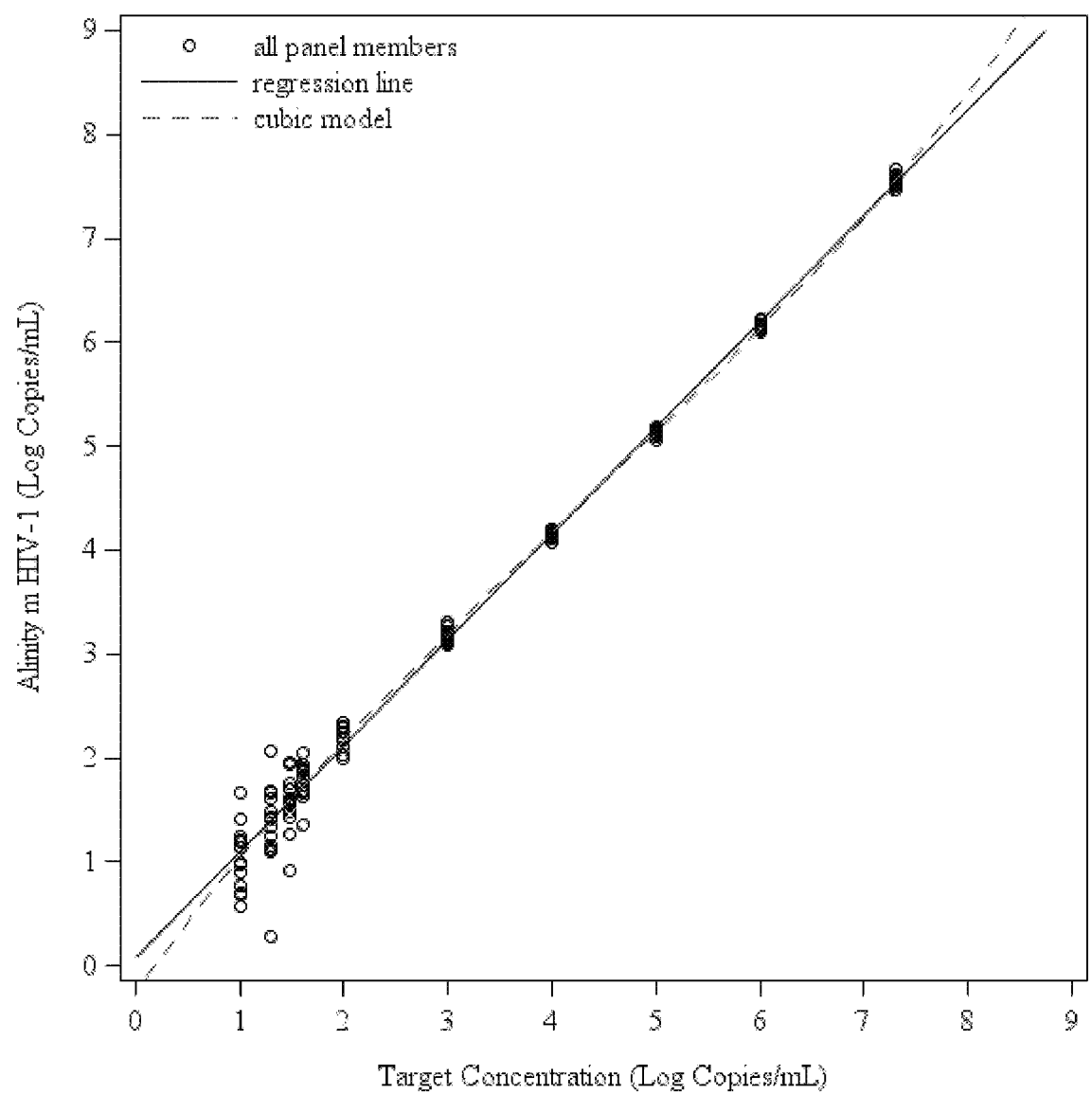
FIG. 7 is a graph of ALINITY m™ HIV-1 Group M, subtype AG linear and nonlinear regression plots with all panel members.
Figure 8:
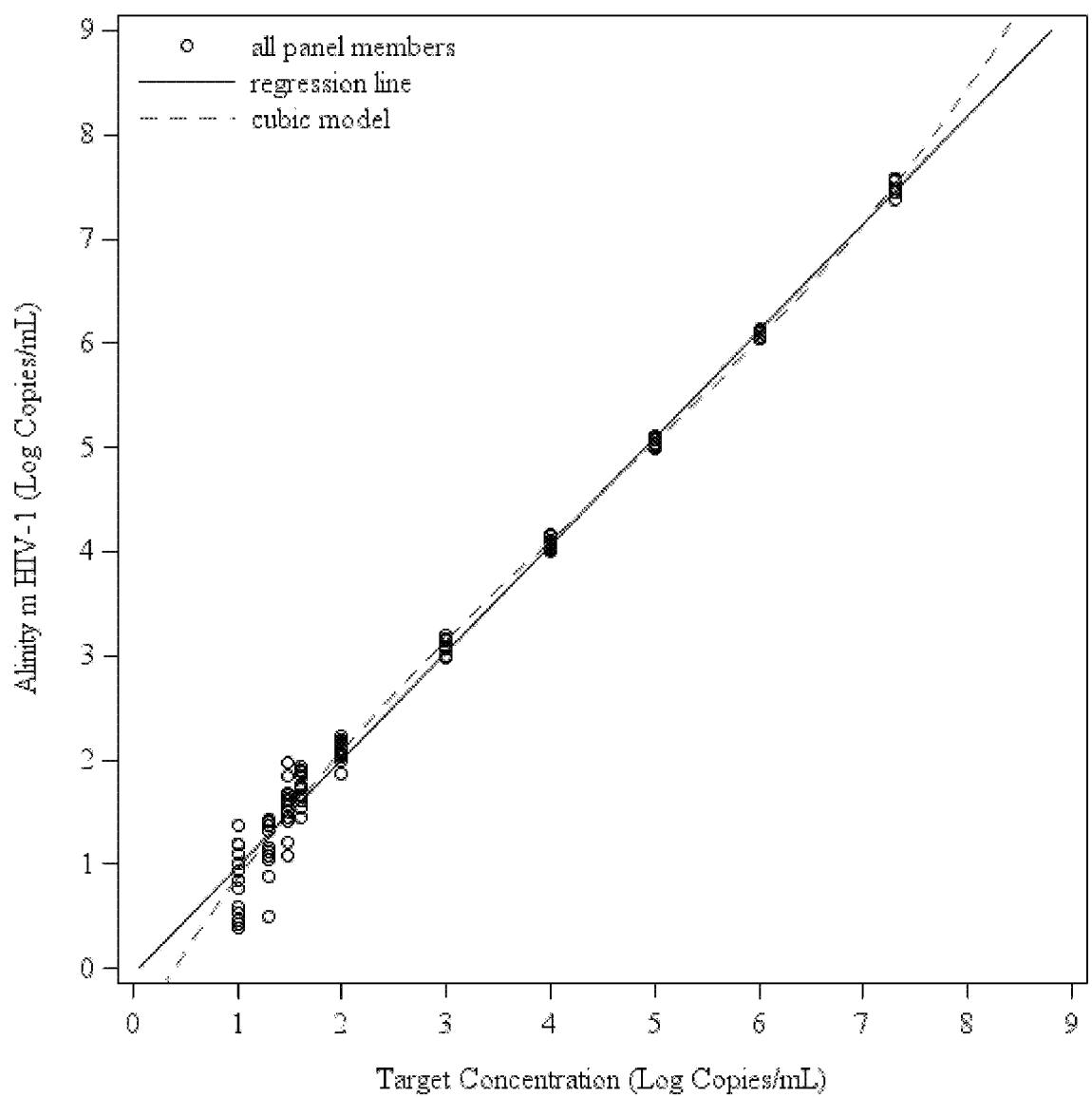
FIG. 8 is a graph of ALINITY m™ HIV-1 Group M, subtype F linear and nonlinear regression plots with all panel members.
Figure 9:
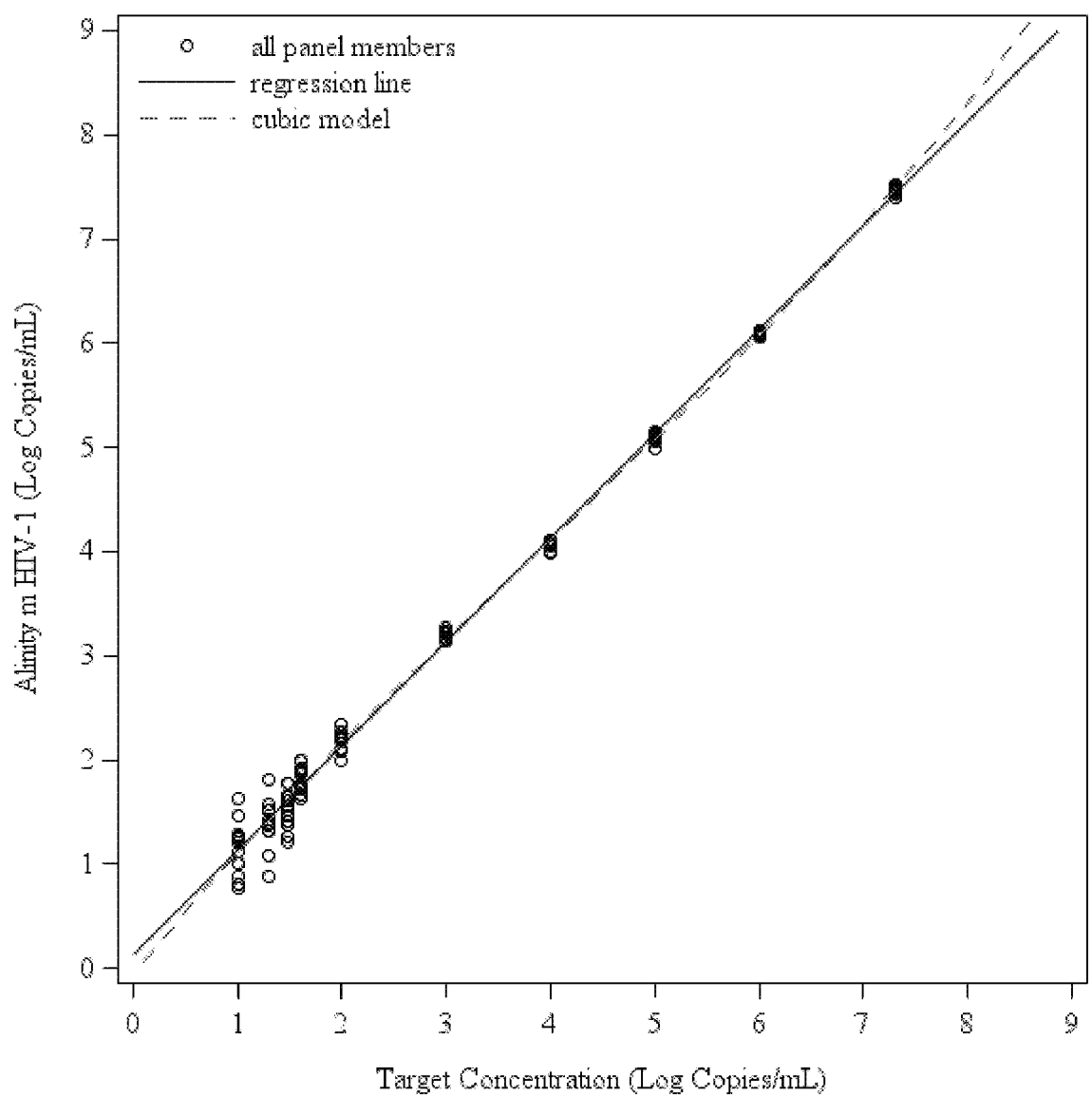
FIG. 9 is a graph of ALINITY m™ HIV-1 Group M, subtype G linear and nonlinear regression plots with all panel members.
Figure 10:
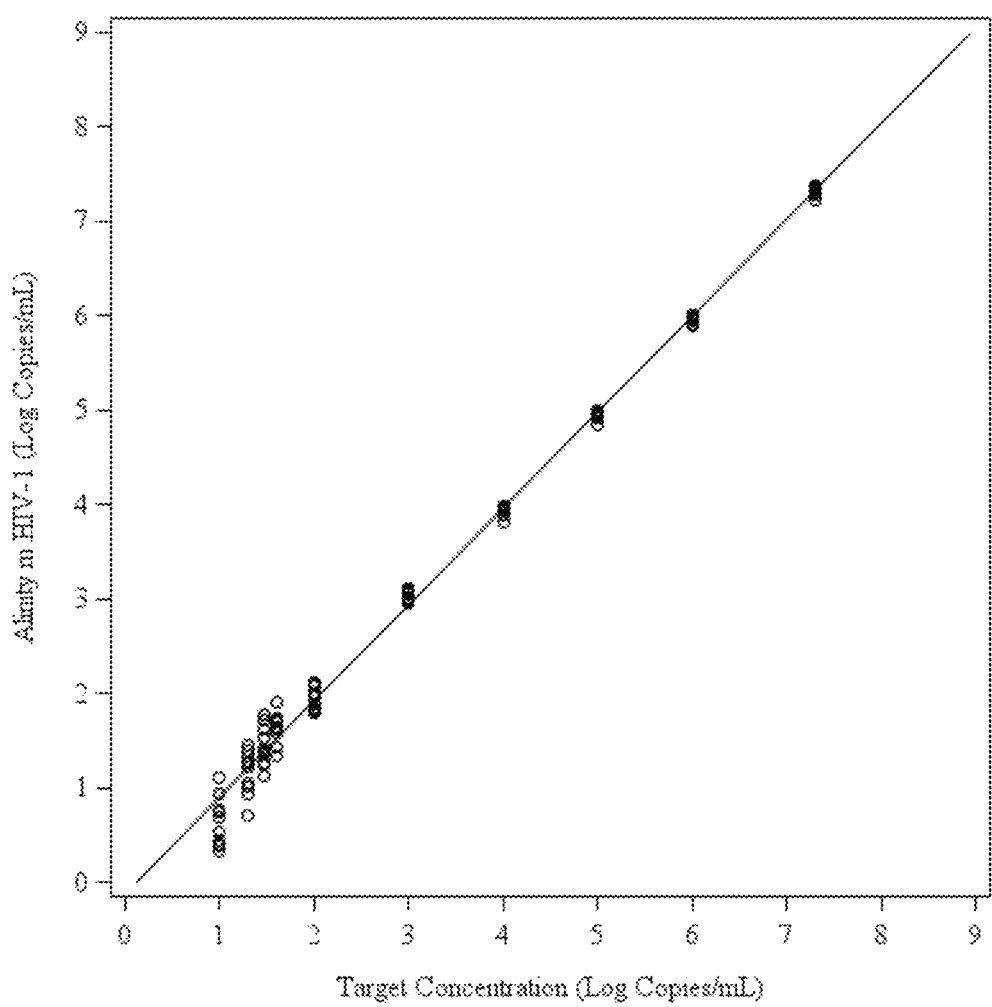
FIG. 10 is a graph of ALINITY m™ HIV-1 Group M, subtype A linearity least-squares regression plot for panel members within the linear range.
Figure 11:
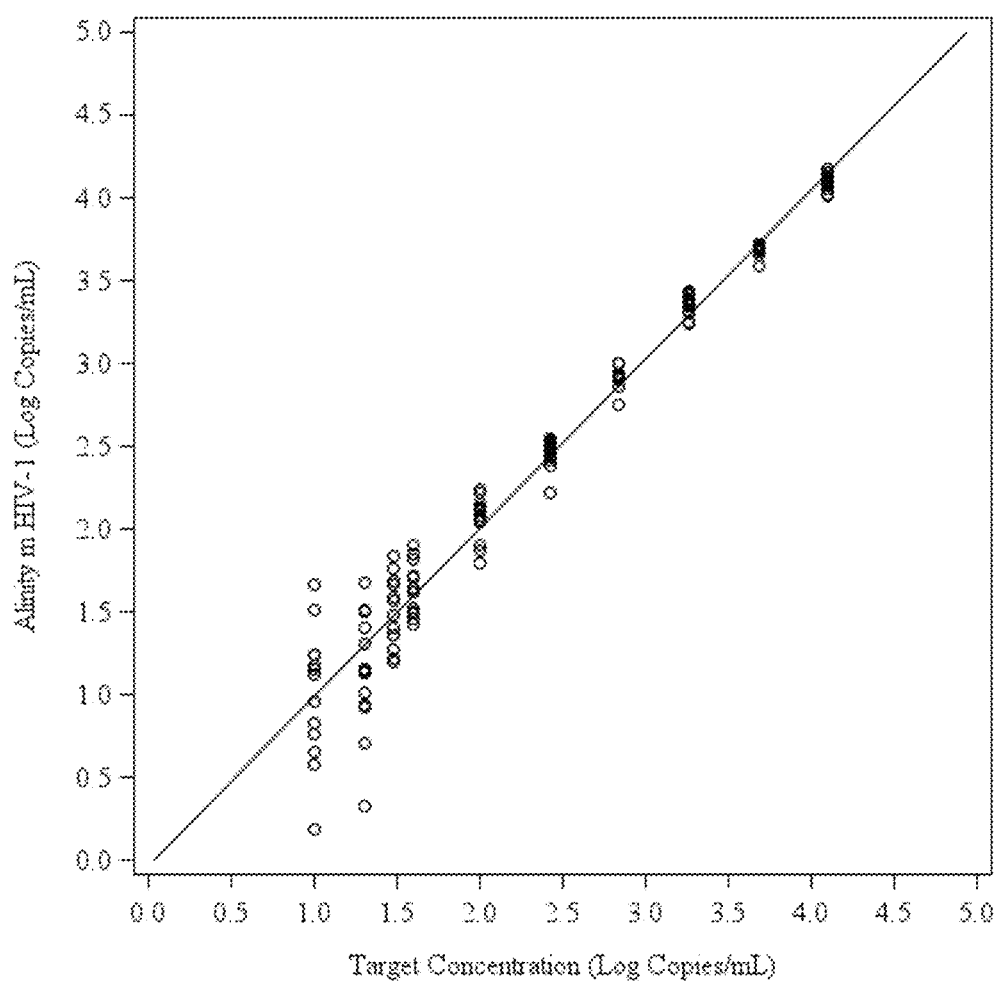
FIG. 11 is a plot of ALINITY m™ HIV-1 Group M, subtype BF linearity least-squares regression for panel members within the linear range.
Figure 12:
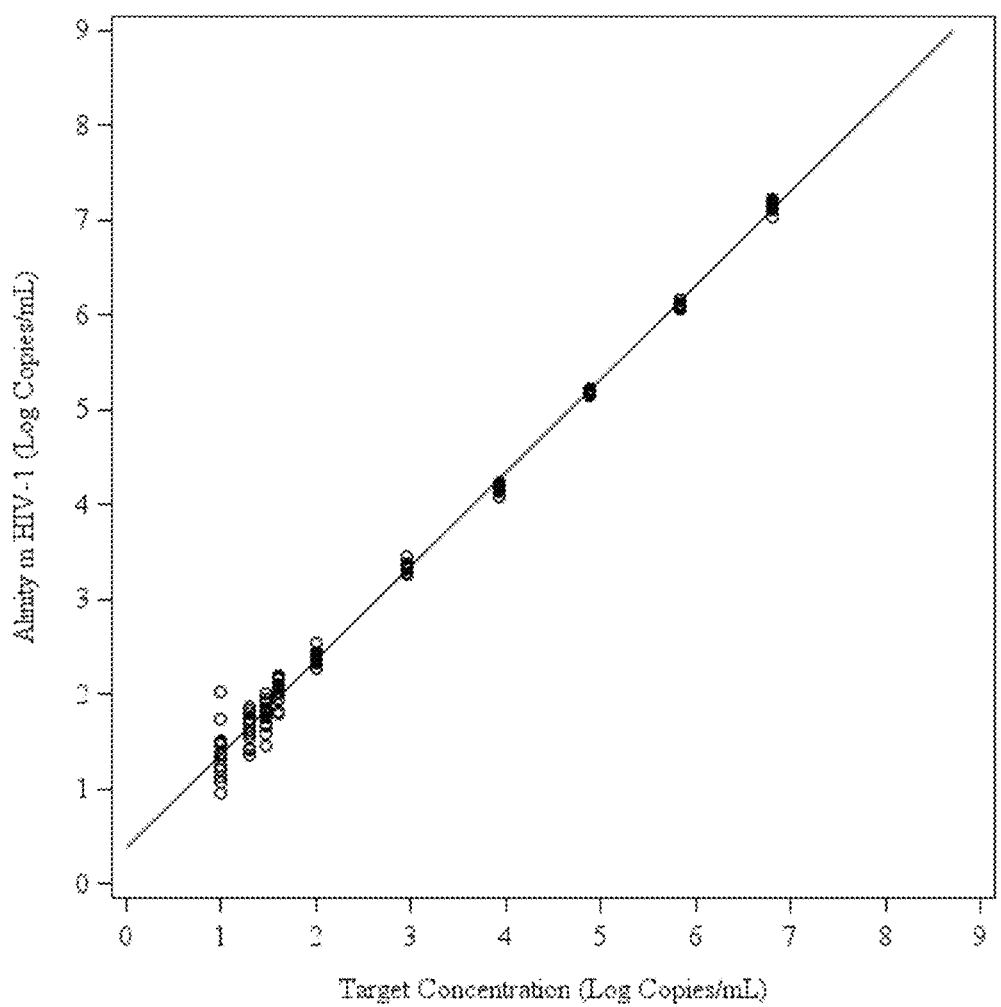
FIG. 12 is a plot of ALINITY m™ HIV-1 Group M, subtype C linearity least-squares regression for panel members within the linear range with outliers removed.
Figure 13:
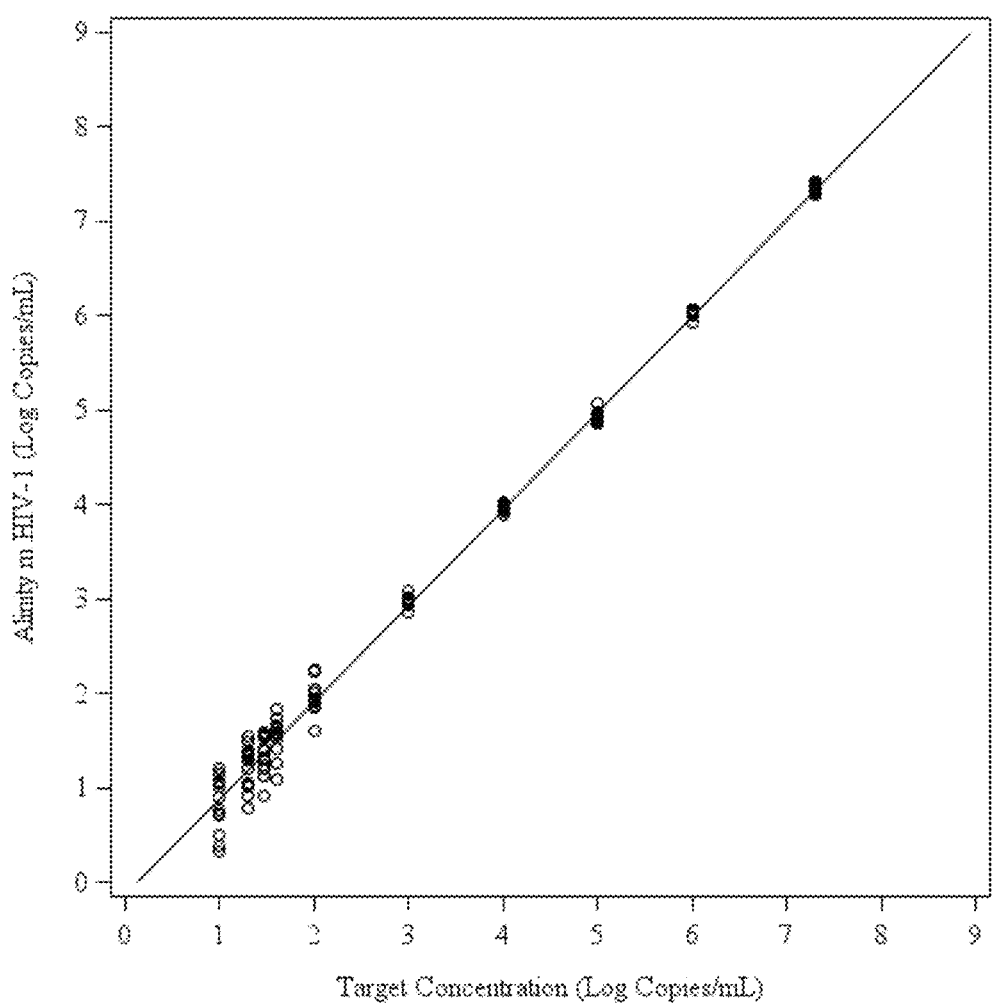
FIG. 13 is a plot of ALINITY m™ HIV-1 Group M, subtype D linearity least-squares regression for panel members within the linear range.
Figure 14:
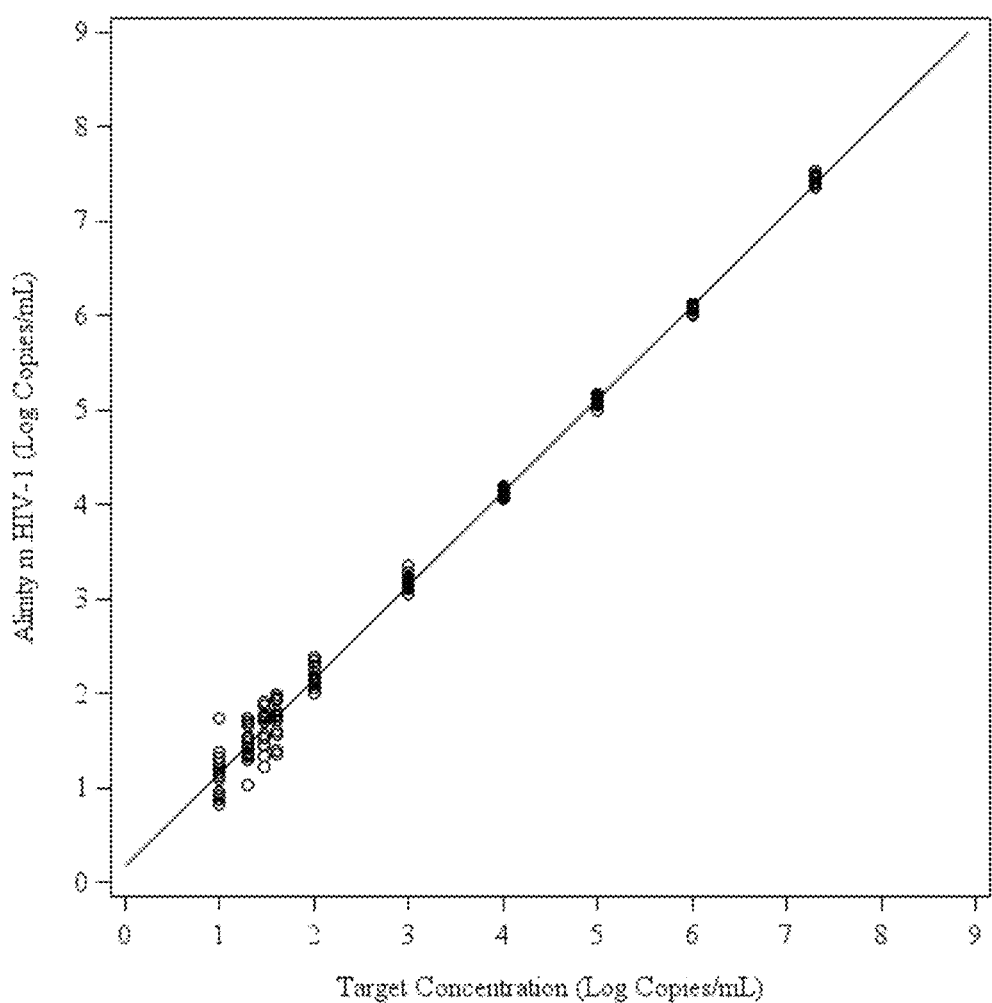
FIG. 14 is a plot of ALINITY m™ HIV-1 Group M, subtype AE linearity least-squares regression for panel members within the linear range.
Figure 15:
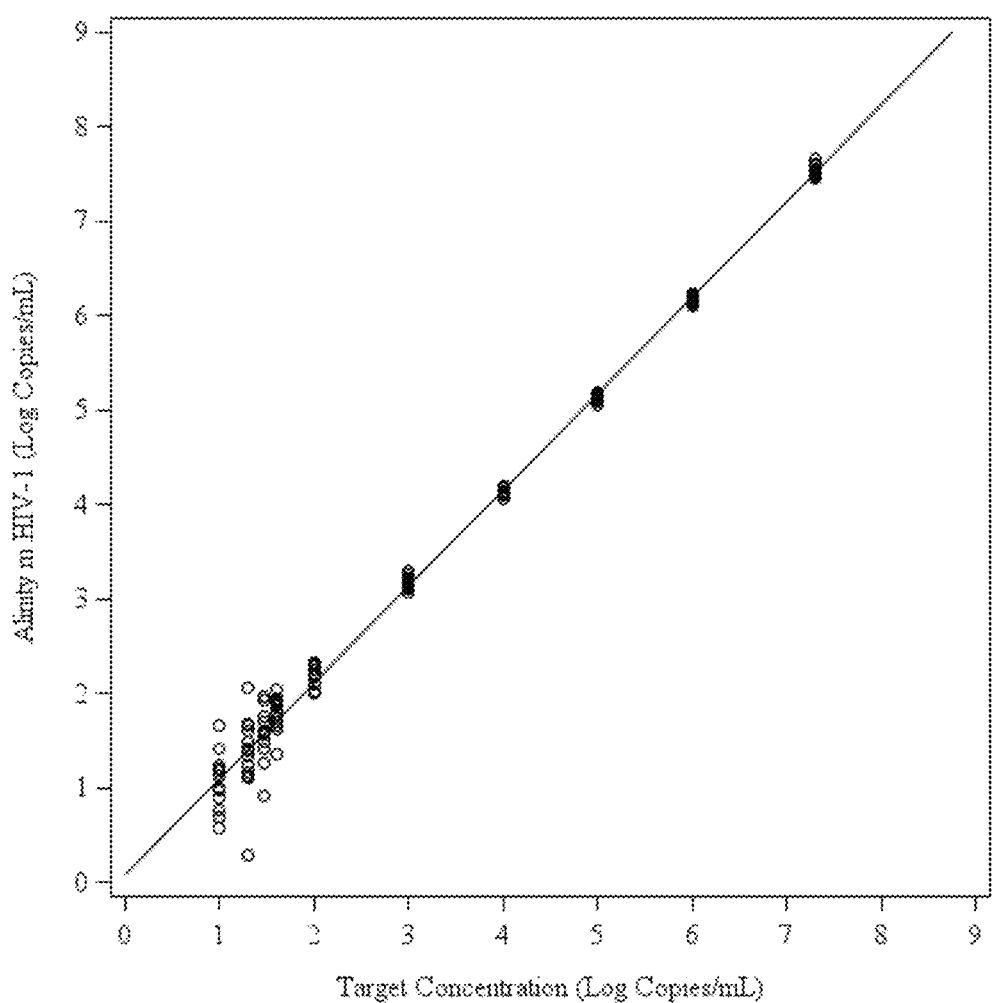
FIG. 15 is plot of ALINITY m™ HIV-1 Group M, subtype AG linearity least-squares regression for panel members within the linear range.
Figure 16:
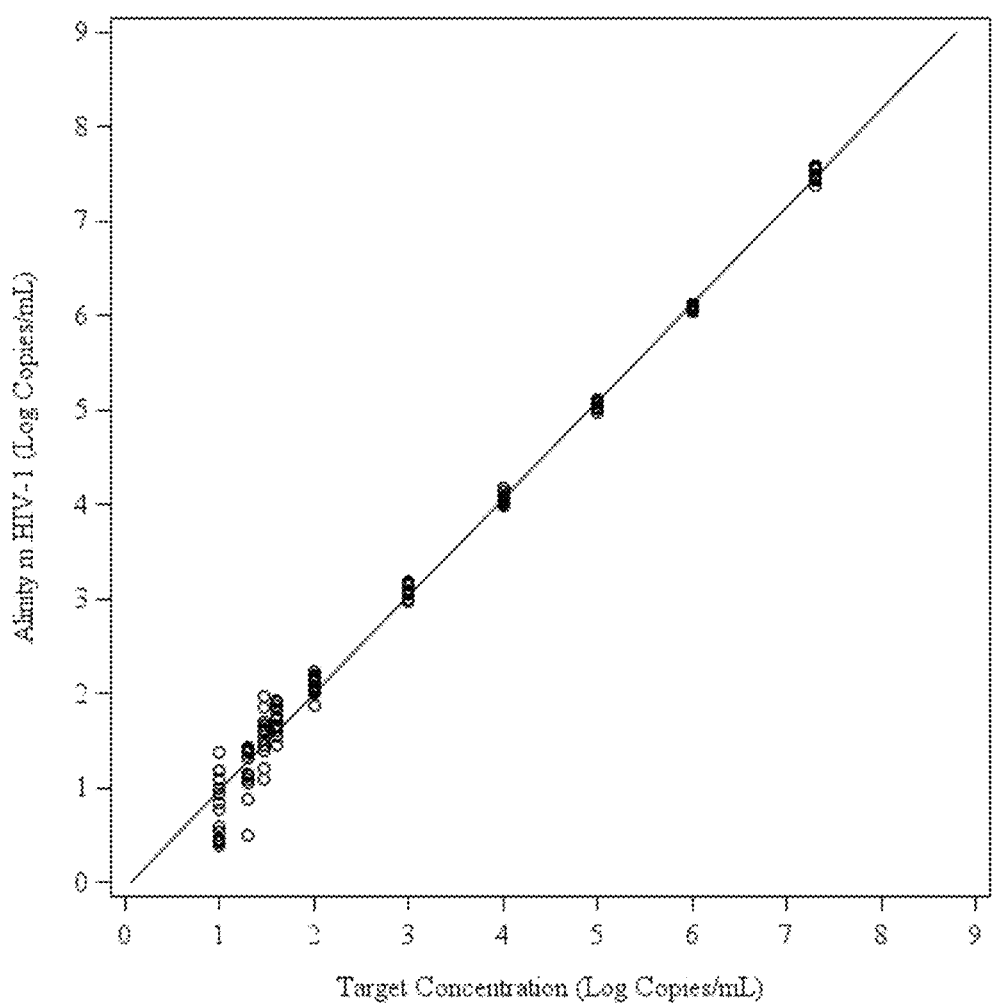
FIG. 16 is a plot of ALINITY m™ HIV-1 Group M, subtype F linearity least-squares regression for panel members within the linear range.
Figure 17:
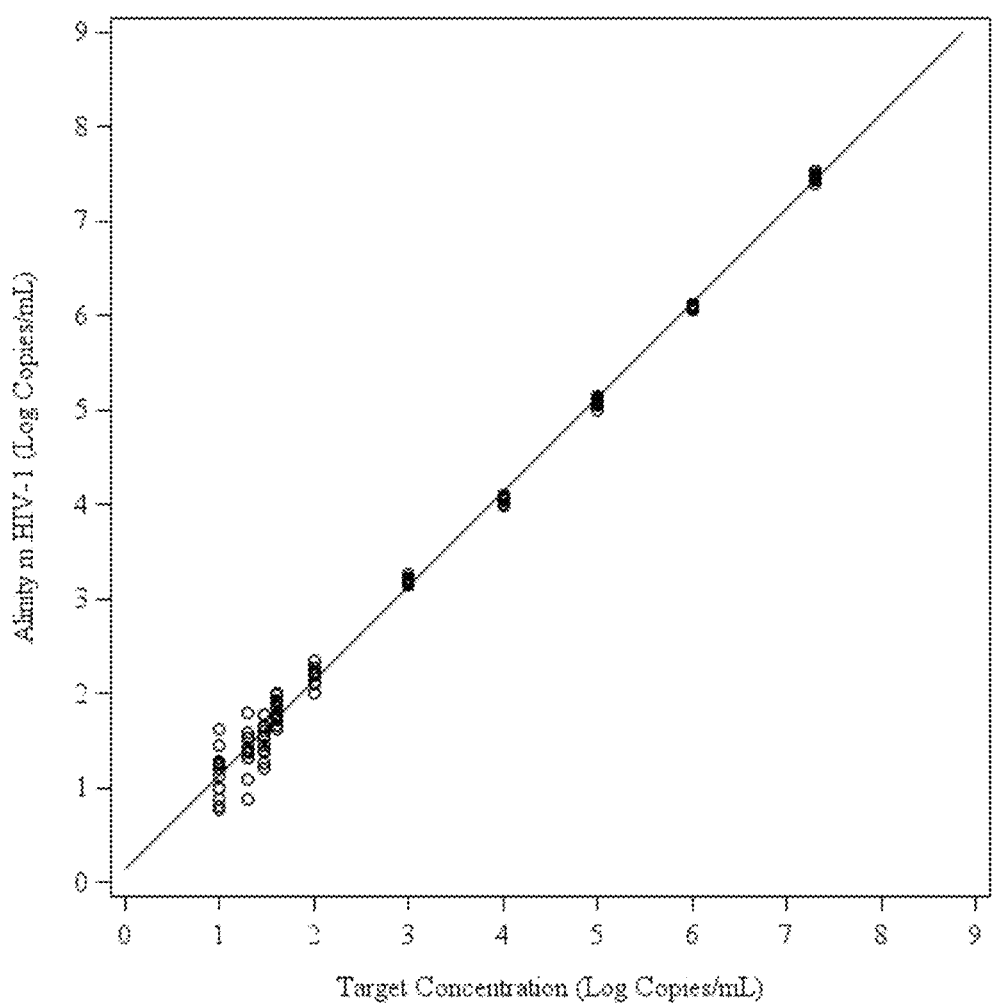
FIG. 17 is a plot of ALINITY m™ HIV-1 Group M, subtype G linearity least-squares regression for panel members within the linear range.
Figure 18:
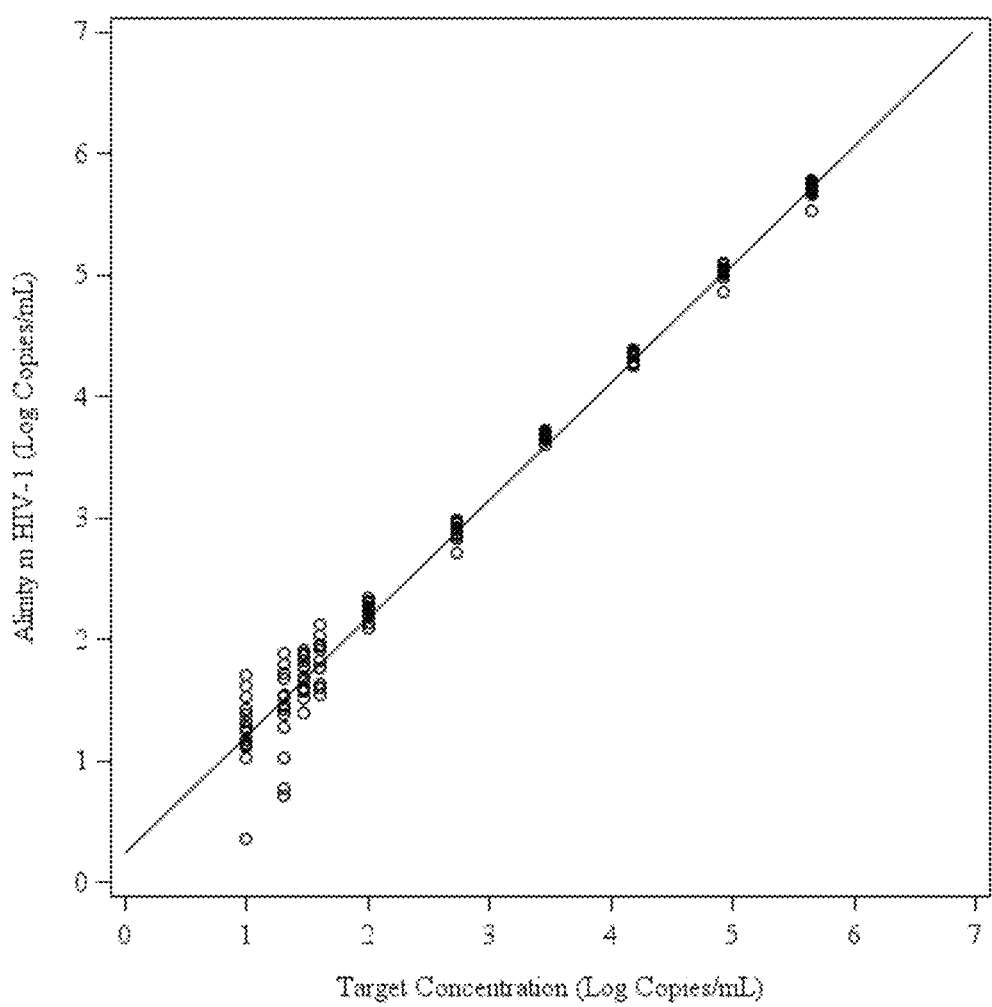
FIG. 18 is a plot of ALINITY m™ HIV-1 Group M, subtype H linearity least-squares regression for panel members within the linear range.
Figure 19:
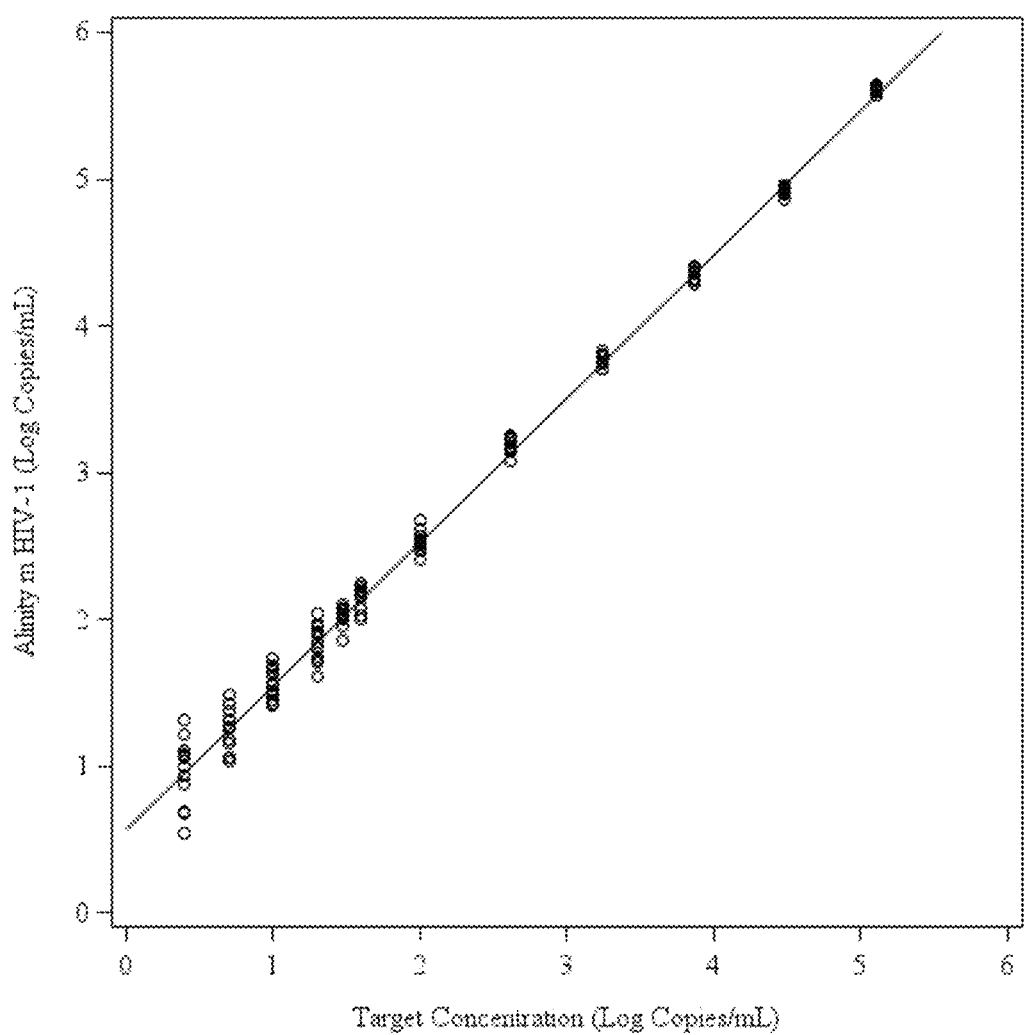
FIG. 19 is a plot of ALINITY m™ HIV-1 Group N linearity least-squares regression for panel members within the linear range.
Figure 20:
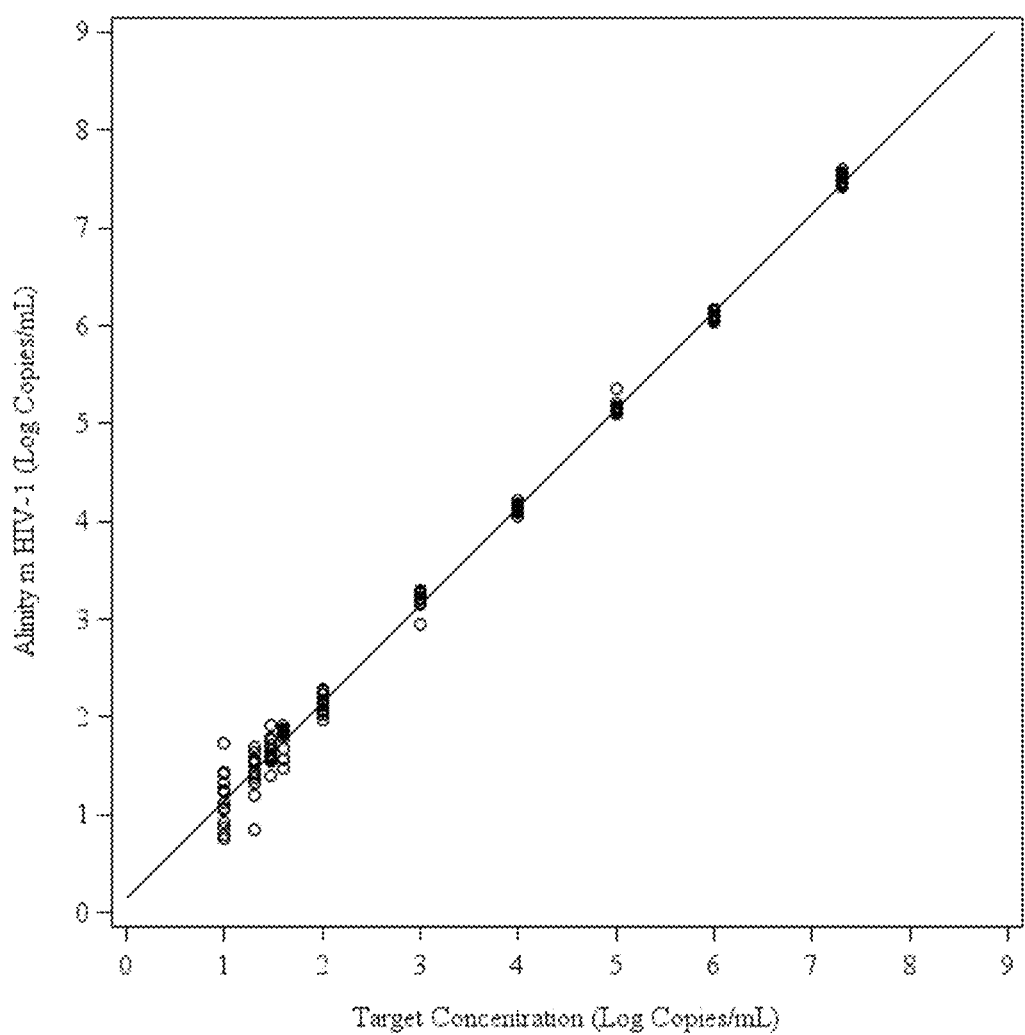
FIG. 20 is a plot of ALINITY m™ HIV-1 Group O linearity least-squares regression for panel members within the linear range.

The ALINITY m™ HIV-1 assay was defined to be linear within the lowest virus panel member tested (targeted 10 copies/mL) and the highest virus panel member tested (targeted 20,000,000 copies/mL) for the HIV-1 Group M, subtype B virus. The analysis of plasma results showed a non-linear coefficient to be significant. The linear and non-linear regression plots of the ALINITY m™ HIV-1 assay are presented in FIG. 2, and the results supporting FIG. 2 are shown in Table 15 through Table 18. For all panel members, the least-squares regression plot of the ALINITY m™ HIV-1 assay is presented in FIG. 3, and a summary is provided in Table 19. The linearity range is 10 to 20,000,000 copies/mL and is shown in Table 20. A total of 267 results were generated in the study: a total of 264 sample results were included in the analyses, 0 sample results were excluded from the analyses, and 3 valid control results. All test results were reviewed. No results were excluded during the analysis. An overall line-listing summary of the total number of included and excluded sample results, and invalid/valid assay control results is provided in Table 21.

TABLE 15

ALINITY m ™ HIV-1 Linearity Listing of Standard Deviations

| Panel | Target Concentration (copies/mL) | Target Concentration (log copies/mL) | N | SD (log copies/mL) | SD Requirement | Pass/Fail |
|---|---|---|---|---|---|---|
| 01 | 20,000,000 | 7.30 | 24 | 0.053 | 0.25 | Pass |
| 02 | 1,000,000 | 6.00 | 24 | 0.061 | 0.25 | Pass |
| 03 | 100,000 | 5.00 | 24 | 0.050 | 0.25 | Pass |
| 04 | 10,000 | 4.00 | 24 | 0.049 | 0.25 | Pass |
| 05 | 1,000 | 3.00 | 24 | 0.073 | 0.25 | Pass |
| 06 | 100 | 2.00 | 24 | 0.135 | 0.25 | Pass |
| 07 | 40 | 1.60 | 24 | 0.183 | 0.46 | Pass |
| 08 | 30 | 1.50 | 24 | 0.246 | 0.46 | Pass |
| 09 | 20 | 1.30 | 24 | 0.299 | 0.46 | Pass |
| 10 | 15 | 1.18 | 23 | 0.330 | 0.46 | Pass |
| 11 | 10 | 1.00 | 24 | 0.276 | 0.46 | Pass |

TABLE 16

ALINITY m ™ HIV-1 Linearity Listing of Statistical Outliers
Outlier Detected

No

TABLE 17

ALINITY m ™ HIV-1 Linearity Summary of Regression Parameters

| Order of Polynomial | Intercept | Coefficient 1 Value | Coefficient 1 p-value | Coefficient 2 Value | Coefficient 2 p-value | Coefficient 3 Value | Coefficient 3 p-value | Nonlinear Coefficient Significant | MSE (mean square error) |
|---|---|---|---|---|---|---|---|---|---|
| 1 | −0.0530 | 1.0277 | p < 0.0001 | | | | | | 0.0395 |
| 2 | −0.0474 | 1.0234 | p < 0.0001 | 0.0006 | 0.8805 | | | No | 0.0397 |
| 3 | −0.3348 | 1.3442 | p < 0.0001 | −0.0908 | p < 0.01 | 0.0074 | p < 0.01 | Yes | 0.0382 |

TABLE 18

ALINITY m ™ HIV-1 Linearity Listing of Predicted Values and Differences

| Panel | Target Concentration (log copies/mL) | Mean Concentration (log copies/mL) | Linear Predicted Value | Polynomial Predicted Value | Difference of Predicted Value | Linearity Check (<=0.5 log copies/mL) |
|---|---|---|---|---|---|---|
| 01 | 7.30 | 7.51 | 7.45 | 7.50 | 0.05 | Yes |
| 02 | 6.00 | 6.03 | 6.11 | 6.05 | 0.06 | Yes |
| 03 | 5.00 | 5.04 | 5.09 | 5.04 | 0.05 | Yes |
| 04 | 4.00 | 4.06 | 4.06 | 4.06 | 0.00 | Yes |
| 05 | 3.00 | 3.11 | 3.03 | 3.08 | 0.05 | Yes |
| 06 | 2.00 | 2.07 | 2.00 | 2.05 | 0.05 | Yes |
| 07 | 1.60 | 1.62 | 1.59 | 1.61 | 0.02 | Yes |
| 08 | 1.50 | 1.39 | 1.49 | 1.50 | 0.01 | Yes |
| 09 | 1.30 | 1.23 | 1.28 | 1.28 | 0.01 | Yes |
| 10 | 1.18 | 1.25 | 1.16 | 1.13 | 0.02 | Yes |
| 11 | 1.00 | 0.93 | 0.97 | 0.93 | 0.05 | Yes |

TABLE 19

Summary for Panel Members within the Linear Range

| | | | |
|---|---|---|---|
| Sample Size (n)* | | | 263 |
| Correlation Coefficient (r) | | | 0.996 |
| Slope | | | 1.03 |
| 95% CI for Slope | | | (1.02, 1.04) |
| Intercept | | | −0.05 |
| 95% CI for Intercept | | | (−0.10, −0.01) |
| Target Concentration (log copies/mL) | Min | 1.00 | Max 7.30 |
| ALINITY m ™ HIV-1 (log copies/mL) | Min | 0.23 | Max 7.59 |

TABLE 20

Summary of Linear Range

| Limit | Panel | Target Concentration (copies/mL) | Target Concentration (log copies/mL) | Acceptance Criteria |
|---|---|---|---|---|
| Lower | 11 | 10 | 1.00 | Met |
| Upper | 01 | 20,000,000 | 7.30 | Met |

TABLE 21

ALINITY m ™ HIV-1 Linearity Study Overall Line Listing Summary

| Total Number of Results | Number of Control Results Valid | Number of Control Results Invalid | Number of Sample Results Included | Number of Sample Results Excluded |
|---|---|---|---|---|
| 267 | 3 | 0 | 264 | 0 |

The results of this example demonstrate that the ALINITY m™ HIV-1 assay was linear between 10 copies/mL and 20,000,000 copies/mL for HIV-1 Group M, subtype B.

Example 4

The example describes experiments to verify the limit of detection (LOD) of the ALINITY m™ HIV-1 assay for HIV-1 Group M subtypes A, BF, C, D, CRF01-AE, F, CRF02-AG, G, H, Group O, and Group N in plasma samples.

For each HIV-1 Group/subtype, three panel members were prepared by diluting a clinical specimen or viral stock into HIV-1 negative human plasma. Panel concentrations were targeted to bracket and include concentrations at the assay's intended LOD and Lower Limit of Quantitation (LLOQ) at 20 copies/mL. Panel quantitation values were established with the Abbott REALTIME™ HIV-1 assay, which uses internal reference standards that are traceable to a viral standard from the Virology Quality Assurance (VQA) Laboratory of the AIDS Clinical Trial Group (see Table 22).

TABLE 22

HIV-1 Panel Members

| Group/Subtype | Panel Member | Target HIV-1 RNA Concentration log copies/mL | Target HIV-1 RNA Concentration copies/mL |
|---|---|---|---|
| Group M/Subtype A | 1 | 1.00 | 10 |
| | 2 | 1.30 | 20 |
| | 3 | 1.60 | 40 |
| Group M/Subtype BF | 1 | 1.00 | 10 |
| | 2 | 1.30 | 20 |
| | 3 | 1.60 | 40 |

TABLE 22-continued

HIV-1 Panel Members

| Group/Subtype | Panel Member | Target HIV-1 RNA Concentration | |
|---|---|---|---|
| | | log copies/mL | copies/mL |
| Group M/Subtype C | 1 | 1.00 | 10 |
| | 2 | 1.30 | 20 |
| | 3 | 1.60 | 40 |
| Group M/Subtype D | 1 | 1.00 | 10 |
| | 2 | 1.30 | 20 |
| | 3 | 1.60 | 40 |
| Group M/Subtype CRF01-AE | 1 | 1.00 | 10 |
| | 2 | 1.30 | 20 |
| | 3 | 1.60 | 40 |
| Group M/Subtype F | 1 | 1.00 | 10 |
| | 2 | 1.30 | 20 |
| | 3 | 1.60 | 40 |
| Group M/Subtype CRF02-AG | 1 | 1.00 | 10 |
| | 2 | 1.30 | 20 |
| | 3 | 1.60 | 40 |
| Group M/Subtype G | 1 | 1.00 | 10 |
| | 2 | 1.30 | 20 |
| | 3 | 1.60 | 40 |
| Group M/Subtype H | 1 | 1.00 | 10 |
| | 2 | 1.30 | 20 |
| | 3 | 1.60 | 40 |
| Group O | 1 | 1.00 | 10 |
| | 2 | 1.30 | 20 |
| | 3 | 1.60 | 40 |
| Group N | 1 | 1.00 | 10 |
| | 2 | 1.30 | 20 |
| | 3 | 1.60 | 40 |

For each panel member of each group or subtype, three testing runs with one ALINITY m™ HIV-1 amplification reagent lot were performed across multiple days including eight replicates per day (e.g. eight replicates/day×three days=24 total replicates tested). A total of 24 replicates of each panel member were tested. This ensured a minimum of 20 valid replicates per panel member.

The sample size per the recommendation in CLSI EP17-A2 Guideline is a minimum of one reagent lot, one instrument, two samples at the LOD claim, two replicates per sample per day and 20 total low-level replicates. Therefore, the sample size used in this study met the minimum sample size recommended in CLSI EP17-A2 Guideline.

The study was conducted using one lot of ALINITY m™ HIV-1 Amp Kit IUO reagents, one lot of ALINITY m™ HIV-1 CTRL Kit IUO reagents, one lot of ALINITY m™ HIV-1 CAL Kit IUO reagents, one lot of Sample Prep RNA Kit IUO reagents, one lot of ALINITY m™ Lysis Solution IUO, one lot of ALINITY m™ Vapor Barrier Solution IUO, one lot of ALINITY m™ Diluent Solution IUO, and two ALINITY m™ Systems.

Explanation of the Sample Identification Convention

Within the line listing, each line identifies the sample identification (ID) assigned to the tested sample. Calibrators and Controls were named as required by ALINITY m™ instrument software.

The SID was: GDggyyzz
Key: GD=study (Group/Subtype Limit of Detection)
gg=Group, subtype
A1=Group M, subtype A
BF=Group M, subtype BF
C1=Group M, subtype C
D1=Group M, subtype D
AE=Group M, CRF01-AE
F1=Group M, subtype F
AG=Group M, CRF02-AG
G1=Group M, subtype G
H1=Group M, subtype H
O1=Group O
N1=Group N
yy=panel number (01 to XX)
01=10 copies/mL
02=20 copies/mL
03=40 copies/mL
zz=Day (01 to XX)

Example sample IDs used in this study are listed in Table 23 below.

TABLE 23

| Sample ID | Sample Description |
|---|---|
| GDD10303I02 | Group M, subtype D, 40 copies/mL, Day 3 |
| GDH10202I01 | Group M, subtype H, 20 copies/mL, Day 2 |
| GDN10101I03 | Group N, 10 copies/mL, Day 1 |

*The ALINITY m ™ instrument software requires unique SIDs in sequential order to process samples. Additional identifiers were added by the operator to create a unique SID for each sample Calibration and Assay Control Validity Criteria A calibration was established for each combination of ALINITY m™ HIV-1 Amplification Kit lot, Sample Prep Kit lot and ALINITY m™ Lysis Solution lot on each instrument, prior to running the samples. Each calibrator was tested in replicates of three along with one replicate of negative control, low positive control, and high positive control for each reagent lot/instrument used in the study. Calibration curve parameters and each individual control value were evaluated against the validity criteria in the assay-application specification file and passed.

ALINITY m™ HIV-1 assay controls were tested on each day to verify the validity of the assay. Each individual control value was evaluated against the assay-specific validity criteria and passed.

Sample Validity Evaluation

If a sample was invalid, the result was excluded from analysis and retested if necessary to achieve the minimum sample size. If a "no test" occurred (due to technical or instrument errors), the result was excluded from the analysis and repeated if necessary to ensure that the minimum sample size was achieved.

Statistical Analysis

The analysis variable for the statistical analysis is the ALINITY m™ HIV-1 sample's result/interpretation. If the sample's result/interpretation was "Not Detected," then the sample was considered not detected. A sample was considered "Detected" if it had one of the three following result/interpretations: Detected<LLOQ, Within Linear Range, and Concentration>ULOQ.

For each HIV-1 Group/subtype, the detection rate (hit rate) for each panel member was estimated as described in the following equation:

$$\text{Detection Rate} = \frac{\text{Number of Replicates Detected}}{\text{Total Number of Replicates Tested}} \times 100$$

where the Total Number of Replicates is the sum of the "Detected" and "Not Detected" replicates. The upper one-sided 95% score confidence interval (CI) of the detection rate was also calculated.

Acceptance Criteria

For each targeted HIV-1 Group/subtype, the upper one-sided 95% confidence interval for the detection rate (hit rate) shall be greater than or equal to 95.0% for panel members at, and above, 20 copies/mL.

The data verified that the limit of detection (LOD) of the ALINITY m™ HIV-1 assay for HIV-1 Group M subtypes A, BF, C, D, CRF01-AE, F, CRF02-AG, G, H, Group O, and Group N was less than or equal to 20 copies/mL. The results are presented in Tables 24 and 25.

TABLE 24

HIV-1 Group/Subtype Limit of Detection (LOD)

| Group/Subtype | Panel Member | HIV-1 RNA Concentration (copies/mL) | # Replicates Tested | # Replicates Detected | Detection Rate (%) | 95% Conf. Int. (%) |
|---|---|---|---|---|---|---|
| Group M, subtype A | 03 | 40.00 | 24 | 24 | 100.0 | 100.0 |
| Group M, subtype A | 02 | 20.00 | 24 | 24 | 100.0 | 100.0 |
| Group M, subtype A | 01 | 10.00 | 23 | 21 | 91.3 | 97.6 |
| Group M, subtype BF | 03 | 40.00 | 24 | 24 | 100.0 | 100.0 |
| Group M, subtype BF | 02 | 20.00 | 24 | 24 | 100.0 | 100.0 |
| Group M, subtype BF | 01 | 10.00 | 24 | 22 | 91.7 | 97.7 |
| Group M, subtype C | 03 | 40.00 | 24 | 24 | 100.0 | 100.0 |
| Group M, subtype C | 02 | 20.00 | 24 | 24 | 100.0 | 100.0 |
| Group M, subtype C | 01 | 10.00 | 23 | 23 | 100.0 | 100.0 |
| Group M, subtype D | 03 | 40.00 | 24 | 24 | 100.0 | 100.0 |
| Group M, subtype D | 02 | 20.00 | 24 | 24 | 100.0 | 100.0 |
| Group M, subtype D | 01 | 10.00 | 24 | 19 | 79.2 | 90.8 |
| Group M, CRF01-AE | 03 | 40.00 | 24 | 24 | 100.0 | 100.0 |
| Group M, CRF01-AE | 02 | 20.00 | 24 | 24 | 100.0 | 100.0 |
| Group M, CRF01-AE | 01 | 10.00 | 24 | 22 | 91.7 | 97.7 |
| Group M, subtype F | 03 | 40.00 | 24 | 24 | 100.0 | 100.0 |
| Group M, subtype F | 02 | 20.00 | 23 | 23 | 100.0 | 100.0 |
| Group M, subtype F | 01 | 10.00 | 21 | 21 | 100.0 | 100.0 |
| Group M, CRF02-AG | 03 | 40.00 | 23 | 23 | 100.0 | 100.0 |
| Group M, CRF02-AG | 02 | 20.00 | 24 | 24 | 100.0 | 100.0 |
| Group M, CRF02-AG | 01 | 10.00 | 24 | 22 | 91.7 | 97.7 |
| Group M, subtype G | 03 | 40.00 | 24 | 24 | 100.0 | 100.0 |
| Group M, subtype G | 02 | 20.00 | 24 | 24 | 100.0 | 100.0 |
| Group M, subtype G | 01 | 10.00 | 24 | 22 | 91.7 | 97.7 |
| Group M, subtype H | 03 | 40.00 | 24 | 24 | 100.0 | 100.0 |
| Group M, subtype H | 02 | 20.00 | 24 | 24 | 100.0 | 100.0 |
| Group M, subtype H | 01 | 10.00 | 24 | 23 | 95.8 | 99.3 |
| Group O | 03 | 40.00 | 24 | 24 | 100.0 | 100.0 |
| Group O | 02 | 20.00 | 24 | 24 | 100.0 | 100.0 |
| Group O | 01 | 10.00 | 24 | 24 | 100.0 | 100.0 |
| Group N | 03 | 40.00 | 23 | 23 | 100.0 | 100.0 |
| Group N | 02 | 20.00 | 24 | 24 | 100.0 | 100.0 |
| Group N | 01 | 10.00 | 23 | 23 | 100.0 | 100.0 |

TABLE 25

HIV-1 Summary Table of LOD

| Group/Subtype | Acceptance Criteria |
|---|---|
| Group M, subtype A | Met |
| Group M, subtype BF | Met |
| Group M, subtype C | Met |
| Group M, subtype D | Met |
| Group M, CRF01-AE | Met |
| Group M, subtype F | Met |
| Group M, CRF02-AG | Met |
| Group M, subtype G | Met |
| Group M, subtype H | Met |
| Group O | Met |
| Group N | Met |

Excluded data is summarized below. When the minimum sample size was not achieved, retests were performed.

One replicate of Group M, Subtype A 10 copies/mL tested on Day 3 was invalid with Code: 9210 Internal control cycle number is too high. This sample was excluded from analysis and not re-tested as the minimum sample size was achieved.

One replicate of Group M, CRF02-AG 40 copies/mL tested on Day 1 was invalid with Code: 9210 Internal control cycle number is too high. This sample was excluded from analysis and not re-tested as the minimum sample size was achieved.

Eight replicates of Group M, subtype C 10 copies/mL tested on Day 2 were invalid due to instrument error with Code: 120 Unable to process. Status is Stopped. These samples were excluded from analysis as a no test and re-tested.

Four replicates of Group M, subtype C 20 copies/mL tested on Day 2 were invalid due to instrument error with Code: 120 Unable to process. Status is Stopped. These samples were excluded from analysis as a no test and were re-tested.

One replicate of Group M, subtype C 10 copies/mL tested on Day 3 was invalid with Code: 9212 Internal control failed. This sample was excluded from analysis and not re-tested as the minimum sample size was achieved.

Three replicates of Group M, subtype D 40 copies/mL tested on Day 3 were invalid due to instrument error with Code: 5017 Pipettor aspiration error. These samples were excluded from analysis as a no test and re-tested.

One replicate of Group M, subtype F 20 copies/mL tested on Day 2 was invalid due to instrument error with Code: 5017 Pipettor aspiration error. These samples were excluded from analysis as a no test and re-tested.

Four replicates of Group M, subtype D 40 copies/mL tested on Day 3 were invalid due to instrument error with Code: 5018 Pipettor dispense error. These samples were excluded from analysis as a no test and re-tested.

Seven replicates of Group M, subtype F (multiple levels) were invalid due to instrument error with Code: 5013 Liquid level detection error on pipettor probe. These samples were excluded from analysis as a no test and re-tested.

One replicate of Group M, Subtype F 20 copies/mL tested on Day 1 was invalid with Code: 9210 Internal control cycle number is too high. This sample was excluded from analysis and not re-tested.

Twelve replicates of Group M, Subtype H 10 copies/mL tested on Day 2 were invalid due to instrument error with Code: 3024 Contamination check on Amp-Detect unit failed. These samples were excluded from analysis as a no test and re-tested to achieve the minimum sample size.

One replicate of Group N 10 copies/mL tested on Day 3 was invalid due to instrument error with Code: 1993 Signal response exceeds maximum ratio for assay. This sample was excluded from analysis and not re-tested as the minimum sample size was achieved.

One replicate of Group N 40 copies/mL tested on Day 1 was invalid with Code: 9210 Internal control cycle number is too high. This sample was excluded from analysis and not re-tested as the minimum sample size was achieved.

All test results were reviewed. Certain observations may have been excluded from the analysis in accordance with the protocol exclusion criteria (i.e., control or validity criteria failure, instrument errors or problems, acknowledged technologist error, inclusion criteria not met, and/or protocol not followed). All results that were not excluded were eligible for analysis.

An overall line-listing summary of the total number of included and excluded sample results, and invalid/valid assay control results is provided in Table 26. An explanation of excluded observations is summarized in Table 27.

TABLE 26

ALINITY m ™ HIV-1 Group/Subtype Limit of Detection Study
Overall Line Listing Summary

| Total Number of Results | Number of Control Results | | Number of Sample Results | |
|---|---|---|---|---|
| | Valid | Invalid | Included | Excluded |
| 849 | 21 | 0 | 783 | 45 |

TABLE 27

ALINITY m ™ HIV-1 Group/Subtype Limit of Detection Study
Excluded Data Summary

| Exclusion Code | N | OBS Number(s) | Reason for Exclusion | Impact to Study Conclusion |
|---|---|---|---|---|
| 26 - Invalid sample | 5 | 1, 2, 11, 26, 45 | Samples were invalid and excluded from analysis per the protocol. | There is no impact to the study conclusion. The minimum number of replicates for each panel member was met per the protocol. |
| 31 - Instrument error | 40 | 3, 4, 5, 6, 7, 8, 9, 10, 12, 13, 14, 15, 16, 17, 18, 19, 20, 21, 22, 23, 24, 25, 27, 28, 29, 30, 31, 32, 33, 34, 35, 36, 37, 38, 39, 40, 41, 42, 43, 44 | Samples were invalid because of an instrument error during sample preparation | There is no impact to the study conclusion. Testing was performed on a subsequent run, per the protocol. The test results were valid and used for data analysis. |

A total of 849 results were generated in the study: a total of 783 results were included in the analyses, a total of 45 results were excluded from the analyses, and 21 valid controls.

The results of this example demonstrate an LOD of 20 copies/mL for the ALINITY m™ HIV-1 assay using HIV-1 Group M subtypes A, BF, C, D, CRF01-AE, F, CRF02-AG, G, H, Group O, and Group N.

Example 5

This example describes experiments conducted to verify the linear range for the ALINITY m™ HIV-1 assay by testing HIV-1 Group M subtypes A, BF, C, D, CRF01-AE, F, CRF02-AG, G, H, Group O, and Group N linearity panels.

Linearity of the ALINITY m™ HIV-1 assay was evaluated by testing a minimum of 10 panel members for each HIV-1 Group/subtype. Where possible, linearity panel members spanned the intended dynamic range of the assay (20 to 10,000,000 copies/mL). When limitations prevented obtaining certain Groups/subtypes in large enough volumes and/or at high enough concentrations to achieve the upper target level of 20,000,000 copies/mL, high-end dilution panel members were prepared at the highest concentration possible.

The linearity panels for HIV-1 Group M, subtypes A, C, D, AE, F, AG, G, H, Group O, and Group N were prepared by diluting cultured virus in HIV-1 negative human plasma. The linearity panel for HIV-1 Group M, subtype BF was prepared by diluting an HIV-1 Group M, subtype BF positive patient specimen in HIV-1 negative human plasma.

Panel quantitation values were established with the Abbott REALTIME™ HIV-1 assay, which uses internal reference standards that are traceable to a viral standard from the Virology Quality Assurance (VQA) Laboratory of the AIDS Clinical Trial Group (see Table 28).

TABLE 28

HIV-1 Subtype Linearity Panels

| Group/Subtype | Panel Member | log copies/mL | Target Source |
|---|---|---|---|
| Group M, Subtype A | 1 | 1 | Cultured Virus |
| | 2 | 1.3 | Cultured Virus |
| | 3 | 1.48 | Cultured Virus |
| | 4 | 1.6 | Cultured Virus |
| | 5 | 2 | Cultured Virus |
| | 6 | 3 | Cultured Virus |
| | 7 | 4 | Cultured Virus |
| | 8 | 5 | Cultured Virus |
| | 9 | 6 | Cultured Virus |
| | 10 | 7.3 | Cultured Virus |
| Group M, Subtype BF | 1 | 1 | Clinical Specimen |
| | 2 | 1.3 | Clinical Specimen |
| | 3 | 1.48 | Clinical Specimen |
| | 4 | 1.6 | Clinical Specimen |
| | 5 | 2 | Clinical Specimen |
| | 6 | 2.42 | Clinical Specimen |
| | 7 | 2.84 | Clinical Specimen |
| | 8 | 3.26 | Clinical Specimen |
| | 9 | 3.68 | Clinical Specimen |
| | 10 | 4.1 | Clinical Specimen |
| Group M, Subtype C | 1 | 1 | Cultured Virus |
| | 2 | 1.3 | Cultured Virus |
| | 3 | 1.48 | Cultured Virus |
| | 4 | 1.6 | Cultured Virus |
| | 5 | 2 | Cultured Virus |
| | 6 | 2.96 | Cultured Virus |
| | 7 | 3.92 | Cultured Virus |
| | 8 | 4.88 | Cultured Virus |
| | 9 | 5.84 | Cultured Virus |
| | 10 | 6.8 | Cultured Virus |
| Group M, Subtype D | 1 | 1 | Cultured Virus |
| | 2 | 1.3 | Cultured Virus |
| | 3 | 1.48 | Cultured Virus |
| | 4 | 1.6 | Cultured Virus |
| | 5 | 2 | Cultured Virus |
| | 6 | 3 | Cultured Virus |
| | 7 | 4 | Cultured Virus |
| | 8 | 5 | Cultured Virus |
| | 9 | 6 | Cultured Virus |
| | 10 | 7.3 | Cultured Virus |
| Group M, Subtype AE | 1 | 1 | Cultured Virus |
| | 2 | 1.3 | Cultured Virus |
| | 3 | 1.48 | Cultured Virus |
| | 4 | 1.6 | Cultured Virus |
| | 5 | 2 | Cultured Virus |
| | 6 | 3 | Cultured Virus |
| | 7 | 4 | Cultured Virus |
| | 8 | 5 | Cultured Virus |
| | 9 | 6 | Cultured Virus |
| | 10 | 7.3 | Cultured Virus |
| Group M, Subtype F | 1 | 1 | Cultured Virus |
| | 2 | 1.3 | Cultured Virus |
| | 3 | 1.48 | Cultured Virus |
| | 4 | 1.6 | Cultured Virus |
| | 5 | 2 | Cultured Virus |
| | 6 | 3 | Cultured Virus |
| | 7 | 4 | Cultured Virus |
| | 8 | 5 | Cultured Virus |
| | 9 | 6 | Cultured Virus |
| | 10 | 7.3 | Cultured Virus |
| Group M, Subtype AG | 1 | 1 | Cultured Virus |
| | 2 | 1.3 | Cultured Virus |
| | 3 | 1.48 | Cultured Virus |
| | 4 | 1.6 | Cultured Virus |
| | 5 | 2 | Cultured Virus |
| | 6 | 3 | Cultured Virus |
| | 7 | 4 | Cultured Virus |
| | 8 | 5 | Cultured Virus |
| | 9 | 6 | Cultured Virus |
| | 10 | 7.3 | Cultured Virus |
| Group M, Subtype G | 1 | 1 | Cultured Virus |
| | 2 | 1.3 | Cultured Virus |
| | 3 | 1.48 | Cultured Virus |
| | 4 | 1.6 | Cultured Virus |
| | 5 | 2 | Cultured Virus |
| | 6 | 3 | Cultured Virus |
| | 7 | 4 | Cultured Virus |
| | 8 | 5 | Cultured Virus |
| | 9 | 6 | Cultured Virus |
| | 10 | 7.3 | Cultured Virus |
| Group M, Subtype H | 1 | 1 | Cultured Virus |
| | 2 | 1.3 | Cultured Virus |
| | 3 | 1.48 | Cultured Virus |
| | 4 | 1.6 | Cultured Virus |
| | 5 | 2 | Cultured Virus |
| | 6 | 2.73 | Cultured Virus |
| | 7 | 3.46 | Cultured Virus |
| | 8 | 4.19 | Cultured Virus |
| | 9 | 4.92 | Cultured Virus |
| | 10 | 5.65 | Cultured Virus |
| Group O | 1 | 1 | Cultured Virus |
| | 2 | 1.3 | Cultured Virus |
| | 3 | 1.48 | Cultured Virus |
| | 4 | 1.6 | Cultured Virus |
| | 5 | 2 | Cultured Virus |
| | 6 | 3 | Cultured Virus |
| | 7 | 4 | Cultured Virus |
| | 8 | 5 | Cultured Virus |
| | 9 | 6 | Cultured Virus |
| | 10 | 7.3 | Cultured Virus |

TABLE 28-continued

HIV-1 Subtype Linearity Panels

| Group/Subtype | Panel Member | log copies/mL | Target Source |
|---|---|---|---|
| Group N | 1 | 0.4 | Cultured Virus |
| | 2 | 0.7 | Cultured Virus |
| | 3 | 1 | Cultured Virus |
| | 4 | 1.3 | Cultured Virus |
| | 5 | 1.48 | Cultured Virus |
| | 6 | 1.6 | Cultured Virus |
| | 7 | 2 | Cultured Virus |
| | 8 | 2.62 | Cultured Virus |
| | 9 | 3.24 | Cultured Virus |
| | 8 | 3.86 | Cultured Virus |
| | 11 | 4.48 | Cultured Virus |
| | 12 | 5.1 | Cultured Virus |

The study design was based on the recommendations in Clinical and Laboratory Standards Institute (CLSI) titled "EP06-A, Evaluation of the Linearity of Quantitative Measurement Procedures: A Statistical Approach."

Per the study protocol, the minimum sample size for the study was seven or more panel members and 12 or more replicates per panel member. Therefore, the sample size used in this study met or exceeded the minimum sample size recommended in CLSI EP06-A Guideline.

The study was conducted using two lots of ALINITY m™ HIV-1 Amplification Kits, one lot of Calibrator Kit, two lots of Control Kit, three lots of Sample Prep RNA Kit reagents, one lot of ALINITY m™ Lysis Solution, three lots of ALINITY m™ Diluent Solution, and two lots of ALINITY m™ Vapor Barrier Solution on three ALINITY m™ Systems. For each HIV-1 Group/subtype, one lot of ALINITY m™ HIV-1 Amp Kit reagents were tested on one ALINITY m™ instrument.

Explanation of the Sample Identification Convention

Within the line listing, each line identifies the sample identification (SID) assigned to the tested sample. Calibrators and Controls were named as required by ALINITY m™ instrument software.

The SID was: GLssyy.
The keys: GL=study (Group/Subtype Linearity)
ss=Group, subtype
A1=Group M, subtype A
BF=Group M, subtype BF
C1=Group M, subtype C
D1=Group M, subtype D
AE=Group M, CRF01-AE
F1=Group M, subtype F
AG=Group M, CRF02-AG
G1=Group M, subtype G
H1=Group M, subtype H
O1=Group O
N1=Group N
yy=panel number (01 to XX)

Example sample IDs used in this study are listed in Table 29 below.

TABLE 29

| Sample ID | Sample Description |
|---|---|
| GLA103I01 | Subtype A Panel Member 3 |
| GLAG05I01 | Subtype AG Panel Member 5 |

Note:
Following the panel number, additional characters were included to uniquely identify replicates, not for the purposes of analysis Calibration and Assay Control Validity Criteria A calibration was established for each combination of ALINITY m™ HIV-1 Amplification Kit lot, Sample Prep Kit lot and ALINITY m™ Lysis Solution lot on each instrument prior to running the samples. Each calibrator was tested in replicates of three along with one replicate of Negative Control, Low Positive Control, and High Positive Control for each reagent lot/instrument used in the study. Calibration curve parameters and each individual control value were evaluated against the validity criteria in the assay-application specification file and passed. ALINITY m™ HIV-1 assay controls were tested on each testing day to verify assay validity. Each individual control value was evaluated against the assay-specific validity criteria or equivalent and passed.

Sample Validity Evaluation

If a sample was invalid, the result was excluded from analysis and retested if necessary to achieve the minimum sample size. If all the retest replicates were valid, the retest results were included in the analysis along with any valid results from the original testing.

If a "no test" occurred (due to technical or instrument errors), the result was excluded from the analysis and repeated if necessary to ensure that the minimum sample size is achieved.

Statistical Analysis

The analysis variable for the statistical analysis is the ALINITY m™ HIV-1 concentration log copies/mL. The following analytical steps were performed for each Group/subtype:

a) For each panel level, the standard deviation (SD) of ALINITY m™ HIV-1 results were calculated and the SD confirmed not to be greater than the following requirements for assay precision:
   0.25 log copies/mL from 100 copies/mL to 10,000,000 copies/mL or higher.
   0.46 log copies/mL at less than or equal to 60 copies/mL (3 times the assay's intended LLOQ).
   If the SD met the above criteria then the analyses continued to step b) through g).

b) Outlier Identification:
   Outliers were detected and excluded by checking if any ALINITY m™ HIV-1 result was outside the mean±4×SD range for any panel. The following analyses (step c-step g) were performed with and without outlier.

c) Performed the first, second, and third order polynomial least-square regression. Test if the nonlinear coefficients were significant at significance level 0.05.

d) If there was no significant nonlinear coefficient, then the assay was defined as linear within the range encompassed by the panel members. Continue to step f).

e) If there was a significant nonlinear coefficient, then the nonlinear regression model with the lowest Mean Square Error (MSE) as the fitted nonlinear model was chosen and the difference in the predicted concentration (Y) between the fitted nonlinear model and the linear model for each panel member was calculated.
   If the difference in the predicted concentration (Y) between the fitted nonlinear model and the linear model for the panel member with the lowest and/or highest target concentration was greater than 0.5 log IU/mL, then the panel member with the greater difference was removed. Continue to step c).

If the difference in the predicted concentration (Y) between the fitted nonlinear model and the linear model for each panel member was less than or equal to 0.5 log IU/mL, then:

The lower limit of the linear range was defined as the target concentration of the panel member with the lowest target concentration, The upper limit of the linear range was defined as the target concentration of the panel member with the highest target concentration, and The assay was defined as linear within the lower limit of the linear range and the upper limit of the linear range.

Note that the maximum allowable difference between polynomial and linear models (0.5 log copies/mL) is taken from *The Panel on Antiretroviral Guidelines for Adults and Adolescents. Guidelines for the use of antiretroviral agents in HIV-1-infected adults and adolescents. Department of Health and Human Services* (2014), which states that the minimal change in viral load considered to be statistically significant (2 standard deviations) is a threefold, or a 0.5 log copies/mL change.

f) Performed a least-square linear regression and generate a regression plot including the panel members that were within the linear range determined from step d) or step e).

g) If there was significant nonlinear coefficient from the regression analysis with all panel members, a plot for all panel members using the individual ALINITY m™ HIV-1 results as the Y-axis and the target concentration as the X-axis was generated. Two different symbols representing the results within and out of the linear range were presented on the plot. Two lines representing the predicted mean concentrations from the fitted nonlinear model and the linear model were also presented on the plot. The panel member(s) that were outside of the linear range were highlighted on the plot. For each Group/subtype, the linear equation from the least-square linear regression was reported and the maximum difference was calculated in predicted mean concentrations from the best fitting nonlinear regression and the linear regression. If there was no significant nonlinear coefficient from the regression analysis, "NA" was reported for the maximum difference.

In addition, the least-square linear regression line for each Group/subtype was plotted with all Group/subtypes, including Group M, subtype B, on the same graph.

Acceptance Criteria

For each HIV-1 Group/subtype, the acceptance criteria for this study was the upper limit of the linear range shall be greater than or equal to 10,000,000 copies/mL and the lower limit of the linear range shall be less than or equal to 20 copies/mL.

For any Group/subtype where the panel member did not achieve 10,000,000 copies/mL due to limitations in available volume and/or concentration, the acceptance criteria was the assay shall be linear from the highest panel level tested to less than or equal to 20 copies/mL.

The ALINITY m™ HIV-1 assay was determined to be linear for each HIV-1 Group/subtype from the lowest panel member tested to the highest panel member tested. The analysis of results from Group M, subtypes A, BF, C, AG, F, and G showed a non-linear coefficient to be significant. The linear and non-linear regression plots of the ALINITY m™ HIV-1 assay with these panels are presented in FIGS. 4, 5, 6, 7, 8, and 9. The results supporting FIGS. 4-9 are shown in Table 30 through Table 33.

TABLE 30

List of Standard Deviations for HIV-1 Group/subtypes

| Group/Subtype | Panel | Target Concentration (copies/mL) | Target Concentration (log copies/mL) | N* | SD (log copies/mL) | SD Requirement | Pass/Fail |
|---|---|---|---|---|---|---|---|
| Group M, subtype A | 01 | 10.0 | 1.00 | 11 | 0.259 | 0.46 | Pass |
| | 02 | 20.0 | 1.30 | 12 | 0.218 | 0.46 | Pass |
| | 03 | 30.0 | 1.48 | 13 | 0.207 | 0.46 | Pass |
| | 04 | 40.0 | 1.60 | 12 | 0.147 | 0.46 | Pass |
| | 05 | 100.0 | 2.00 | 12 | 0.113 | 0.25 | Pass |
| | 06 | 1,000.0 | 3.00 | 12 | 0.051 | 0.25 | Pass |
| | 07 | 10,000.0 | 4.00 | 12 | 0.052 | 0.25 | Pass |
| | 08 | 100,000.0 | 5.00 | 12 | 0.044 | 0.25 | Pass |
| | 09 | 1,000,000.0 | 6.00 | 12 | 0.038 | 0.25 | Pass |
| | 10 | 20,000,000.0 | 7.30 | 12 | 0.043 | 0.25 | Pass |
| Group M, subtype BF | 01 | 10.0 | 1.00 | 13 | 0.400 | 0.46 | Pass |
| | 02 | 20.0 | 1.30 | 13 | 0.364 | 0.46 | Pass |
| | 03 | 30.0 | 1.48 | 13 | 0.210 | 0.46 | Pass |
| | 04 | 40.0 | 1.60 | 14 | 0.149 | 0.46 | Pass |
| | 05 | 100.0 | 2.00 | 14 | 0.128 | 0.25 | Pass |
| | 06 | 263.0 | 2.42 | 14 | 0.086 | 0.25 | Pass |
| | 07 | 691.8 | 2.84 | 14 | 0.064 | 0.25 | Pass |
| | 08 | 1,819.7 | 3.26 | 14 | 0.060 | 0.25 | Pass |
| | 09 | 4,786.3 | 3.68 | 13 | 0.037 | 0.25 | Pass |
| | 10 | 12,589.3 | 4.10 | 14 | 0.049 | 0.25 | Pass |
| Group M, subtype C | 01 | 10.0 | 1.00 | 14 | 0.278 | 0.46 | Pass |
| | 02 | 20.0 | 1.30 | 12 | 0.170 | 0.46 | Pass |
| | 03 | 30.0 | 1.48 | 14 | 0.148 | 0.46 | Pass |
| | 04 | 40.0 | 1.60 | 14 | 0.121 | 0.46 | Pass |
| | 05 | 100.0 | 2.00 | 14 | 0.069 | 0.25 | Pass |
| | 06 | 912.0 | 2.96 | 14 | 0.047 | 0.25 | Pass |
| | 07 | 8,317.6 | 3.92 | 13 | 0.045 | 0.25 | Pass |
| | 08 | 75,857.8 | 4.88 | 14 | 0.021 | 0.25 | Pass |
| | 09 | 691,831.0 | 5.84 | 14 | 0.032 | 0.25 | Pass |
| | 10 | 6,309,573.4 | 6.80 | 13 | 0.049 | 0.25 | Pass |

TABLE 30-continued

List of Standard Deviations for HIV-1 Group/subtypes

| Group/Subtype | Panel | Target Concentration (copies/mL) | Target Concentration (log copies/mL) | N* | SD (log copies/mL) | SD Requirement | Pass/Fail |
|---|---|---|---|---|---|---|---|
| Group M, subtype D | 01 | 10.0 | 1.00 | 13 | 0.301 | 0.46 | Pass |
| | 02 | 20.0 | 1.30 | 14 | 0.223 | 0.46 | Pass |
| | 03 | 30.0 | 1.48 | 14 | 0.194 | 0.46 | Pass |
| | 04 | 40.0 | 1.60 | 14 | 0.189 | 0.46 | Pass |
| | 05 | 100.0 | 2.00 | 13 | 0.163 | 0.25 | Pass |
| | 06 | 1,000.0 | 3.00 | 14 | 0.048 | 0.25 | Pass |
| | 07 | 10,000.0 | 4.00 | 14 | 0.036 | 0.25 | Pass |
| | 08 | 100,000.0 | 5.00 | 13 | 0.058 | 0.25 | Pass |
| | 09 | 1,000,000.0 | 6.00 | 13 | 0.036 | 0.25 | Pass |
| | 10 | 20,000,000.0 | 7.30 | 14 | 0.040 | 0.25 | Pass |
| Group M, subtype AE | 01 | 10.0 | 1.00 | 13 | 0.245 | 0.46 | Pass |
| | 02 | 20.0 | 1.30 | 13 | 0.199 | 0.46 | Pass |
| | 03 | 30.0 | 1.48 | 13 | 0.210 | 0.46 | Pass |
| | 04 | 40.0 | 1.60 | 13 | 0.209 | 0.46 | Pass |
| | 05 | 100.0 | 2.00 | 14 | 0.109 | 0.25 | Pass |
| | 06 | 1,000.0 | 3.00 | 14 | 0.077 | 0.25 | Pass |
| | 07 | 10,000.0 | 4.00 | 13 | 0.036 | 0.25 | Pass |
| | 08 | 100,000.0 | 5.00 | 13 | 0.047 | 0.25 | Pass |
| | 09 | 1,000,000.0 | 6.00 | 13 | 0.042 | 0.25 | Pass |
| | 10 | 20,000,000.0 | 7.30 | 13 | 0.050 | 0.25 | Pass |
| Group M, subtype AG | 01 | 10.0 | 1.00 | 14 | 0.305 | 0.46 | Pass |
| | 02 | 20.0 | 1.30 | 14 | 0.409 | 0.46 | Pass |
| | 03 | 30.0 | 1.48 | 13 | 0.271 | 0.46 | Pass |
| | 04 | 40.0 | 1.60 | 14 | 0.176 | 0.46 | Pass |
| | 05 | 100.0 | 2.00 | 14 | 0.103 | 0.25 | Pass |
| | 06 | 1,000.0 | 3.00 | 14 | 0.059 | 0.25 | Pass |
| | 07 | 10,000.0 | 4.00 | 14 | 0.040 | 0.25 | Pass |
| | 08 | 100,000.0 | 5.00 | 14 | 0.033 | 0.25 | Pass |
| | 09 | 1,000,000.0 | 6.00 | 14 | 0.040 | 0.25 | Pass |
| | 10 | 20,000,000.0 | 7.30 | 14 | 0.057 | 0.25 | Pass |
| Group M, subtype F | 01 | 10.0 | 1.00 | 14 | 0.334 | 0.46 | Pass |
| | 02 | 20.0 | 1.30 | 13 | 0.269 | 0.46 | Pass |
| | 03 | 30.0 | 1.48 | 14 | 0.231 | 0.46 | Pass |
| | 04 | 40.0 | 1.60 | 13 | 0.144 | 0.46 | Pass |
| | 05 | 100.0 | 2.00 | 14 | 0.092 | 0.25 | Pass |
| | 06 | 1,000.0 | 3.00 | 13 | 0.073 | 0.25 | Pass |
| | 07 | 10,000.0 | 4.00 | 13 | 0.051 | 0.25 | Pass |
| | 08 | 100,000.0 | 5.00 | 13 | 0.042 | 0.25 | Pass |
| | 09 | 1,000,000.0 | 6.00 | 12 | 0.035 | 0.25 | Pass |
| | 10 | 20,000,000.0 | 7.30 | 13 | 0.065 | 0.25 | Pass |
| Group M, subtype G | 01 | 10.0 | 1.00 | 13 | 0.251 | 0.46 | Pass |
| | 02 | 20.0 | 1.30 | 12 | 0.235 | 0.46 | Pass |
| | 03 | 30.0 | 1.48 | 12 | 0.184 | 0.46 | Pass |
| | 04 | 40.0 | 1.60 | 12 | 0.123 | 0.46 | Pass |
| | 05 | 100.0 | 2.00 | 12 | 0.091 | 0.25 | Pass |
| | 06 | 1,000.0 | 3.00 | 12 | 0.042 | 0.25 | Pass |
| | 07 | 10,000.0 | 4.00 | 12 | 0.038 | 0.25 | Pass |
| | 08 | 100,000.0 | 5.00 | 12 | 0.039 | 0.25 | Pass |
| | 09 | 1,000,000.0 | 6.00 | 12 | 0.023 | 0.25 | Pass |
| | 10 | 20,000,000.0 | 7.30 | 12 | 0.037 | 0.25 | Pass |
| Group M, subtype H | 01 | 10.0 | 1.00 | 14 | 0.324 | 0.46 | Pass |
| | 02 | 20.0 | 1.30 | 14 | 0.355 | 0.46 | Pass |
| | 03 | 30.0 | 1.48 | 13 | 0.158 | 0.46 | Pass |
| | 04 | 40.0 | 1.60 | 14 | 0.187 | 0.46 | Pass |
| | 05 | 100.0 | 2.00 | 14 | 0.075 | 0.25 | Pass |
| | 06 | 537.0 | 2.73 | 14 | 0.074 | 0.25 | Pass |
| | 07 | 2,884.0 | 3.46 | 14 | 0.037 | 0.25 | Pass |
| | 08 | 15,488.2 | 4.19 | 14 | 0.044 | 0.25 | Pass |
| | 09 | 83,176.4 | 4.92 | 13 | 0.057 | 0.25 | Pass |
| | 10 | 446,683.6 | 5.65 | 13 | 0.066 | 0.25 | Pass |
| Group N | 01 | 2.5 | 0.40 | 13 | 0.221 | 0.46 | Pass |
| | 02 | 5.0 | 0.70 | 13 | 0.140 | 0.46 | Pass |
| | 03 | 10.0 | 1.00 | 14 | 0.101 | 0.46 | Pass |
| | 04 | 20.0 | 1.30 | 15 | 0.117 | 0.46 | Pass |
| | 05 | 30.0 | 1.48 | 13 | 0.066 | 0.46 | Pass |
| | 06 | 40.0 | 1.60 | 13 | 0.081 | 0.46 | Pass |
| | 07 | 100.0 | 2.00 | 14 | 0.065 | 0.25 | Pass |
| | 08 | 416.9 | 2.62 | 14 | 0.048 | 0.25 | Pass |
| | 09 | 1,737.8 | 3.24 | 13 | 0.037 | 0.25 | Pass |
| | 10 | 7,244.4 | 3.86 | 12 | 0.041 | 0.25 | Pass |
| | 11 | 30,199.5 | 4.48 | 14 | 0.030 | 0.25 | Pass |
| | 12 | 125,892.5 | 5.10 | 13 | 0.018 | 0.25 | Pass |
| Group O | 01 | 10.0 | 1.00 | 14 | 0.275 | 0.46 | Pass |
| | 02 | 20.0 | 1.30 | 14 | 0.210 | 0.46 | Pass |

TABLE 30-continued

List of Standard Deviations for HIV-1 Group/subtypes

| Group/Subtype | Panel | Target Concentration (copies/mL) | Target Concentration (log copies/mL) | N* | SD (log copies/mL) | SD Requirement | Pass/Fail |
|---|---|---|---|---|---|---|---|
| | 03 | 30.0 | 1.48 | 14 | 0.128 | 0.46 | Pass |
| | 04 | 40.0 | 1.60 | 13 | 0.141 | 0.46 | Pass |
| | 05 | 100.0 | 2.00 | 14 | 0.097 | 0.25 | Pass |
| | 06 | 1,000.0 | 3.00 | 14 | 0.090 | 0.25 | Pass |
| | 07 | 10,000.0 | 4.00 | 14 | 0.041 | 0.25 | Pass |
| | 08 | 100,000.0 | 5.00 | 14 | 0.065 | 0.25 | Pass |
| | 09 | 1,000,000.0 | 6.00 | 14 | 0.038 | 0.25 | Pass |
| | 10 | 20,000,000.0 | 7.30 | 14 | 0.054 | 0.25 | Pass |

*number of detected replicates

TABLE 31

Summary of Outlier Detection

| HIV-1 Group/Subtype Panel | Outlier Detected |
|---|---|
| Group M, subtype A | No |
| Group M, subtype BF | No |
| Group M, subtype C | No |
| Group M, subtype D | No |
| Group M, subtype AE | No |
| Group M, subtype AG | No |
| Group M, subtype F | No |
| Group M, subtype G | No |
| Group M, subtype H | No |
| Group N | No |
| Group O | No |

TABLE 32

Summary of Regression Parameters

| Group/subtype | Order of Polynomial | Coefficient 1 Intercept | Coefficient 1 Value | Coefficient 1 p-value | Coefficient 2 Value | Coefficient 2 p-value | Coefficient 3 Value | Coefficient 3 p-value | Nonlinear Coefficient Significant | MSE[a] |
|---|---|---|---|---|---|---|---|---|---|---|
| Group M, subtype A | 1 | −0.1188 | 1.0191 | p < 0.0001 | | | | | | 0.0281 |
| | 2 | −0.2073 | 1.0839 | p < 0.0001 | −0.0082 | 0.0682 | | | No | 0.0275 |
| | 3 | −0.6992 | 1.6178 | p < 0.0001 | −0.1581 | p < 0.0001 | 0.0120 | p < 0.0001 | Yes | 0.0233 |
| Group M, subtype BF | 1 | −0.0349 | 1.0223 | p < 0.0001 | | | | | | 0.0399 |
| | 2 | −0.2734 | 1.2467 | p < 0.0001 | −0.0443 | 0.0314 | | | Yes | 0.0388 |
| | 3 | −0.0730 | 0.9575 | 0.0306 | 0.0797 | 0.6646 | −0.0162 | 0.4976 | No | 0.0390 |
| Group M, subtype C | 1 | 0.3755 | 0.9878 | p < 0.0001 | | | | | | 0.0170 |
| | 2 | 0.4395 | 0.9391 | p < 0.0001 | 0.0065 | 0.0994 | | | No | 0.0168 |
| | 3 | 0.2416 | 1.1625 | p < 0.0001 | −0.0600 | 0.0455 | 0.0057 | 0.0257 | Yes | 0.0163 |
| Group M, subtype D | 1 | −0.1297 | 1.0242 | p < 0.0001 | | | | | | 0.0251 |
| | 2 | −0.1381 | 1.0303 | p < 0.0001 | −0.0008 | 0.8455 | | | No | 0.0252 |
| | 3 | −0.3161 | 1.2244 | p < 0.0001 | −0.0555 | 0.0770 | 0.0044 | 0.0788 | No | 0.0248 |
| Group M, subtype AE | 1 | 0.1680 | 0.9921 | p < 0.0001 | | | | | | 0.0203 |
| | 2 | 0.1772 | 0.9853 | p < 0.0001 | 0.0009 | 0.8147 | | | No | 0.0204 |
| | 3 | 0.0623 | 1.1106 | p < 0.0001 | −0.0345 | 0.2229 | 0.0028 | 0.2079 | No | 0.0203 |
| Group M, subtype AG | 1 | 0.0808 | 1.0183 | p < 0.0001 | | | | | | 0.0392 |
| | 2 | 0.0631 | 1.0313 | p < 0.0001 | −0.0016 | 0.7385 | | | No | 0.0394 |
| | 3 | −0.2404 | 1.3627 | p < 0.0001 | −0.0950 | 0.0125 | 0.0075 | 0.0133 | Yes | 0.0380 |
| Group M, subtype F | 1 | −0.0587 | 1.0323 | p < 0.0001 | | | | | | 0.0356 |
| | 2 | −0.1250 | 1.0814 | p < 0.0001 | −0.0062 | 0.1978 | | | No | 0.0354 |
| | 3 | −0.6077 | 1.6104 | p < 0.0001 | −0.1557 | p < 0.0001 | 0.0120 | p < 0.0001 | Yes | 0.0312 |
| Group M, subtype G | 1 | 0.1340 | 0.9982 | p < 0.0001 | | | | | | 0.0209 |
| | 2 | 0.1726 | 0.9695 | p < 0.0001 | 0.0036 | 0.3468 | | | No | 0.0209 |
| | 3 | −0.0552 | 1.2196 | p < 0.0001 | −0.0670 | 0.0237 | 0.0057 | 0.0163 | Yes | 0.0201 |
| Group M, subtype H | 1 | 0.2427 | 0.9747 | p < 0.0001 | | | | | | 0.0319 |
| | 2 | 0.1565 | 1.0457 | p < 0.0001 | −0.0110 | 0.1861 | | | No | 0.0317 |
| | 3 | 0.2003 | 0.9916 | p < 0.0001 | 0.0075 | 0.9113 | −0.0019 | 0.7814 | No | 0.0320 |
| Group N | 1 | 0.5702 | 0.9834 | p < 0.0001 | | | | | | 0.0093 |
| | 2 | 0.5602 | 0.9942 | p < 0.0001 | −0.0020 | 0.6367 | | | No | 0.0093 |
| | 3 | 0.5354 | 1.0392 | p < 0.0001 | −0.0222 | 0.3877 | 0.0025 | 0.4249 | No | 0.0093 |
| Group O | 1 | 0.1490 | 1.0025 | p < 0.0001 | | | | | | 0.0183 |
| | 2 | 0.1646 | 0.9911 | p < 0.0001 | 0.0014 | 0.6668 | | | No | 0.0184 |
| | 3 | 0.0274 | 1.1409 | p < 0.0001 | −0.0408 | 0.1193 | 0.0034 | 0.1039 | No | 0.0182 |

[a]MSE = Mean Square Error

TABLE 33

| | | | | | | |
|---|---|---|---|---|---|---|
| Group/subtype | Panel | Target Concentration (log copies/mL) | Mean Concentration (log copies/mL) | Linear Predicted Value | Polynomial Predicted Value | Difference of Predicted Values | Linearity Check (<=0.5 log IU/mL) |

| Group/subtype | Panel | Target Concentration (log copies/mL) | Mean Concentration (log copies/mL) | Linear Predicted Value | Polynomial Predicted Value | Difference of Predicted Values | Linearity Check (<=0.5 log IU/mL) |
|---|---|---|---|---|---|---|---|
| Group M, Subtype A | 01 | 1.00 | 0.66 | 0.90 | 0.77 | 0.13 | Yes |
| | 02 | 1.30 | 1.16 | 1.21 | 1.16 | 0.04 | Yes |
| | 03 | 1.48 | 1.47 | 1.39 | 1.38 | 0.00 | Yes |
| | 04 | 1.60 | 1.64 | 1.51 | 1.54 | 0.02 | Yes |
| | 05 | 2.00 | 1.95 | 1.92 | 2.00 | 0.08 | Yes |
| | 06 | 3.00 | 3.04 | 2.94 | 3.05 | 0.12 | Yes |
| | 07 | 4.00 | 3.94 | 3.96 | 4.01 | 0.05 | Yes |
| | 08 | 5.00 | 4.95 | 4.98 | 4.93 | 0.04 | Yes |
| | 09 | 6.00 | 5.95 | 6.00 | 5.90 | 0.09 | Yes |
| | 10 | 7.30 | 7.33 | 7.32 | 7.35 | 0.03 | Yes |
| Group M, Subtype BF | 01 | 1.00 | 1.00 | 0.99 | 0.93 | 0.06 | Yes |
| | 02 | 1.30 | 1.13 | 1.30 | 1.27 | 0.02 | Yes |
| | 03 | 1.48 | 1.49 | 1.47 | 1.47 | 0.00 | Yes |
| | 04 | 1.60 | 1.64 | 1.60 | 1.61 | 0.01 | Yes |
| | 05 | 2.00 | 2.06 | 2.01 | 2.04 | 0.03 | Yes |
| | 06 | 2.42 | 2.47 | 2.44 | 2.48 | 0.05 | Yes |
| | 07 | 2.84 | 2.92 | 2.87 | 2.91 | 0.04 | Yes |
| | 08 | 3.26 | 3.35 | 3.30 | 3.32 | 0.02 | Yes |
| | 09 | 3.68 | 3.69 | 3.73 | 3.72 | 0.01 | Yes |
| | 10 | 4.10 | 4.09 | 4.16 | 4.09 | 0.06 | Yes |
| Group M, Subtype C | 01 | 1.00 | 1.38 | 1.36 | 1.35 | 0.01 | Yes |
| | 02 | 1.30 | 1.63 | 1.66 | 1.66 | 0.00 | Yes |
| | 03 | 1.48 | 1.78 | 1.83 | 1.85 | 0.01 | Yes |
| | 04 | 1.60 | 2.03 | 1.96 | 1.97 | 0.02 | Yes |
| | 05 | 2.00 | 2.38 | 2.35 | 2.37 | 0.02 | Yes |
| | 06 | 2.96 | 3.33 | 3.30 | 3.30 | 0.00 | Yes |
| | 07 | 3.92 | 4.17 | 4.25 | 4.22 | 0.03 | Yes |
| | 08 | 4.88 | 5.18 | 5.20 | 5.15 | 0.05 | Yes |
| | 09 | 5.84 | 6.11 | 6.14 | 6.12 | 0.03 | Yes |
| | 10 | 6.80 | 7.16 | 7.09 | 7.16 | 0.07 | Yes |
| Group M, Subtype AG | 01 | 1.00 | 1.04 | 1.10 | 1.03 | 0.06 | Yes |
| | 02 | 1.30 | 1.33 | 1.41 | 1.39 | 0.02 | Yes |
| | 03 | 1.48 | 1.57 | 1.58 | 1.59 | 0.00 | Yes |
| | 04 | 1.60 | 1.79 | 1.71 | 1.73 | 0.02 | Yes |
| | 05 | 2.00 | 2.21 | 2.12 | 2.16 | 0.05 | Yes |
| | 06 | 3.00 | 3.18 | 3.14 | 3.19 | 0.06 | Yes |
| | 07 | 4.00 | 4.14 | 4.15 | 4.17 | 0.01 | Yes |
| | 08 | 5.00 | 5.12 | 5.17 | 5.13 | 0.04 | Yes |
| | 09 | 6.00 | 6.17 | 6.19 | 6.13 | 0.06 | Yes |
| | 10 | 7.30 | 7.54 | 7.52 | 7.55 | 0.04 | Yes |
| Group M, Subtype F | 01 | 1.00 | 0.80 | 0.97 | 0.86 | 0.11 | Yes |
| | 02 | 1.30 | 1.17 | 1.28 | 1.25 | 0.03 | Yes |
| | 03 | 1.48 | 1.56 | 1.47 | 1.47 | 0.00 | Yes |
| | 04 | 1.60 | 1.72 | 1.60 | 1.62 | 0.03 | Yes |
| | 05 | 2.00 | 2.09 | 2.01 | 2.09 | 0.08 | Yes |
| | 06 | 3.00 | 3.09 | 3.04 | 3.15 | 0.11 | Yes |
| | 07 | 4.00 | 4.07 | 4.07 | 4.11 | 0.04 | Yes |
| | 08 | 5.00 | 5.06 | 5.10 | 5.05 | 0.05 | Yes |
| | 09 | 6.00 | 6.09 | 6.14 | 6.04 | 0.10 | Yes |
| | 10 | 7.30 | 7.50 | 7.48 | 7.52 | 0.04 | Yes |
| Group M, Subtype G | 01 | 1.00 | 1.15 | 1.13 | 1.10 | 0.03 | Yes |
| | 02 | 1.30 | 1.38 | 1.43 | 1.43 | 0.00 | Yes |
| | 03 | 1.48 | 1.52 | 1.61 | 1.62 | 0.01 | Yes |
| | 04 | 1.60 | 1.82 | 1.73 | 1.75 | 0.02 | Yes |
| | 05 | 2.00 | 2.19 | 2.13 | 2.16 | 0.03 | Yes |
| | 06 | 3.00 | 3.19 | 3.13 | 3.15 | 0.03 | Yes |
| | 07 | 4.00 | 4.06 | 4.13 | 4.11 | 0.01 | Yes |
| | 08 | 5.00 | 5.08 | 5.12 | 5.08 | 0.05 | Yes |
| | 09 | 6.00 | 6.09 | 6.12 | 6.07 | 0.05 | Yes |
| | 10 | 7.30 | 7.48 | 7.42 | 7.48 | 0.06 | Yes |

The remaining Group/subtypes (HIV-1 Group M subtypes D, AE, H, Group O and Group N) did not demonstrate a significant non-linear coefficient as shown in Table 32.

The least-squares regression plot of the ALINITY m™ HIV-1 assay for each Group/subtype panel is presented in FIG. 10-FIG. 20 and summarized in Tables 34-44.

TABLE 34

ALINITY m ™ HIV-1 Group M, subtype A - Summary for Panel Members within the Linear Range

| | | | | |
|---|---|---|---|---|
| Sample Size (n) | | 120 | | |
| Correlation Coefficient (r) | | 0.997 | | |
| Slope | | 1.02 | | |
| 95% CI for Slope | | (1.00, 1.03) | | |
| Intercept | | −0.12 | | |
| 95% CI for Intercept | | (−0.18, −0.06) | | |
| Target Concentration (log copies/mL) | Min | 1.00 | Max | 7.30 |
| ALINITY m ™ HIV-1 (log copies/mL) | Min | 0.32 | Max | 7.38 |

TABLE 35

ALINITY m ™ HIV-1 Group M, subtype BF - Summary for Panel Members within the Linear Range

| | | | | |
|---|---|---|---|---|
| Sample Size (n) | | 136 | | |
| Correlation Coefficient (r) | | 0.982 | | |
| Slope | | 1.02 | | |
| 95% CI for Slope | | (0.99, 1.06) | | |
| Intercept | | −0.03 | | |
| 95% CI for Intercept | | (−0.12, 0.05) | | |
| Target Concentration (log copies/mL) | Min | 1.00 | Max | 4.10 |
| ALINITY m ™ HIV-1 (log copies/mL) | Min | 0.19 | Max | 4.17 |

TABLE 36

ALINITY m ™ HIV-1 Group M, subtype C - Summary for Panel Members within the Linear Range (Outlier Removed)

| | | | | |
|---|---|---|---|---|
| Sample Size (n) | | 136 | | |
| Correlation Coefficient (r) | | 0.998 | | |
| Slope | | 0.99 | | |
| 95% CI for Slope | | (0.98, 1.00) | | |
| Intercept | | 0.38 | | |
| 95% CI for Intercept | | (0.33, 0.42) | | |
| Target Concentration (log copies/mL) | Min | 1.00 | Max | 6.80 |
| ALINITY m ™ HIV-1 (log copies/mL) | Min | 0.95 | Max | 7.22 |

TABLE 37

ALINITY m ™ HIV-1 Group M, subtype D - Summary for Panel Members within the Linear Range

| | | | | |
|---|---|---|---|---|
| Sample Size (n) | | 136 | | |
| Correlation Coefficient (r) | | 0.997 | | |
| Slope | | 1.02 | | |
| 95% CI for Slope | | (1.01, 1.04) | | |
| Intercept | | −0.13 | | |
| 95% CI for Intercept | | (−0.18, −0.08) | | |
| Target Concentration (log copies/mL) | Min | 1.00 | Max | 7.30 |
| ALINITY m ™ HIV-1 (log copies/mL) | Min | 0.32 | Max | 7.41 |

TABLE 38

ALINITY m ™ HIV-1 Group M, subtype AE - Summary for Panel Members within the Linear Range

| | | | | |
|---|---|---|---|---|
| Sample Size (n) | | 132 | | |
| Correlation Coefficient (r) | | 0.998 | | |
| Slope | | 0.99 | | |

TABLE 38-continued

ALINITY m ™ HIV-1 Group M, subtype AE - Summary for Panel Members within the Linear Range

| | | | | |
|---|---|---|---|---|
| 95% CI for Slope | | (0.98, 1.00) | | |
| Intercept | | 0.17 | | |
| 95% CI for Intercept | | (0.12, 0.21) | | |
| Target Concentration (log copies/mL) | Min | 1.00 | Max | 7.30 |
| ALINITY m ™ HIV-1 (log copies/mL) | Min | 0.82 | Max | 7.54 |

TABLE 39

ALINITY m ™ HIV-1 Group M, subtype AG - Summary for Panel Members within the Linear Range

| | | | | |
|---|---|---|---|---|
| Sample Size (n) | | 139 | | |
| Correlation Coefficient (r) | | 0.996 | | |
| Slope | | 1.02 | | |
| 95% CI for Slope | | (1.00, 1.03) | | |
| Intercept | | 0.08 | | |
| 95% CI for Intercept | | (0.02, 0.14) | | |
| Target Concentration (log copies/mL) | Min | 1.00 | Max | 7.30 |
| ALINITY m ™ HIV-1 (log copies/mL) | Min | 0.28 | Max | 7.67 |

TABLE 40

ALINITY m ™ HIV-1 Group M, subtype F - Summary for Panel Members within the Linear Range

| | | | | |
|---|---|---|---|---|
| Sample Size (n) | | 132 | | |
| Correlation Coefficient (r) | | 0.996 | | |
| Slope | | 1.03 | | |
| 95% CI for Slope | | (1.02, 1.05) | | |
| Intercept | | −0.06 | | |
| 95% CI for Intercept | | (−0.12, 0.00) | | |
| Target Concentration (log copies/mL) | Min | 1.00 | Max | 7.30 |
| ALINITY m ™ HIV-1 (log copies/mL) | Min | 0.38 | Max | 7.58 |

TABLE 41

ALINITY m ™ HIV-1 Group M, subtype G - Summary for Panel Members within the Linear Range

| | | | | |
|---|---|---|---|---|
| Sample Size (n) | | 121 | | |
| Correlation Coefficient (r) | | 0.998 | | |
| Slope | | 1.00 | | |
| 95% CI for Slope | | (0.99, 1.01) | | |
| Intercept | | 0.13 | | |
| 95% CI for Intercept | | (0.09, 0.18) | | |
| Target Concentration (log copies/mL) | Min | 1.00 | Max | 7.30 |
| ALINITY m ™ HIV-1 (log copies/mL) | Min | 0.77 | Max | 7.53 |

TABLE 42

ALINITY m ™ HIV-1 Group M, subtype H - Summary for Panel Members within the Linear Range

| | | | | |
|---|---|---|---|---|
| Sample Size (n) | | 137 | | |
| Correlation Coefficient (r) | | 0.993 | | |
| Slope | | 0.97 | | |
| 95% CI for Slope | | (0.96, 0.99) | | |
| Intercept | | 0.24 | | |
| 95% CI for Intercept | | (0.18, 0.31) | | |
| Target Concentration (log copies/mL) | Min | 1.00 | Max | 5.65 |
| ALINITY m ™ HIV-1 (log copies/mL) | Min | 0.36 | Max | 5.78 |

TABLE 43

ALINITY m™ HIV-1 Group N - Summary for
Panel Members within the Linear Range

| | | | |
|---|---|---|---|
| Sample Size (n) | | | 161 |
| Correlation Coefficient (r) | | | 0.998 |
| Slope | | | 0.98 |
| 95% CI for Slope | | | (0.97, 0.99) |
| Intercept | | | 0.57 |
| 95% CI for Intercept | | | (0.54, 0.60) |
| Target Concentration (log copies/mL) | Min 0.40 | Max | 5.10 |
| ALINITY m™ HIV-1 (log copies/mL) | Min 0.54 | Max | 5.64 |

TABLE 44

ALINITY m™ HIV-1 Group O Linearity Least-Squares Regression
Plot and Summary for Panel Members within the Linear Range

| | | | |
|---|---|---|---|
| Sample Size (n) | | | 139 |
| Correlation Coefficient (r) | | | 0.998 |
| Slope | | | 1.00 |
| 95% CI for Slope | | | (0.99, 1.01) |
| Intercept | | | 0.15 |
| 95% CI for Intercept | | | (0.11, 0.19) |
| Target Concentration (log copies/mL) | Min 1.00 | Max | 7.30 |
| ALINITY m™ HIV-1 (log copies/mL) | Min 0.76 | Max | 7.60 |

For HIV-1 Group M subtypes A, BF, C, D, AE, F, AG, G, H, Group O and Group N, the assay was linear from the lowest virus panel member tested (targeted 1.00 log copies/mL) to the highest virus panel member tested (targeted 7.30 log copies/mL) as shown in Table 45.

For HIV-1 Group M, subtype BF, the assay was linear from the lowest virus panel member tested (targeted 1.00 log copies/mL) to the highest virus panel member tested (targeted 4.10 log copies/mL) as shown in Table 45.

For HIV-1 Group M, subtype C, the assay was linear from the lowest virus panel member tested (targeted 1.00 log copies/mL) to the highest virus panel member tested (targeted 6.80 log copies/mL) as shown in Table 45.

For HIV-1 Group M, subtype H, the assay was linear from the lowest virus panel member tested (targeted 1.00 log copies/mL) to the highest virus panel member tested (targeted 5.65 log copies/mL) as shown in Table 45.

For HIV-1 Group N, the assay was linear from the lowest virus panel member tested (targeted 0.40 log copies/mL) to the highest virus panel member tested (targeted 5.10 log copies/mL) as shown in Table 45.

TABLE 45

Summary of Linear Range

| Group/Subtype | Limit | Panel | Target Concentration (copies/mL) | Target Concentration (log copies/mL) | Acceptance Criteria |
|---|---|---|---|---|---|
| Group M, Subtype A | Lower | 01 | 10.0 | 1.00 | Met |
| | Upper | 10 | 20,000,000.0 | 7.30 | Met |
| Group M, Subtype BF | Lower | 01 | 10.0 | 1.00 | Met |
| | Upper | 10 | 12,589.3 | 4.10 | Met |
| Group M, Subtype C | Lower | 01 | 10.0 | 1.00 | Met |
| | Upper | 10 | 6,309,573.4 | 6.80 | Met |
| Group M, Subtype D | Lower | 01 | 10.0 | 1.00 | Met |
| | Upper | 10 | 20,000,000.0 | 7.30 | Met |
| Group M, Subtype AE | Lower | 01 | 10.0 | 1.00 | Met |
| | Upper | 10 | 20,000,000.0 | 7.30 | Met |
| Group M, Subtype AG | Lower | 01 | 10.0 | 1.00 | Met |
| | Upper | 10 | 20,000,000.0 | 7.30 | Met |
| Group M, Subtype F | Lower | 01 | 10.0 | 1.00 | Met |
| | Upper | 10 | 20,000,000.0 | 7.30 | Met |
| Group M, Subtype G | Lower | 01 | 10.0 | 1.00 | Met |
| | Upper | 10 | 20,000,000.0 | 7.30 | Met |
| Group M, Subtype H | Lower | 01 | 10.0 | 1.00 | Met |
| | Upper | 10 | 446,683.6 | 5.65 | Met |
| Group N | Lower | 01 | 2.5 | 0.40 | Met |
| | Upper | 12 | 125,892.5 | 5.10 | Met |
| Group O | Lower | 01 | 10.0 | 1.00 | Met |
| | Upper | 10 | 20,000,000.0 | 7.30 | Met |

Figure 21:
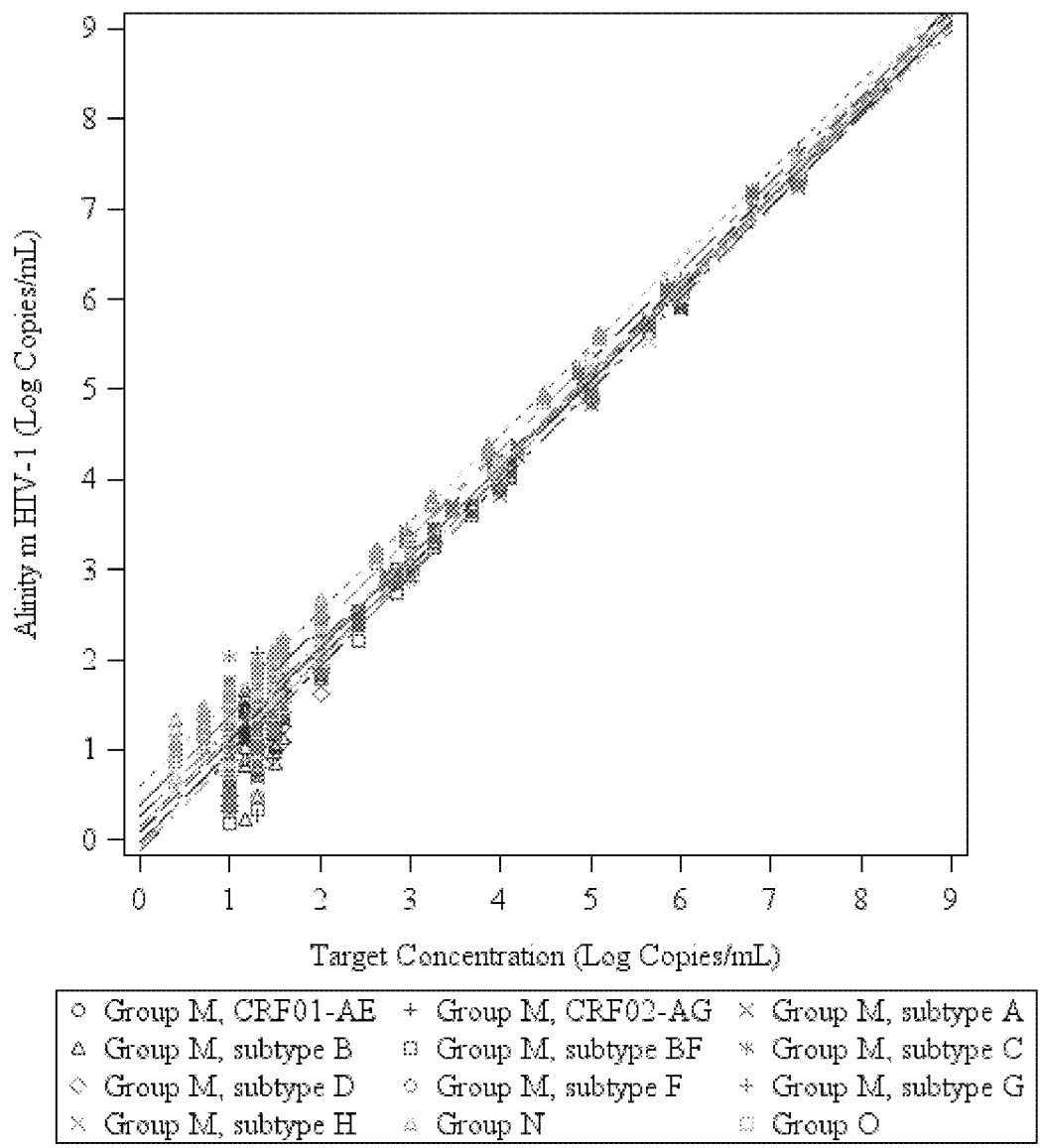
FIG. 21 is a plot of ALINITY m™ HIV-1 Group M, subtypes A, B, BF, C, D, AE, AG, F, G, H, Group N and Group O combined least-squares regression for panel members within the linear range.

A least-squares regression plot for ALINITY m™ HIV-1 linearity panel members, including Group M subtypes A, B, BF, C, D, AE, AG, F, G, H, Group N and Group O combined is presented in FIG. 21.

A least-squares regression summary for ALINITY m™ HIV-1 linearity panel members, including Group M subtypes A, B, BF, C, D, AE, AG, F, G, H, Group N and Group O is shown in Table 46.

TABLE 46

Least-Squares Regression Summary for Panel Members within
the Linear Range for Different Groups/Subtypes

| Genotype | Linear Equation from Linearity Study | Maximum Difference Between Best Fitting Nonlinear Regression and Linear Regression (log copies/mL) |
|---|---|---|
| Group M, subtype A | Y = 1.02X − 0.12 | 0.13 |
| Group M, CRF01-AE | Y = 0.99X + 0.17 | NA |
| Group M, CRF02-AG | Y = 1.02X + 0.08 | 0.06 |
| Group M, subtype B | Y = 1.03X − 0.05 | 0.06 |
| Group M, subtype BF | Y = 1.02X − 0.03 | 0.06 |
| Group M, subtype C | Y = 0.99X + 0.38 | 0.07 |
| Group M, subtype D | Y = 1.02X − 0.13 | NA |
| Group M, subtype F | Y = 1.03X − 0.06 | 0.11 |
| Group M, subtype G | Y = 1.00X + 0.13 | 0.06 |
| Group M, subtype H | Y = 0.97X + 0.24 | NA |
| Group N | Y = 0.98X + 0.57 | NA |
| Group O | Y = 1.00X + 0.15 | NA |

Figure 22:
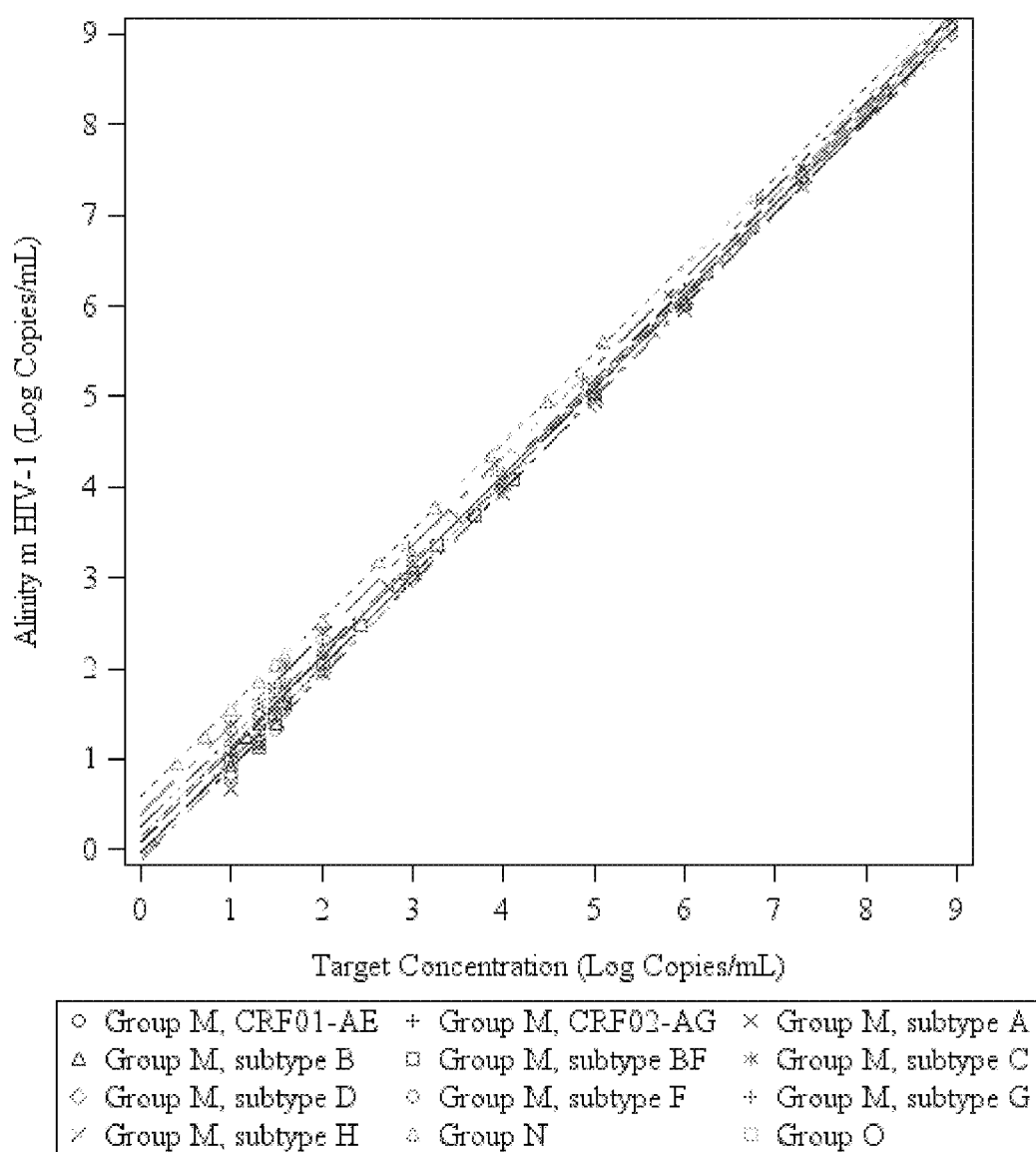
FIG. 22 is a graph showing the mean of each panel member and the regression line from individual data points for Group M subtypes A, B, BF, C, D, AE, AG, F, G, H, Group N and Group O using ALINITY m™ HIV-1 within the linear range.

A plot with the mean of each panel member and the regression line from the regression analysis with all individual data points for Group M subtypes A, B, BF, C, D, AE, AG, F, G, H, Group N and Group O is presented in FIG. 22.

One Group M, subtype A sample was invalid with Code 9210—Internal Control Cycle Number Is Too High. This replicate was excluded from the analysis and additional replicates were tested per the protocol.

One Group O sample was invalid due to instrument error code 5002—Pipettor Arm Z Motor Failed. This sample was excluded from the analysis and was not retested as the minimum sample size was achieved.

Three Group M, subtype AE samples were invalid due to instrument error code 5013—Liquid Level Detection Error on Pipettor Probe. These sample were excluded from the analysis and additional samples were tested per the protocol.

One Group M, subtype AE sample was invalid with Code 9212—Internal Control Failed. This sample was excluded from the analysis and was not retested as the minimum sample size was achieved.

Two Group M, subtype F samples were invalid with Code 9212—IC Fail. These replicates were excluded from the analysis and were not retested as the minimum sample size was achieved.

One Group M, subtype D sample was invalid with Code 9210—Internal Control Cycle Number is Too High. This sample was excluded from the analysis and was not retested as the minimum sample size was achieved.

Two Group M, subtype D samples were invalid with Code 9212—IC Fail. These replicates were excluded from the analysis and were not retested as the minimum sample size was achieved.

Three Group M, subtype BF samples were invalid for Code 9210—Internal Control Cycle Number is Too High. These replicates were excluded from the analysis and were not retested as the minimum sample size was achieved.

One Group M, subtype H sample was invalid with Code 9210—Internal Control Cycle Number is Too High. This sample was excluded from the analysis and was not retested as the minimum sample size was achieved.

One Group M, subtype H sample) was invalid with Code 9212—Internal Control Failed. This sample was excluded from the analysis and was not retested as the minimum sample size was achieved.

One Group M, subtype AG sample was invalid due to instrument error code 5002—Pipettor Arm Z Motor Failed. This sample was excluded from the analysis and was not retested as the minimum sample size was achieved.

Two Group M, subtype C samples were invalid due to with Code 9212—Internal Control Failed. This sample was excluded from the analysis and was not retested as the minimum sample size was achieved.

One Group M, subtype C sample was invalid due to instrument error code 5002—Pipettor Arm Z Motor Failed. This sample was excluded from analysis and was not retested as the minimum sample size was achieved.

One Group M, subtype C sample was invalid with Code 9210—Internal Control Cycle Number is Too High. This sample was excluded from analysis and was not retested as the minimum sample size was achieved.

Nine Group N samples were invalid due to instrument error code 5002—Pipettor Arm Z Motor Failed. Theses samples were excluded from the analysis and retested, as necessary, to meet the minimum sample size.

One Group N sample was invalid due to instrument error code 5013: Liquid Level Detection Error on Pipettor Probe. This sample was excluded from analysis and was not retested as the minimum sample size was achieved.

One Group N sample was invalid with Code 9210—Internal control cycle number is too high. This sample was excluded from analysis and was not retested as the minimum sample size was achieved.

One run was invalid because of an invalid Negative Control (error code 9209) and was excluded. No samples were associated with this Control event. Note that when an assay control is invalid, the ALINITY m™ system software invalidates all control levels tested in that control set. Therefore, the associated High Positive Control and Low Positive Control from this control event were also invalidated. Assay Controls were successfully retested prior to testing of samples.

All test results were reviewed. Certain observations may have been excluded from the analysis in accordance with the protocol exclusion criteria (i.e., control or validity criteria failure, instrument errors or problems, acknowledged technologist error, inclusion criteria not met, and/or protocol not followed). All results that were not excluded were eligible for analysis.

An overall line-listing summary of the total number of included and excluded sample results, and invalid/valid assay control results is provided in Table 47. An explanation of excluded observations is summarized in Table 48.

TABLE 47

ALINITY m ™ HIV-1 Group/subtype Linearity Study
Overall Line Listing Summary

| Total Number of Results | Number of Control Results | | Number of Sample Results | |
|---|---|---|---|---|
| | Valid | Invalid | Included | Excluded |
| 1564 | 36 | 3 | 1493 | 32 |

TABLE 48

ALINITY m ™ HIV-1 Group/Subtype Linearity Study Excluded Data Summary

| Exclusion Code | N | OBS Number(s) | Reason for Exclusion | Impact to Study Conclusion |
|---|---|---|---|---|
| 26 - Invalid sample | 17 | 1, 5, 7, 8, 9, 10, 11, 13, 14, 15, 16, 17, 18, 19, 20, 25, 27 | Samples were invalid and excluded from analysis per the protocol. | There is no impact to the study conclusion. Samples were retested as necessary to meet the minimum sample size for the study. |
| 27 - Invalid run | 3 | 33, 34, 35 | Assay Controls were invalid and were excluded from the analysis. | There is no impact to the study conclusion. No samples were tested as part of the run. Assay Controls were successfully retested prior to testing samples. |
| 31 - Instrument error | 15 | 2, 3, 4, 6, 12, 21, 22, 23, 24, 26, 28, 29, 30, 31, 32 | Samples were invalid due to instrument errors and were excluded from the analysis. | There is no impact to the study conclusion. Samples were retested as necessary to meet the minimum sample size for the study. |

A total of 1564 results were generated in the Group/study linearity study: a total of 1493 results were included in the analyses, a total of 32 results excluded from the analyses, 36 valid control results, and 3 invalid control results.

The results of this example confirm that the ALINITY m™ HIV-1 assay is linear between 10 and 20,000,000 copies/mL for HIV-1 Group M subtypes A, D, AE, AG, F, G and Group O. The claimed linear range for the ALINITY m™ HIV-1 assay is 20 copies/mL to 10,000,000 copies/mL. For Group M subtypes BF, C, H and Group N, where the panel member did not achieve 10,000,000 copies/mL due to limitations in available volume and/or concentration, the assay was linear from less than or equal to 10 copies/mL to the highest panel concentration tested.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the," "at least one," "one or more," and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. The phrase "consisting essentially of" also is construed to be an open-ended phrase meant to include steps or materials which do not materially affect the basic and novel characteristics of a described product or method. The phrase "consisting of" is construed to be a closed phrase which excludes any element, step, or ingredient not explicitly specified in the specification or claims. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A set of oligonucleotide sequences for amplifying and detecting one or more human immunodeficiency virus-1 (HIV-1) nucleic acid sequences in a sample, which comprises:

(a) a primer and probe set that amplifies and detects at least a portion of the HIV-1 integrase (INT) gene comprising a forward primer oligonucleotide sequence comprising SEQ ID NO: 1, a reverse primer oligonucleotide sequence comprising SEQ ID NO: 2, and a double-stranded probe oligonucleotide sequence comprising SEQ ID NO: 3, SEQ ID NO: 4, a detectable label, and a quencher moiety, and (b) a primer and probe set that amplifies and detects at least a portion of an HIV-1 long terminal repeat (LTR) region, which comprises a forward primer oligonucleotide sequence comprising SEQ ID NO: 5, a reverse primer oligonucleotide sequence comprising SEQ ID NO: 6, a first double-stranded probe oligonucleotide sequence, and a second double-stranded probe oligonucleotide sequence, wherein (i) the first double-stranded probe oligonucleotide sequence comprises SEQ ID NO: 7, SEQ ID NO: 8, a detectable label, and a quencher moiety; and (ii) the second double-stranded probe oligonucleotide sequence comprises SEQ ID NO: 9, SEQ ID NO: 10, a detectable label, and a quencher moiety.

2. The set of claim 1, further comprising:

(c) an internal control forward primer oligonucleotide sequence comprising SEQ ID NO: 11, SEQ ID NO: 53, or SEQ ID NO: 54, (d) an internal control reverse primer oligonucleotide sequence comprising SEQ ID NO: 12, and (e) an internal control probe oligonucleotide sequence comprising SEQ ID NO: 13 and a detectable label.

3. The set of claim 1, wherein the detectable label is a fluorophore.

4. A method for detecting human immunodeficiency virus-1 (HIV-1) in a sample suspected of containing HIV-1, which method comprises:

(a) contacting a sample obtained from a human with the set of oligonucleotide sequences of claim 1 and reagents for amplification and detection of nucleic acid sequences,
(b) amplifying at least a portion of the HIV-1 INT gene and/or at least a portion of the HIV-1 LTR region present in the sample,
(c) hybridizing the double-stranded probe oligonucleotide that detects a portion of the HIV-1 INT gene to the amplified portion of the HIV-1 INT gene, and/or hybridizing the first and second double-stranded probe oligonucleotide sequences that detect a portion of the HIV-1 LTR region to the amplified portion of the HIV-1 LTR region,
(d) detecting hybridization of the probe oligonucleotide sequences to the portions of the HIV-1 INT gene and/or LTR region by assessing a signal from each of the detectable labels, whereby
  (i) the presence of the signal from the detectable label on the double-stranded probe oligonucleotide sequence that detects at least a portion of the HIV-1 INT gene indicates hybridization of the probe oligonucleotide sequence to the portion of the HIV-1 INT gene and the presence of HIV-1 in the sample; and/or
  (ii) the presence of a signal from the first double-stranded probe oligonucleotide sequence and/or the second double-stranded probe oligonucleotide sequence indicates hybridization of the first double-stranded probe oligonucleotide sequence and/or second double-stranded probe oligonucleotide sequence to the portion of the LTR region and the presence of HIV-1 in the sample, and
  (iii) the absence of the signals indicates the absence of HIV-1 in the sample.

5. The method of claim 4, wherein the sample comprises blood, serum, plasma, saliva, urine, vaginal fluid, or semen.

6. A kit for detecting human immunodeficiency virus-1 (HIV-1) in a sample comprising:
(a) a primer and probe set that amplifies and detects at least a portion of the HIV-1 integrase (INT) gene comprising a forward primer oligonucleotide sequence comprising SEQ ID NO: 1, a reverse primer oligonucleotide sequence comprising SEQ ID NO: 2, and a double-stranded probe oligonucleotide sequence comprising SEQ ID NO: 3, SEQ ID NO: 4, a detectable label, and a quencher moiety, and
(b) a primer and probe set that amplifies and detects at least a portion of the HIV-1 long terminal repeat (LTR) region, which comprises a forward primer oligonucleotide sequence comprising SEQ ID NO: 5, a reverse primer oligonucleotide sequence comprising SEQ ID NO: 6, a first double-stranded probe oligonucleotide sequence, and a second double-stranded probe oligonucleotide sequence, wherein
  (i) the first double-stranded probe oligonucleotide sequence comprises SEQ ID NO: 7, SEQ ID NO: 8, a detectable label, and a quencher moiety; and
  (ii) the second double-stranded probe oligonucleotide sequence comprises SEQ ID NO: 9, SEQ ID NO: 10, a detectable label, and a quencher moiety;
(c) reagents for amplifying and detecting nucleic acid sequences; and
(d) instructions for use.

7. The kit of claim 6, which further comprises:
(e) an internal control forward primer oligonucleotide sequence comprising SEQ ID NO: 11, SEQ ID NO: 53, or SEQ ID NO: 54,
(f) an internal control reverse primer oligonucleotide sequence comprising SEQ ID NO: 12, and
(g) an internal control probe oligonucleotide sequence comprising SEQ ID NO: 13 and a detectable label.

8. The kit of claim 6, wherein the primers, probes, and reagents are lyophilized.

9. A composition for amplifying and detecting human immunodeficiency virus-1 (HIV-1) in a sample, which comprises:
(a) a primer and probe set that amplifies and detects at least a portion of the HIV-1 integrase (INT) gene comprising a forward primer oligonucleotide sequence comprising SEQ ID NO: 1, a reverse primer oligonucleotide sequence comprising SEQ ID NO: 2, and a double-stranded probe oligonucleotide sequence comprising SEQ ID NO: 3, SEQ ID NO: 4, a detectable label, and a quencher moiety, and
(b) a primer and probe set that amplifies and detects at least a portion of the HIV-1 long terminal repeat (LTR) region, which comprises a forward primer oligonucleotide sequence comprising SEQ ID NO: 5, a reverse primer oligonucleotide sequence comprising SEQ ID NO: 6, a first double-stranded probe oligonucleotide sequence, and a second double-stranded probe oligonucleotide sequence, wherein
  (i) the first double-stranded probe oligonucleotide sequence comprises SEQ ID NO: 7, SEQ ID NO: 8, a detectable label, and a quencher moiety; and
  (ii) the second double-stranded probe oligonucleotide sequence comprises SEQ ID NO: 9, SEQ ID NO: 10, a detectable label, and a quencher moiety.

10. The composition of claim 9, which further comprises:
(c) an internal control forward primer oligonucleotide sequence comprising SEQ ID NO: 11, SEQ ID NO: 53, or SEQ ID NO: 54,
(d) an internal control reverse primer oligonucleotide sequence comprising SEQ ID NO: 12, and
(e) an internal control probe oligonucleotide sequence comprising SEQ ID NO: 13 and a detectable label.

11. The composition of claim 9, wherein the primer oligonucleotides, probe oligonucleotides, and reagents are lyophilized.

* * * * *